(12) United States Patent
Herrmann et al.

(10) Patent No.: US 9,610,333 B2
(45) Date of Patent: Apr. 4, 2017

(54) METHODS, COMPOSITIONS AND KITS FOR VEGETATIVE CELL-BASED VACCINES AND SPORE-BASED VACCINES

(75) Inventors: John E. Herrmann, Northborough, MA (US); Boris R. Belitsky, Swampscott, MA (US); Abraham L. Sonenshein, Brookline, MA (US); Saul Tzipori, Shrewsbury, MA (US)

(73) Assignee: Tufts University, Boston, MA (US)

( * ) Notice: Subject to any disclaimer, the term of this patent is extended or adjusted under 35 U.S.C. 154(b) by 492 days.

(21) Appl. No.: 12/987,280

(22) Filed: Jan. 10, 2011

(65) Prior Publication Data

US 2011/0104200 A1 May 5, 2011

Related U.S. Application Data

(63) Continuation-in-part of application No. PCT/US2009/050356, filed on Jul. 13, 2009.

(60) Provisional application No. 61/405,950, filed on Oct. 22, 2010, provisional application No. 61/134,700, filed on Jul. 11, 2008.

(51) Int. Cl.
| | | |
|---|---|---|
| *A61K 39/00* | (2006.01) | |
| *A61K 39/08* | (2006.01) | |
| *A61K 39/15* | (2006.01) | |
| *A61K 39/12* | (2006.01) | |
| *A61K 35/742* | (2015.01) | |

(52) U.S. Cl.
CPC .............. *A61K 39/00* (2013.01); *A61K 39/08* (2013.01); *A61K 39/12* (2013.01); *A61K 39/15* (2013.01); *A61K 35/742* (2013.01); *A61K 2039/523* (2013.01); *A61K 2039/541* (2013.01); *A61K 2039/542* (2013.01); *A61K 2039/543* (2013.01); *A61K 2039/545* (2013.01); *A61K 2039/55544* (2013.01); *A61K 2039/6006* (2013.01); *C07K 2319/00* (2013.01); *C12N 2720/12334* (2013.01)

(58) Field of Classification Search
None
See application file for complete search history.

(56) References Cited

U.S. PATENT DOCUMENTS

| | | | |
|---|---|---|---|
| 5,800,821 A | 9/1998 | Acheson et al. | |
| 6,165,993 A | 12/2000 | Herrmann et al. | |
| 6,187,319 B1 | 2/2001 | Herrmann et al. | |
| 6,849,256 B1 * | 2/2005 | Farmer ................ | A61K 35/742 424/93.46 |
| 7,300,659 B2 * | 11/2007 | Finlay et al. ............. | 424/234.1 |
| 2005/0232947 A1 * | 10/2005 | Cutting ..................... | 424/200.1 |
| 2005/0287168 A1 | 12/2005 | Cutting | |

FOREIGN PATENT DOCUMENTS

| | | | |
|---|---|---|---|
| GB | 2003055513 A2 | | 7/2003 |
| WO | WO 02/00232 | * | 1/2002 |
| WO | WO 03/005513 | * | 7/2003 |

OTHER PUBLICATIONS

Paccez et al. Vaccine 24 (2006) 2935-2943.*
Gerald DJ Adams. Lyophilization of Vaccines. Methods in Molecular Medicine, vol. 87: Vaccine Protocols 2nd ed. Edited by: A Robinson, MJ Hudson and MP Cranage. Human Press Inc. Totowa, NJ published Aug. 27, 2003.*
Rubina Shaheen. Indian Journal for the Practising Doctor. vol. 1, No. 4 (Jan. 2005-Feb. 2005) retrieved Aug. 4, 2014 from http://www.inmedica.com/journals.php?journalid=3&issueid=6&articleid=99&action=article.*
Paccez et al. Vaccine 25 (2007) 4671-4680 Apr. 25, 2007.*
Cano et al. "Revival and identification of bacterial spores in 25-to 40-million-year-old Dominican amber" 1995 Science, vol. 268, pp. 1060-1064.
Casula et al. "Bacillus Probiotics: Spore Germination in Gastrointestinal Tract" 2002 Appl Environment Microbiol, vol. 68, pp. 2344-2352.
Dubnau et al. "Two-component regulators and genetic competence in Bacillus subtilis" 1994 Res Microbiol, vol. 145, pp. 403-411.
Duc et al. " Bacterial Spores as Vaccine Vehicles" 2003, Infect Immun, vol. 71, pp. 2810-2818.
Fouet et al. "A Target for Carbon Source-Dependent Negative Regulation of the citB Promoter of Bacillus subtilis" 1990, J Bacteriol, vol. 172, pp. 835-844.
Galen et al. "A murine model of intranasal immunization to assess the immunogenicity of attenuated *Salmonella typhi* live vector vaccines in stimulating serum antibody responses to expressed foreign antigens" 1997, Vaccine, vol. 15, pp. 700-709.
Grangette et al. "Mucosal Immune Responses and Protection against Tetanus Toxin after Intranasal Immunization with Recombinant Lactobacillus plantarum" 2001, Infect Immun, pp. 1547-1553.
Harry et al. "Use of Immunofluorescence to Visualize Cell-Specific Gene Expression during Sporulation in Bacillus subtilis" 1995, J Bacteriol, vol. 177, pp. 3386-3393.
Hopwood et al. Genetic manipulation of Streptomyces: a laboratory manual. 1985. Publ. by The John Innes Foundation, Norwich, England.
Kieser et al. Practical Streptomyces Genetics. 2008. Publ. by The John Innes Foundation, Norwich, England.
Luiz et al. "Boosting systemic and secreted antibody responses in mice orally immunized with recombinant Bacillus subtilis strains following parenteral priming with a DNA vaccine encoding the enterotoxigenic *Escherichia coli* (ETEC) CFA/I fimbriae B subunit" 2008, Vaccine, vol. 26, pp. 3998-4005.

(Continued)

*Primary Examiner* — Oluwatosin Ogunbiyi
(74) *Attorney, Agent, or Firm* — Lawson & Weitzen LLP; Sonia K. Guterman

(57) ABSTRACT

Methods for immunizing a subject to an antigen of an infectious agent, a tumor, or an allergen are provided, using vegetative cytoplasmic expression of the antigen or spore surface display of the antigen, and contacting the subject with a composition including a spore or a vegetative cell or both with or without an adjuvant. Also included are thermally-stable vaccine compositions using the method described above and kits including the compositions.

23 Claims, 47 Drawing Sheets

(56) References Cited

OTHER PUBLICATIONS

Mauriello et al. "Germination-independent induction of cellular immune response by Bacillus subtilis spores displaying the C fragment of the tetanus toxin" 2007, Vaccine, vol. 25, pp. 788-793.
Middleton et al. "New shuttle vectors for ectopic insertion of genes into Bacillus subtilis" 2004, Plasmid, vol. 51, pp. 238-245.
Nicholson et al. "Resistance of Bacillus Endospores to Extreme Terrestrial and Extraterrestrial Environments" 2000, Microbiol Mol Biol Rev, vol. 64, pp. 548-572.
Oggioni et al. "Bacillus spores for vaccine delivery" 2003, Vaccine, vol. 21, pp. S2/96-S2/101.
Pitt et al. "Heat Resistance of Xerophilic Fungi Based on Microscopical Assessment of Spore Survival" 1970, Appl Microbiol, vol. 20, pp. 682-686.
Put et al. "The heat resistance of ascospores of four *Saccharomyces* spp. isolated from spoiled heat-processed soft drinks and fruit products" 1982 J Appl Bacteriol, vol. 52, pp. 235-243.
Sonenshein et al. eds., Bacillus and Other Gram-Positive Bacteria: Biochemistry, Physiology, and Molecular Genetics, 1993. Publ. by Wiley-Blackwell.
Spinosa et al. "On the fate of ingested Bacillus spores" 2000 Res Microbiol, vol. 151, pp. 361-368.
Uyen et al. "Enhanced immunisation and expression strategies using bacterial spores as heat-stable vaccine delivery vehicles" 2007, Vaccine, vol. 25, pp. 356-365.
Yamamoto et al. "A nontoxic mutant of cholera toxin elicits Th2-type responses for enhanced mucosal immunity" 1997 Proc Natl Acad Sci, vol. 94, pp. 5267-5272.
Yansura et al. "Use of the *Escherichia coli* lac repressor and operator to control gene expression in Bacillus subtilis" 1984, Proc Natl Acad Sci, vol. 81, pp. 439-443.

\* cited by examiner agatctacacagcccagtccagactattcggcactgaaat
tatgggtgaagtggtcaagacctcactaggcacctaaaa
atagcgcacctgaagaagatttatttgaggtagcccttg
cctacctagcttccagatatcctaacagcacacaaga
gcggaagatgttttgttctacatccagaacacctctgc
taaaattcctgaaaattttgcaaaaagttgttgacttta
tctacaaggtgtggTataatgtgtggGattgtgagcggat
ctaga

Normal mice

| | 3 days after | | | |
|---|---|---|---|---|
| | 1st inoculation | 2nd inoculation | 3rd inoculation | Total mice |
| 49NA | BB3059 veg cells | 5 | 5 | 5 | 15 |
| 49NB | BB3184 spores | 5 | 5 | 5 | 15 |
| 49NC | Sterile H$_2$O | 5 | 5 | 5 | 15 |

SCID mice

| | 3 days after | | | |
|---|---|---|---|---|
| | 1st inoculation | 2nd inoculation | 3rd inoculation | Total mice |
| 49SA | BB3059 veg cells | 5 | 5 | 5 | 15 |
| 49SB | BB3184 spores | 5 | 5 | 5 | 15 |
| 49SC | Sterile H$_2$O | 5 | 5 | 5 | 15 |

* SCID mice were preconditioned with 1 mg of anti-IFN-γ before immunization

Fig. 31

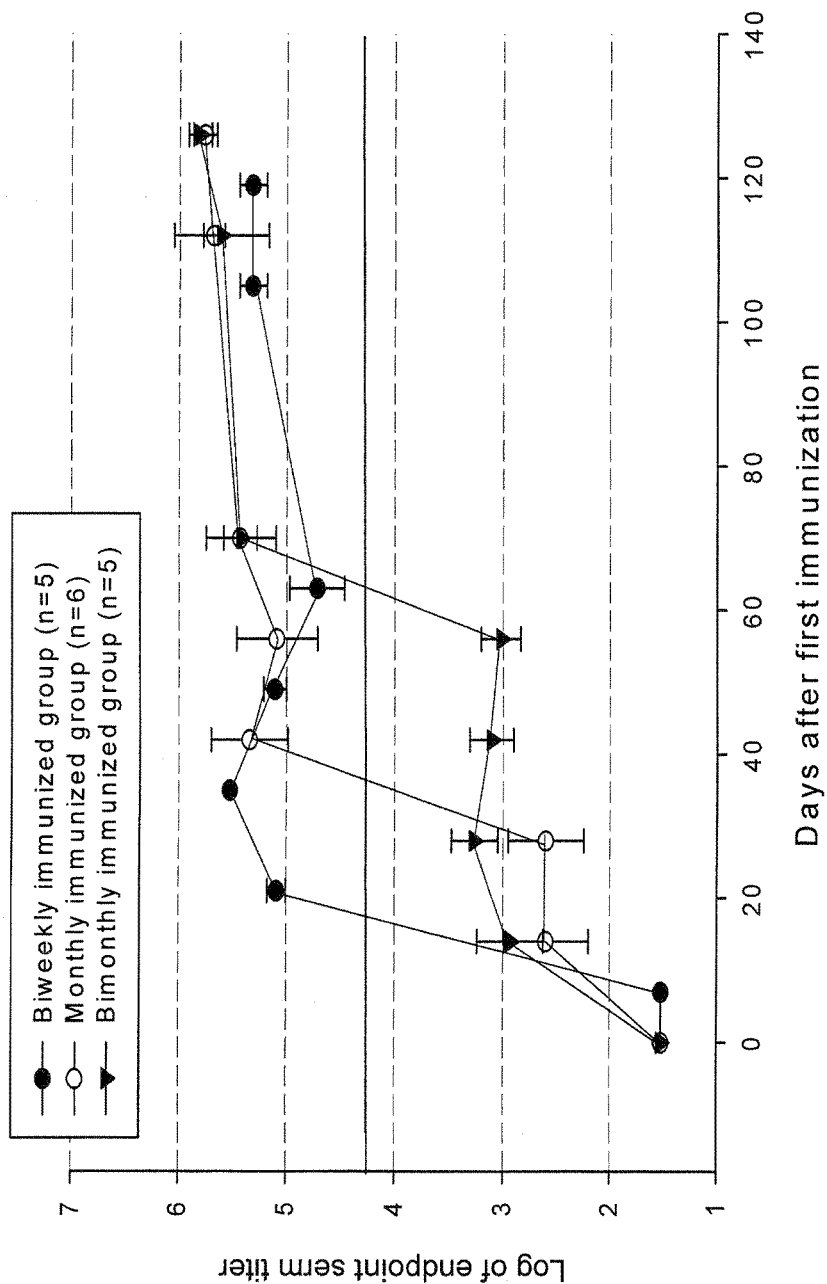

SEQUENCE LISTING

```
<160> NUMBER OF SEQ ID NOS: 1

<210> SEQ ID NO 1
<211> LENGTH: 285
<212> TYPE: DNA
<213> ORGANISM: Artificial Sequence
<220> FEATURE:
<223> OTHER INFORMATION: The sequence was designed and synthesized

<400> SEQUENCE: 1
agatctacac agcccagtcc agactattcg gcactgaaat tatgggtgaa gtggtcaaga        60
cctcactagg caccttaaaa atagcgcacc ctgaagaaga tttatttgag gtagcccttg       120
cctacctagc ttccaagaaa gatatcctaa cagcacaaga gcggaaagat gttttgttct       180
acatccagaa caacctctgc taaaattcct gaaaaatttt gcaaaaagtt gttgacttta       240
tctacaaggt gtggtataat gtgtgggatt gtgagcggat ctaga                      285
```

METHODS, COMPOSITIONS AND KITS FOR VEGETATIVE CELL-BASED VACCINES AND SPORE-BASED VACCINES

RELATED APPLICATIONS

The present invention claims the benefit of and is a continuation in part of PCT application number PCT/US2009/50356 filed Jul. 13, 2009 which claims the benefit of U.S. provisional application Ser. No. 61/134,700 filed Jul. 11, 2008, and also claims the benefit of U.S. provisional application Ser. No. 61/405,950 filed Oct. 22, 2010, each of which is hereby incorporated by reference herein in its entirety.

TECHNICAL FIELD

Methods and vaccines are provided for immunizing a subject with a vaccine that is a fusion to a spore coat protein or a vegetative cytoplasmic expression of an antigen of an infectious agent, a tumor, or an allergen and thermally-stable vaccine compositions.

BACKGROUND

*Bacillus subtilis* is a Gram-positive, catalase-positive bacterium commonly found in soil. Members of the genus *Bacillus* have the ability to form tough, protective endospores, a characteristic which allows the spores of the organism to tolerate extreme environmental conditions, to be heat resistant, and to quantitatively survive lengthy exposure to a wide range of temperatures including freezing and boiling, without loss of viability.

*B. subtilis* has a long safety record as a food component and as a probiotic, e.g., used in microbial feed supplements to improve intestinal microbial balance by competitively excluding pathogens both in animals and humans. Other *Bacillus* species are well-known biological insecticidal agents, e.g., *Bacillus thuringiensis* (Dipel®) is used to combat gypsy moths without harm to other wildlife. *Bacillus natto* includes food-grade strains mainly used for the fermentation of soybeans, which fermentation process eventually results in a cheap and nutritious food that is rich in amino acids. In fact the term "natto" refers to a Japanese soybean fermented product "Natto", which is a widely used commercial product.

Bacilli have been studied extensively by researchers and as a result this family includes species with well-characterized genetic and physiological systems. *B. subtilis* has become a model organism for Gram-positive bacteria, and numerous studies have been published involving manipulation of its genetic structure and regulation of expression of its proteins.

There remains a need for vaccines that are easily produced in large quantities and at low cost to prevent and control emerging viral epidemic and epizootic diseases. Vaccines based on bacterial production systems that can be stabilized for use in tropical areas and under other conditions to minimize loss of activity in areas having minimal storage capabilities are available.

SUMMARY

An embodiment of the invention provides a method of immunizing a subject to an infectious agent, a tumor, or an allergen, the method including: providing a vegetative host bacterial cell including an isolated nucleotide sequence encoding an antigen of the infectious agent, the tumor, or the allergen, such that the nucleotide sequence is operably linked to a promoter for cytoplasmic vegetative expression of the antigen or for expression of the antigen as a fusion to a spore coat protein, such that at least one of vegetative cells and spores are associated with the antigen; and, contacting a mucosal tissue of the subject with a composition including at least one of the vegetative cells and the spores, such that the antigen immunizes the subject to the infectious agent, the tumor, or to the allergen.

In a related embodiment of the method, the infectious agent is selected from: a bacterium, a fungus, a virus, a protozoan, or a protein product thereof. In a related embodiment, the infectious agent is at least one bacterium selected from: *Bacillus* for example *B. anthracis*; *Clostridium* for example *C. tetani*, *C. difficile*, and *C. perfringens*; *Corynebacterium* for example *C. diphtherias*; *Bordetella* for example *B. pertussis*; *Mycobacterium* for example *M. tuberculosis*; *Salmonella* for example *S. enterica*; *Staphylococcus* for example *S. aureus* and *S. epidermis*; *Streptococcus* for example *S. pneumoniae* and *S. mutans*; *Treponema* for example *T. pallidum*; *Plasmodium* for example *P. falciparum*, *P. vivax*, *P. malariae*, and *P. ovale*; *Pseudomonas* for example *P. aeruginosa*; *Neisseria* for example *N. gonorrhoeae*; *Escherichia coli* for example *E. coli* O157:H7; *Shigella* for example *S. enteritis* and *S. flexneri*; *Campylobacter* for example *C. jejuni*; *Yersinia* for example *Y. pseudotuberculosis* and *Y. pestis*; *Listeria* for example *L. monocytogenes*; *Vibrio* for example *V. cholerae*; and the like. In a related embodiment, the infectious agent is at least one virus selected from: human immunodeficiency virus (HIV); influenza virus for example influenza A or B, for example A/H1N1; polio; herpes for example Herpes simplex virus-1 and Herpes simplex virus-2; smallpox; measles; mumps; rubella; rotavirus; chicken pox; rabies; West Nile virus; Ebola for example Ebola hemorrhagic fever; eastern equine encephalitis; norovirus; hepatitis for example Hepatitis A, Hepatitis B, and Hepatitis C; and the like. In a related embodiment, the infectious agent is at least one fungus selected from: *Cryptococcus* for example *C. Gattii* and *C. neoformans* v. *neoformans*; *Candida* for example *C. albicans*; *Aspergillus* for example *A. flavus* and *A. fumigatus*; and the like. In a related embodiment, the infectious agent is at least one protozoan selected from: *Entamoeba* for example *E. histolytica*; *Giardia* for example *G. lamblia*; *Cryptosporidium* for example *C. parvum*; *Naegleria* for example *N. fowleri* and *N. gruberi*; and the like.

In a related embodiment of the method, the antigen is a rotavirus antigen, for example of bovine, human, or murine origin, or the antigen is a bacterial toxin antigen, for example, a *Clostridium tetani* tetanus toxin antigen. In related embodiments, the rotavirus antigen is a viral virion protein, for example the viral virion protein is selected from: VP2, VP4, VP6, VP7, NSP4, and a portion or a derivative thereof.

In a related embodiment, the allergen includes a macromolecule or portion thereof associated with an increased immunoglobulin level or allergic response in the subject, for example the allergen includes an environmental allergen, animal or plant allergen, or food allergen, for example the allergen is associated with pollen for example ragweed, dust mite proteases for example as found in dust mite excretion, fungus for example mold, pet dander or saliva, shellfish, seafood, a legume such as peanuts, and the like.

In a related embodiment of the method, the subject is a vertebrate animal. For example the vertebrate animal is selected from: an agricultural animal, a high value zoo animal, a research animal, a human, and a wild animal in a dense human environment. For example the vertebrate animal is a cow, a dog, or a pig.

In a related embodiment, contacting the mucosal tissue of the subject further involves administering the composition by a route selected from: intravenous, intramuscular, intraperitoneal, intradermal, intrapulmonary, intravaginal, rectal, oral, buccal, sublingual, intranasal, intraocular, and subcutaneous.

In a related embodiment, contacting the mucosal tissue of the subject involves applying to the mucosal tissue at least one of: an aerosol, a mist, a nose drop, an eye drop, a mouth drop, a capsule, a tablet, a pill, a powder, a granule, a fluid, a suspension, an emulsion, a gel, a patch, and a lozenge.

In a related embodiment, the method further involves after providing the vegetative host bacterial cell and contacting the mucosal tissue of the subject, immunizing the subject with the host bacterial cell, for example the host bacterial cell includes a *Bacillus* cell. For example, the *Bacillus* is *Bacillus subtilis*.

In a related embodiment of the method, contacting the mucosal tissue of the subject further includes contacting the mucosal tissue with an adjuvant. In a related embodiment of the method, the adjuvant is selected from: cholera toxin, a non-toxic variant of *Escherichia coli* labile toxin, and a portion or a derivative thereof.

In a related embodiment, the method further includes prior to contacting the mucosal tissue of the subject, lyophilizing the composition. For example, the composition is lyophilized and distributed under vacuum in a tube or vial.

In a related embodiment, the method further includes observing resistance of the composition to at least one condition selected from: heat, drying, freezing, deleterious chemicals, and radiation. Alternatively, the method includes observing resistance of the composition to accumulation of moisture. In a related embodiment of the method, the resistance to heat includes observing resistance at 60° C. or 45° C. for hours, days, months, for example at least six months, or years, for example at least one year or at least two years. In a related embodiment of the method, observing resistance includes observing a heat treated composition maintaining ability to confer on the subject full protective immunity or at least partial protective immunity, such that the partial protective immunity includes a percentage of the full protective immunity, such that the percentage includes at least 40%, at least 50%, at least 60%, at least 70%, at least 80%, or at least 90%.

In a related embodiment, the method further includes: measuring an antibody titer in serum of the subject administered the composition, such that an increase in antibody for the antigen in comparison to a control serum not administered the composition is an indication of efficacy of the immunogenicity of the composition. For example, the antibody is anti-TetC IgG or IgA.

In a related embodiment, the method further includes: measuring an amount of antigen shedding in the subject having been afflicted by the infectious agent, such that a decrease in fecal antigen as compared to that in a control also afflicted by the infectious agent and not contacted with the composition is a measure of efficacy of the immunogenicity of the composition.

In a related embodiment of the method, the isolated nucleotide sequence encodes an antigen of a *Clostridium tetani* tetanus toxin antigen, such that the nucleotide sequence is operably linked to a promoter for cytoplasmic vegetative expression of the *Clostridium tetani* tetanus toxin antigen or for expression of the *Clostridium tetani* tetanus toxin antigen as a fusion to a spore coat protein, such that at least one of vegetative cells and spores are associated with the *Clostridium tetani* tetanus toxin antigen.

An embodiment of the invention provides a thermally-stable vaccine composition for immunizing a subject with an antigen from an infectious agent, a tumor, or an allergen, the composition including at least one of vegetative cells and spores from a *Bacillus* cell, such that the cells include an isolated nucleotide sequence encoding the antigen, the nucleotide sequence being genetically engineered and integrated into the host bacterial chromosome or carried on a plasmid and provided with appropriate transcriptional and translational regulatory sequences, so that the cells express the antigen cytoplasmically during vegetative growth, or the cells express the antigen during sporulation as a genetic fusion to a spore coat protein so that upon sporulation by the cells the antigen is associated with the vegetative cells, the spores, or both, and such that the composition is effective when applied to a mucosal tissue of the subject to immunize the subject from the infectious agent, tumor, or the allergen.

In a related embodiment, the *Bacillus* is *Bacillus subtilis*. In a related embodiment, the composition further includes an adjuvant. For example, the adjuvant is selected from at least one of: cholera toxin, a non-toxic variant of *Escherichia coli* labile toxin, and a portion or a derivative thereof.

In a related embodiment of the composition, the isolated nucleotide sequence encoding the antigen which is from a strain that is mammalian, for example bovine, human or murine.

In a related embodiment, the composition is treated to remove substantially all water by at least one of technique, for example, centrifugation, vacuum, lyophilization, spray drying, and the like. For example, the composition is dried at 37° C. overnight.

In a related embodiment of the composition, the infectious agent is selected from the group of: a bacterium, a fungus, a virus, a protozoan, or a protein product thereof. In a related embodiment of the composition, the infectious agent is at least one bacterium selected from: *Bacillus* for example *B. anthracis; Clostridium* for example *C. tetani, C. difficile,* and *C. perfringens; Corynebacterium* for example *C. diphtheriae; Bordetella* for example *B. pertussis; Mycobacterium* for example *M. tuberculosis; Salmonella* for example *S. enterica; Staphylococcus* for example *S. aureus* and *S. epidermis; Streptococcus* for example *S. pneumoniae* and *S. mutans; Treponema* for example *T. pallidum; Plasmodium* for example *P. falciparum, P. vivax, P. malariae,* and *P. ovale; Pseudomonas* for example *P. aeruginosa; Neisseria* for example *N. gonorrhoeae; Escherichia coli* for example *E. coli* O157:H7; *Shigella* for example *S. enteritis* and *S. flexneri; Campylobacter* for example *C. jejuni; Yersinia* for example *Y. pseudotuberculosis* and *Y. pestis; Listeria* for example *L. monocytogenes; Vibrio* for example *V. cholerae;* and the like.

In a related embodiment of the composition, the infectious agent is at least one virus selected from the group of: human immunodeficiency virus (HIV); influenza virus for example influenza A or B, for example A/H1N1, polio; herpes for example Herpes simplex virus-1 and Herpes simplex virus-2; smallpox; measles; mumps; rubella; rotavirus; chicken pox; rabies; West Nile virus; Ebola for example Ebola hemorrhagic fever; eastern equine encephalitis; norovirus; hepatitis for example Hepatitis A, Hepatitis B, and Hepatitis C; and the like.

In a related embodiment of the composition, the infectious agent is at least one fungus selected from: *Cryptococcus* for example *C. Gattii* and *C. neoformans* v. *neoformans;*

Candida for example *C. albicans*; *Aspergillus* for example *A. flavus* and *A. fumigatus*; and the like.

In a related embodiment of the composition, the infectious agent is at least one protozoan selected from the group of: *Entamoeba* for example *E. histolytica*; *Giardia* for example *G. lamblia*; *Cryptosporidium* for example *C. parvum*; *Naegleria* for example *N. fowleri* and *N. gruberi*; and the like.

In a related embodiment of the composition, the allergen includes a macromolecule or portion thereof associated with an increased immunoglobulin level or allergic response in the subject, for example the allergen includes an environmental allergen, animal or plant allergen, or food allergen, for example the allergen is associated with pollen for example ragweed, dust mite proteases for example as found in dust mite excretion, fungus for example mold, pet dander or saliva, shellfish, seafood, a legume such as peanuts, and the like.

In a related embodiment of the composition, the tumor is associated with at least one cancer. For example, the cancer is a disease of: white blood cells for example a lymphocyte, skin, eye, mouth, brain, esophagus, breast, lung, liver, pancreas, stomach, colon, kidney, bladder, ovary, cervix, and vagina. For example the antigen of the tumor is at least one selected from the group of: alphafetoprotein (AFP), human epidermal growth factor receptor 2 (HER2), nestin, carcinoembryonic antigen (CEA), cancer antigen 125 (CA-125), human chorionic gonadotropin (HCG), epithelial tumor antigen (ETA), melanoma-associated antigen (MAGE), tyrosinase related protein 1 (TRP-1), G melanoma antigen (GAGE), B melanoma antigen (BAGE), cyclin-dependent kinase 4 (CDK4), and beta-catenin.

In a related embodiment, the composition is formulated to be administered by at least one route selected from: intravenous, intramuscular, intraperitoneal, intradermal, intrapulmonary, intravaginal, rectal, oral, buccal, sublingual, intranasal, intraocular, and subcutaneous.

An embodiment of the invention provides a vaccination kit that includes a unit dose of the composition according to any of embodiments herein, a container, and instructions for use.

In a related embodiment of the kit, the instructions include storage at a room temperature from about 4° C. to about 45° C. and the like. In a related embodiment, the composition is heat stable at 4° C. to about 45° C. for a period of time for example days, weeks, months, or years.

In a related embodiment, the kit further includes an applicator for the composition, for example, a spray bottle, a nasal sprayer, a fluid dropper, an oral inhaler, a nasal inhaler, or a syringe.

BRIEF DESCRIPTION OF THE DRAWINGS

FIG. 5 is a listing of the nucleotide sequence (SEQ ID No: 1) of the modified Pspac promoter for expression of antigens constitutively at a high level.

FIG. 6 shows Coomassie blue stained 4-12% SDS-PAGE (left panel), and TTFC-specific Western blot (right panel) profiles of fractionated cell extracts from BB2643 (control) and BB2646 (TTFC-expressing). Arrows indicate TTFC at the predicted molecular weight of 50 KDa.

FIG. 9 panel A is a line graph showing average serum anti-TetC antibody titers in animals administered with $10^9$ spores in control (closed squares), TTFC-associated spores at concentrations of: $10^7$ (open squares), $10^8$ (closed triangles) and $10^9$ (open triangles). The arrows indicate the time points of immunization. FIG. 9 panel B is a bar graph showing individual serum anti-TetC antibody titers in four groups of animals immunized with control and TTFC-associated spores at three concentrations $10^7$, $10^8$ and $10^9$. FIG. 9 panel C is a line graph showing mouse survival in four groups of animals challenged with $10^9$ spores in control (closed squares), TTFC-associated spores at concentrations of: $10^7$ (open squares), $10^8$ (closed triangles) and $10^9$ (open triangles). It was observed that mouse survival rate was 100% after immunization with $10^9$ TTFC associated spores.

FIG. 10 panel A is a line graph showing anti-TetC antibody titers in animals immunized with control spores (closed squares), TTFC-associated spores: not treated (open squares), treated with 37° C. for 5 weeks (closed triangles) and lyophilized (open triangles). The arrows indicate the dates of immunization. FIG. 10 panel B is a bar graph showing individual serum anti-TetC antibody titers after immunization of four groups of animals with spores stored at various conditions compared to animals immunized with control spores.

FIG. 11 panel A is a line graph showing average serum anti-TetC antibody titers in animals immunized with control spores (closed squares), TTFC-associated germinating spores (open triangles) and TTFC-associated germination deficient spores (open circles). FIG. 11 panel B is a bar graph showing individual serum anti-TetC antibody titers with germinating and germination deficient spores compared to control spores. FIG. 11 panel C is a line graph showing survival rate in challenged animals immunized with control spores (closed squares), TTFC-associated germinating spores (open triangles) and TTFC-associated germination deficient spores (open circles). It was observed that spore germination was not required for immunization.

FIG. 13 panel A shows individual serum anti-TetC antibody titers in mice after three rounds of inoculation with TTFC-associated spores before or 1-3 hours after suspension in growth medium. FIG. 13 panel B shows mouse survival levels following immunization with $10^9$ untreated dormant (bright) (closed triangles), $10^9$ dormant (bright) spores heated to 80° C. for 10 min before inoculation (open triangles), $10^9$ germinated (dark) spores after incubation for 1 h in growth medium (closed circle), $10^9$ germinated (dark) spores incubated for three hours in growth medium (closed squares) and $10^8$ germinated (dark) spores incubated for three hours in growth medium (open squares). Highest titers and greatest survival was observed in mice inoculated with $10^9$ spores incubated for three hours in growth medium. It was observed that the population of cells in this population had substantially converted to vegetative cells.

FIG. 14 panel B is a line graph showing protection against lethal tetanus toxin challenge in BALB/c mice after intranasal immunization with dried, heated B. subtilis vegetative cells expressing TTFC cytoplasmically (open circles) or control (closed squares). Each mouse was injected intraperitoneally with a dose of two $LD_{100}$ amount of tetanus toxin and was examined for symptoms during the time period indicated. Data show survival of immunized mice FIG. 15 panel A is a line graph showing serum anti-TetC antibody titers in animals immunized with TTFC-displaying spores that were either dried and heated to 60° C. for 60 min (open diamonds) or untreated (open circles) in comparison with control spores that were dried and heated (open squares). FIG. 15 panel B is a line graph showing survival rate in animals inoculated with TTFC-displaying spores that were either dried and heated 60° C. for 60 min (open diamonds) or untreated (open circles) in comparison to control spores that were dried and heated (open squares). It was observed that heating spores in the dry state did not diminish the immune response in mice.

FIG. 16 is a line graph showing development of antibody response in groups of mice inoculated with vegetative cells of strain BB3059, which contains three copies of the Pspac-tetC construct: freshly grown, unheated BB3059 vegetative cells (open squares), $4 \times 10^8$ lyophilized BB3059 cells incubated at 45° C. for 30 days (open circles), $4 \times 10^7$ lyophilized BB3059 cells at 45° C. for 30 days (gray filled circles), $4 \times 10^6$ lyophilized BB3059 cells incubated at 45° C. (black filled circles) compared to unheated, freshly grown vegetative cells of the control strain BB2643 (closed squares) and cells immunized IP with DTaP vaccine (open diamonds). Long-term heat stability of lyophilized cells of strain BB3059 incubated at 45° C. for one month was observed.

FIG. 17 panel A shows the immune response in animals immunized with CotC-TetC spores in $H_2O$ (open squares), $10^9$ lyophilized spores (open circles), $10^8$ lyophilized spores (gray filled circles), $10^7$ lyophilized spores compared to spores of the control strain BB2643 (closed squares). FIG. 17 panel B shows immune response in animals treated with CotC-TetC spores lyophilized and stored at 4° C. (open squares), $10^9$ spores lyophilized and incubated at 45° C. for one month (open circles), $10^8$ spores lyophilized and incubated at 45° C. for one month (gray filled circles) in comparison with spores of the control strain BB2643 stored in $H_2O$ at 4° C. (closed squares).

FIG. 18 is a scatter graph showing IgG1:G2a ratio observed in serum after intranasal immunization with *B. subtilis* BB3059 vegetative cells, and control i.m. injection of DTaP.

FIG. 19 is a bar graph showing IgA levels in serum and feces of mice following intranasal immunization with *B. subtilis* spores associated with bovine VP6 antigen from construct BB2666 in the presence of mLT adjuvant. The data show that immunized animals produced higher levels of IgA in feces than in serum.

FIG. 20 is a bar graph showing IgA levels following intranasal immunization of mice with *B. subtilis* spores (light gray bars) or *B. subtilis* vegetative cells (dark gray bars) associated with bovine VP6 antigen from construct BB2666. Spores and vegetative cells were administered with mLT adjuvant. The data show that animals administered spores associated VP6 produced higher levels of IgA than animals administered with vegetative cells.

FIG. 21 is a set of drawings showing a schematic growth curve of *B. subtilis* vegetative cells and initiation of sporulation after onset of growing phase. FIG. 21 panel A shows antigen display on surface of the spore. FIG. 21 panel B shows antigen displayed on the vegetative cell surface. FIG. 21 panel C shows antigen displayed in the vegetative cytoplasm.

FIG. 22 is a set of drawings showing construction of genetic fusions for antigen display. FIG. 22 panel A shows organization of a recombinant fusion of an exemplary gene CotC with TetC coding gene. FIG. 22 panel B shows organization of an exemplary gene for expressing antigen during vegetative growth.

FIG. 23 is a set of line graphs showing serum titer (ordinate, log scale) response after spore immunization with spores carrying a tetanus sequence fusion (CotC-TetC).

FIG. 23 panel A shows higher serum levels in mice immunized with $10^9$ spores of lyophilized strain BB3184 CotC-TetC fusion heated to 45° C. for 30 days (open circles) or $10^9$ spores of lyophilized strain BB3184 stored at 4° C. for 30 days (open squares) or with $10^8$ spores of lyophilized strain BB3184 TetC heated to 45° C. (closed diamonds) for 30 days compared to the control vegetative cells (closed squares). Spores of strain BB3184 heated or stored for 30 days induced antibody production.

FIG. 23 panel B shows that spores of strain BB3184 heated or stored for 90 days were immunized for anti-tetanus antibody production.

FIG. 24 is a line graph showing log of titer of antibody titer in mice that were immunized intranasally with: $10^9$ spores of strain BB3184 stored at 4° C. for 12 months (open squares), $10^9$ spores of strain BB3184 heated to 45° C. for 12 months (open circles), $10^8$ spores of strain BB3184 heated to 45° C. for 12 months (closed diamonds), or control spores (closed squares). Data show that spores heated to 45° C. for 12 months induced antibody production as well as or better than spores stored at 4° C.

FIG. 25 is a line graph showing survival of number of mice intranasally immunized with lyophilized spores and challenged with then a lethal dose of tetanus toxin. The mice were immunized intranasally with: $10^9$ spores of strain BB3184 cotC-TetC stored at 4° C. for 12 months (open squares), $10^9$ spores of strain BB3184 heated to 45° C. for 12 months (open circles), $10^8$ spores of strain BB3184 heated to 45° C. for 12 months (closed diamonds), or control spores (closed squares). Data show 100% survival of subject immunized with $10^9$ spores of strain BB3184 heated to 45° C. for 12 months or control $10^9$ spores of strain BB3184 heated to 4° C. for 12 months. Animals immunized with $10^8$ spores of strain BB3184 heated to 45° C. for 12 months resulted in 60% survival day three after challenge and 40% survival day seven after challenge. Animals administered control spores not carrying TetC did not survive beyond day 3 after challenge. The lyophilized vaccine heated to 45° C. for 12 months provided as much protective immunogenicity as that stored at 4° C.

FIG. 26 is a photograph of a Western blot showing expression of TetC in recombinant *B. subtilis* vegetative cell strains. Data show that TetC antigen was produced in large quantities in the vegetative cells (the antigen represents about three percent of the total soluble protein).

FIG. 27 is a set of photographs of a Western blot and a Coomassie blue-stained gel showing expression of TetC antigen in each of a recombinant *B. subtilis* vegetative cell strain producing toxin antigen under regulation of the IPTG-inducible Pspac, and in *B. subtilis* spores as fusion cotC-TetC. The vegetative cell and spore vaccines were incubated for at least five hours at 37° C., and samples taken during this time course were analyzed by Western blot and Coomassie.

FIG. 28 is a line graph showing log serum titer response after lyophilized vegetative cell immunization in groups of mice. The mice were immunized intranasally with: $4\times10^8$ lyophilized cells of strain BB3059 stored at 4° C. for 90 days (open squares), $4\times10^8$ lyophilized cells of strain BB3059 heated at 45° C. for 90 days (open circles), $4\times10^7$ cells of strain BB3059 heated at 45° C. for 90 days (closed circles), or control lyophilized vegetative cells not expressing TetC (closed squares). Data show that lyophilized vegetative cells of strain BB3059 stored for three months at 45° C. or 4° C. elicited the highest serum titer compared to the control vegetative cells. Thus, lyophilized vegetative cells expressing TetC stored at 4° C. for 90 days or heated to 45° C. for 90 days were comparably stable vaccines.

FIG. 29 is a set of line graphs of log serum titer response in mice immunized with lyophilized vegetative cells expressing TetC. The mice were immunized intranasally with: $4\times10^8$ cells of strain BB3059 stored at 4° C. for twelve months (open squares), $4\times10^8$ cells of strain BB3059 heated to 45° C. for twelve months (open circles), $4\times10^7$ cells of strain BB3059 heated at 45° C. for twelve months (open diamonds), or control lyophilized vegetative cells not expressing TetC (closed squares). The serum was assayed for titer of anti-tetanus toxin.

FIG. 29 panel A shows that $4\times10^8$ cells of lyophilized vegetative cells of strain BB3059 stored at 4° C. and heated at 45° C. for twelve months had a higher serum titer than that induced with $4\times10^7$ lyophilized vegetative cells of strain BB3059 heated to 45° C. for twelve months and the control lyophilized vegetative cells. Thus the lyophilized vegetative cells of strain BB3059 were stable as vaccines when stored at 4° C. or heated at 45° C. for 12 months.

Figure 29:
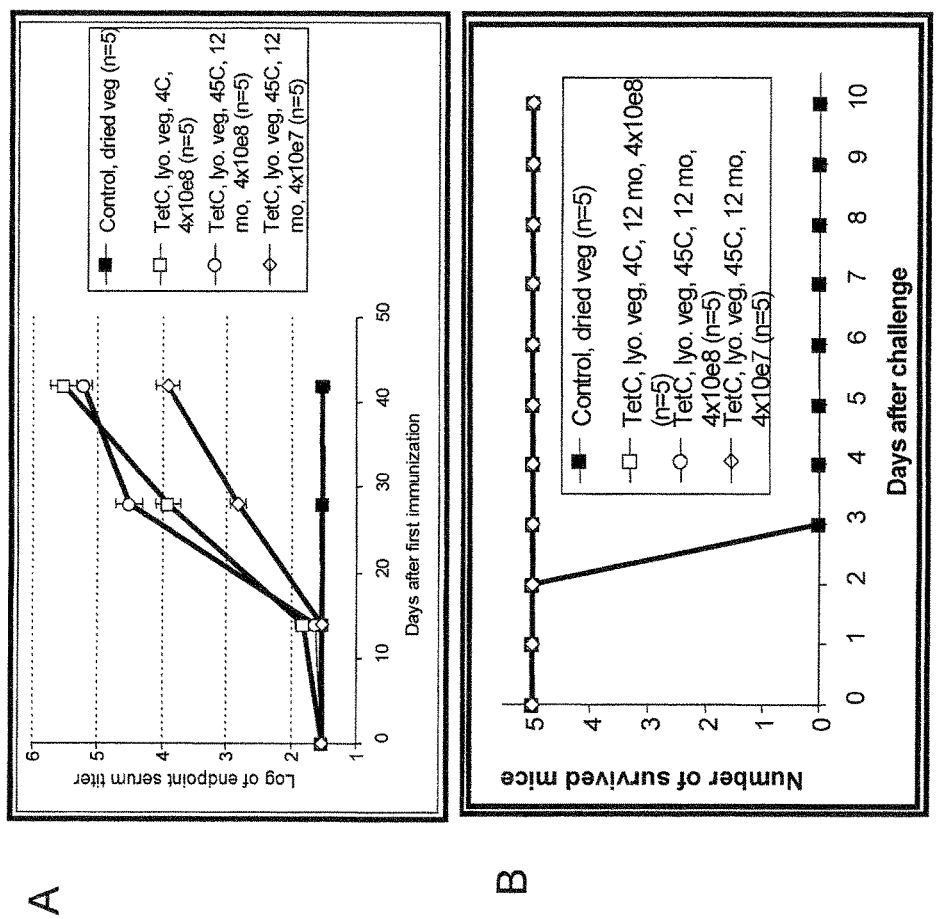

FIG. 29 panel B shows 100% survival rates for subjects immunized with TetC expressing lyophilized vegetative cells of strain BB3059, and zero survival rate days for animals immunized with control cells.

FIG. 30 is a set of line graphs showing serum titer response for mice inoculated intranasally (IN) or sublingually (SL) with lyophilized *B. subtilis* vegetative cells of strain BB3059 expressing TetC that were lyophilized and heated at 45° C. for 17 months. Mice were immunized: intranasally with lyophilized vegetative cells of strain BB3059 heated at 45° C. for 17 months (open squares), sublingually with control lyophilized vegetative cells heated at 45° C. for 17 months (open triangles), or intranasally with control lyophilized vegetative cells of strain BB3059 (closed circles).

FIG. 30 panel A shows that the average serum titer data of mice immunized intranasally with lyophilized vegetative cells of strain BB3059 produced higher serum titer than mice immunized sublingually with lyophilized vegetative cells of strain BB3059 or control lyophilized vegetative cells of strain BB2643. Thus, lyophilized vegetative cells of strain BB3059 expressing TetC were heat stable for 17 months, and capable of eliciting anti-TetC antibodies following IN or SL administration.

FIG. 30 panel B shows individual animal serum titer data including that the animals immunized intranasally (IN) or sublingually (SL) with lyophilized *B. subtilis* vegetative cells of strain BB3059 expressing TetC. Higher serum titer values were obtained in individual mice that were intranasally immunized compared to individual mice sublingually immunized.

FIG. 31 is a chart showing an intranasal vaccination chart and schedule for normal mice and SCID immune deficient/human immune system mice.

FIG. 32 is a set of line graphs showing body weight (grains, g; ordinate) of inoculated mice as a function of time (days, abscissa) after inoculation with *Bacillus* lyophilized cells of strain 49NA2 (open triangles) or with spores of strain 49NB3 (open squares).

FIG. 32 panel A shows that body weight of normal Balb/cByJ mice increased as a function of time (32 days).

FIG. 32 panel B shows that body weight of SCID CBySmn.CB17-Prkdcsid/J mice increased as a function of time (32 days).

FIG. 33 is a set of line graphs showing serum titer response and number of surviving mice (survival). The animals were sublingually (SL) immunized with lyophilized *B. subtilis* vegetative cells strain BB3059 with or without mutated *E. coli* heat labile enterotoxin (mLT) adjuvant, then challenged with a lethal dose of tetanus toxin.

FIG. 33 panel A is a line graph showing average serum anti-TetC antibody titers for immunized animals. The animals were immunized: sublingually with: lyophilized *B. subtilis* vegetative cells strain BB3059 TetC (closed circles), lyophilized *B. subtilis* vegetative cells BB3059 TetC and mLT adjuvant (closed squares); control lyophilized *B. subtilis* vegetative cells (open triangles), or control lyophilized *B. subtilis* vegetative cells and mLT adjuvant (open diamonds). Data show that animals sublingually immunized with lyophilized *B. subtilis* vegetative cells BB3059 expressing TetC (70B BB3059 SL Veg cells) showed greater serum antibody titer than animals administered control lyophilized vegetative cells, regardless of presence of mLT adjuvant FIG. 33 panel B is a line graph showing mouse survival rate following challenge with lethal tetanus toxin of mice immunized sublingually with: control lyophilized vegetative cells (open triangles), lyophilized *B. subtilis* vegetative cells BB3059 expressing TetC (closed circles), or lyophilized *B. subtilis* vegetative cells BB3059 expressing TetC, and mLT adjuvant (closed squares). Data show 100% survival rates through day 10 for animals immunized with TetC expressing lyophilized vegetative cells of strain BB3059, and 40% survival rate through day ten after challenge of animals immunized with TetC expressing lyophilized vegetative cells of strain BB3059 and mLT adjuvant. Control lyophilized vegetative cells provided no immunity.

FIG. 34 is a set of line graphs showing serum titer response and survival rate to lethal tetanus toxin challenge following sublingual immunization with lyophilized *B. subtilis* vegetative cells compared to purified recombinant TetC.

FIG. 34 panel A shows average serum anti-TetC antibody titers in animals immunized: sublingually with lyophilized *B. subtilis* vegetative cells BB3059 expressing TetC (open squares); intranasally with lyophilized *B. subtilis* vegetative cells BB3059 expressing TetC (open diamonds); sublingually with purified recombinant TetC (open triangles); or sublingually with control lyophilized *B. subtilis* vegetative cells (closed circles). Animals immunized intranasally with lyophilized *B. subtilis* vegetative cells BB3059 expressing TetC, animals immunized sublingually with either lyophilized *B. subtilis* vegetative cells BB3059 expressing TetC, and animals immunized with recombinant TetC all produced comparably high levels of anti-TetC antibody.

FIG. 34 panel B is a line graph showing mouse survival rate (%; ordinate) as a function of time (days; abscissa) for mice challenged with lethal tetanus toxin and previously immunized: sublingually with lyophilized *B. subtilis* vegetative cells BB3059 expressing TetC (open squares); intranasally with lyophilized *B. subtilis* vegetative cells BB3059 expressing TetC (open diamonds); sublingually with purified recombinant TetC (open triangles); or sublingually with control lyophilized *B. subtilis* vegetative cells (closed circles). Data show 100% survival of animals immunized either intranasally or sublingually with lyophilized *B. subtilis* vegetative cells BB3059 expressing TetC, compared to a 80% survival rate for animals immunized sublingually with recombinant TetC, and no survival for animals immunized with control lyophilized vegetative cells.

FIG. 35 is a set of bar graphs showing serum IgG1 levels (open bars; abscissa) and IgG2a levels (closed bars; abscissa) in mice following sublingual immunization with lyophilized *B. subtilis* vegetative cells BB3059 expressing TetC (TetC veg Cells, SL); intranasal immunization with lyophilized *B. subtilis* BB3059 expressing TetC (TetC veg Cells, IN); sublingual immunization with purified recombinant TetC (rTTC, SL); or intramuscular immunization with a commercial vaccine for diphtheria, tetanus and pertussis (DTAP, IM; Tripedia®, Sanofi Pasteur Inc., Swiftwater, Pa., USA). Each animal showed greater IgG1 levels compared to IgG2a levels. Sublingual or intranasal immunizations of animals with lyophilized *B. subtilis* BB3059 TetC resulted in more similar TetC-specific IgG1 and IgG2a antibody production compared to the recombinant TetC or commercially available DTAP vaccine.

FIG. 36 is a set of bar graphs showing mouse serum concentrations of cytokines (ng/mL; ordinate) two weeks following a third immunization (abscissa). Mice were immunized sublingually with lyophilized *B. subtilis* vegetative cells BB3059 expressing TetC (TetC veg cells, SL); intranasally with lyophilized *B. subtilis* vegetative cells BB3059 expressing TetC (TetC veg cells, IN); sublingually with purified recombinant TetC (rTTC); or intramuscularly with commercial DTAP vaccine (DTAP).

FIG. 36 panel A shows substantial interleukin-2 (IL-2) in serum of animals sublingually or intranasally immunized with lyophilized *B. subtilis* vegetative cells BB3059, comparable to animals immunized sublingually with either purified recombinant TetC and or DTAP vaccine.

FIG. 36 panel B shows greater interferon-gamma (IFNγ) serum concentrations in serum of animals sublingually immunized with lyophilized *B. subtilis* vegetative cells BB3059 expressing TetC compared to animals immunized intranasally with lyophilized *B. subtilis* vegetative cells BB3059 expressing TetC, sublingually with purified recombinant TetC, or intramuscularly with DTAP vaccine.

FIG. 36 panel C shows greater interleukin-4 (IL-4) serum concentrations in serum of animals intranasally immunized with lyophilized *B. subtilis* vegetative cells BB3059 expressing TetC than animals immunized intramuscularly with DTAP vaccine, or sublingually immunized with either lyophilized *B. subtilis* vegetative cells BB3059 expressing TetC or purified recombinant TetC.

FIG. 36 panel D shows comparable levels of serum interleukin-10 (IL-10) in animals immunized sublingually with purified recombinant TetC, and animals sublingually, intranasally immunized with lyophilized *B. subtilis* vegetative cells BB3059 and animals immunized sublingually with DTAP vaccine.

FIG. 37 is a set of bar graphs showing amount of fecal immunoglobulin in mice immunized sublingually with control lyophilized vegetative cells (Ctl veg cells SL), sublingually with lyophilized *B. subtilis* vegetative cells BB3059 expressing TetC (TetC veg cells, SL), intranasally with lyophilized *B. subtilis* vegetative cells BB3059 expressing TetC (TetC veg cells, IN), or intramuscularly with commercial DTAP vaccine (DTAP, IM).

FIG. 37 panel A shows high IgG fecal content in mice inoculated sublingually with lyophilized *B. subtilis* vegetative cells of strain BB3059 expressing TetC, mice inoculated intramuscularly with commercial DTAP vaccine or mice inoculated sublingually with lyophilized *B. subtilis* vegetative cells of strain BB3059 expressing TetC compared to IgG fecal content in mice inoculated sublingually with control lyophilized *B. subtilis* vegetative cells.

FIG. 37 panel B shows high IgA fecal content in mice inoculated intranasally with lyophilized *B. subtilis* vegetative cells BB3059 expressing TetC, mice inoculated sublingually with lyophilized *B. subtilis* vegetative cells BB3059 expressing TetC compared to IgA fecal content in mice inoculated with control lyophilized *B. subtilis* vegetative cells and commercial DTAP vaccine.

FIG. 38 is a set of bar graphs showing amount of TetC specific IgA detected by ELISA in vaginal and saliva samples of mice immunized: sublingually with lyophilized *B. subtilis* vegetative cells BB3059 expressing TetC (open), intranasally with lyophilized *B. subtilis* vegetative cells of strain BB3059 expressing TetC (diagonal), sublingually with purified recombinant TetC (checkered), or intramuscularly with commercial DTAP vaccine (closed). Data show higher amounts of TetC specific IgA detected in the vaginal samples compared to the in saliva samples, and highest amounts in animals inoculated sublingually with lyophilized *B. subtilis* vegetative cells of strain BB3059 expressing TetC, compared to intranasally, and in mice inoculated sublingually with purified recombinant TetC, or intramuscularly with commercial DTAP vaccine.

FIG. 39 is a set of representative photomicrographs showing MHC class II deposition of murine spleen tissue (panels A and B respectively), and murine intestinal tract tissue (panels C and D) in animals sacrificed 24 hours after immunization. The animals were sublingually immunized with either lyophilized *B. subtilis* vegetative cells BB3059 expressing TetC (panels A and C) or with control lyophilized *B. subtilis* vegetative cells (panels B and D).

FIG. 39 panels A and C show MHC class II deposition on murine spleen tissue and murine intestinal tract tissue, respectively, from mice sublingually immunized with lyophilized *B. subtilis* vegetative cells BB3059 expressing TetC. Extensive MAC immunostaining with various patterns of staining of spleen cells was observed.

FIG. 39 panels B and D show MHC class II deposition on murine spleen tissue and murine intestinal tract tissue, respectively, from mice sublingually immunized with control lyophilized *B. subtilis* vegetative cells. Little or no MHC class II immunostaining of cells was observed on the murine intestinal tract tissue.

FIG. 40 is a bar graph showing anti-LT specific IgA and IgG immunoglobulin levels (absorbance at 450 nm; ordinate) in serum, fecal and saliva samples of piglets (abscissa) 14 days after a fourth sublingual immunization with lyophilized *B. subtilis* vegetative cells with (open bars) or without mLT adjuvant (closed bars). Animals administered mLT adjuvant received 25 μg of the mLT adjuvant per inoculation. The data show that in each of the serum, fecal, and saliva samples animals administered lyophilized *B. subtilis* vegetative cells with mLT adjuvant produced higher levels of IgG and IgA than animals administered control lyophilized vegetative cells only.

FIG. 41 is a set of bar graphs showing anti-mLT IgA and IgG immunoglobulin titer in murine serum samples and fecal samples 14 days after a third immunization or fourth immunization of animals. The animals were immunized sublingually with lyophilized *B. subtilis* vegetative cells and 5 μg of mLT adjuvant (LT 5+veg cells, SL; closed bars), or intranasally with lyophilized *B. subtilis* vegetative cells and 10 μg of mLT adjuvant (LT 10+veg cells, IN; open bars).

FIG. 41 panel A shows that serum anti-mLT IgG was higher than anti-mLT IgA for both sublingual and intranasal immunization. The ratios of sublingual IgG levels and intranasal IgG levels were comparable.

FIG. 41 panel B shows that fecal anti-mLT IgA amounts was higher than anti-mLT IgG for both sublingual and intranasal immunization.

FIG. 42 is a line graph showing log of serum titers for piglets immunized sublingually with lyophilized *B. subtilis* vegetative cells BB3059 TetC (open squares); sublingually with lyophilized *B. subtilis* vegetative cells BB3059 TetC and mLT adjuvant (open triangles); orally with lyophilized *B. subtilis* vegetative cells BB3059 expressing TetC (open circles); or sublingually with control lyophilized *B. subtilis* vegetative cells (closed diamonds). Animals immunized sublingually with lyophilized *B. subtilis* vegetative cells BB3059 expressing TetC with or without mLT adjuvant showed greater serum anti-TetC antibody titer than animals immunized orally with either lyophilized *B. subtilis* vegetative cells BB3059 expressing TetC, or control lyophilized vegetative cells. Control lyophilized vegetative cells did induce antibody.

FIG. 43 is a line graph showing log of serum titer (ordinate) as a function of time (abscissa) in mice immunized with dried lyophilized vegetative cell vaccine expressing TetC according to immunization schedules: biweekly (closed circles), monthly (open circles), or bimonthtly (closed triangle). The data show successful similar endpoints of high titer, with optimal antibody production at biweekly or monthly schedules.

DETAILED DESCRIPTION

Infectious diseases remain a public health problem, in spite of the progress in antibiotic and anti-viral chemotherapeutic agents. A class of viral diseases referred to as emerging diseases and exemplified by SARS and avian and/or swine influenza, have been causally associated with increased contact between wild animals that migrate, such as ducks and geese, with intensely farmed agricultural animals such as pigs, and from rapid global travel.

Spore-foaming microorganisms offer the possibilities of new classes of vectors for administering one or more antigens of an infectious virus, in order to immunize human or animal subjects. Great variety in choice of types of host cells enables the designer of the vaccine to use a cell genotype that results in a single round of immunization, for example in human subjects, by using chromosomal markers that allow growth only under highly restricted conditions, or by using a cell genotype chosen to allow transmission from subject to subject, such as in a bird population.

Most important, because bacterial and fungal spores remain viable under a very wide range of ambient environmental conditions, a spore-based vaccine offers the possibility of storage at room temperatures rather than under refrigeration or freezing. See Acheson et al., U.S. Pat. No. 5,800,821, issued Sep. 1, 1998, and incorporated herein by reference in its entirety.

Spores of bacterial genera within the group of streptomycetes are sufficiently heat resistant to survive extreme fluctuations of room temperature, for example substantial quantitative survival for at least a few minutes at 50° C. Strains of the yeast *Saccharomyces*, a fungus that produces ascospores, are resistant to several minutes of heat at 60° C. See, Put et al., 1982, J. Appl. Bact. 52: 235-243. Similarly, spores of non-toxic strains of fungi, such as *Penicillium* strains that are well known edible components of cheese (Roquefort, gorgonzola, etc.) and produce spores that may be used. Heat resistance for 10 minutes at 50° C. was observed with spores from a variety of species of the fungus *Aspergillus* (Pitt et al., 1970, Appl Microbiol. 20(5): 682-686). Genetics and recombinant techniques for many strains and species of both streptomycetes and fungi are well developed. See Hopwood et al., *Streptomyces*, 1985, publ. John Innes Press; Kieser et al., Practical *Streptomyces* Genetics, 2008, publ. John Innes Press.

However these spores are not so resistant to extreme conditions as are the spores of *Bacillus* strains (which survive quantitatively even at such extreme conditions as boiling, and have been recovered as viable colony forming units from insects preserved for millions of years in amber; Cano et al., 1995, Science 268:1060-1064). The methods herein are suitable for use with spores of bacteria or fungi capable of withstanding ambient conditions of storage at room temperature.

The use of *B. subtilis* as a vehicle for vaccine antigen delivery is a promising new approach to mucosal immunization (Duc et al., 2003, Infect. Immun. 71: 2810-2818; Oggioni et al., 2003, Vaccine 21 Suppl. 2: S96-101). The primary model used to date has been the spore form of *B. subtilis* displaying tetanus toxin antigen on its surface. An advantage of using spores as vectors is that the spores are highly resistant to environmental stresses such as extremes of heat, pH, desiccation, freezing and thawing, and radiation (Nicholson et al., 2000, Microbiol. Mol. Biol. Rev. 64(3): 548-557). Heterologous antigens displayed on the spore surface as a fusion product with spore coat proteins have been shown to elicit protective immune responses to tetanus toxin when spores displaying tetanus toxin fragment C (TTFC) were given either orally or intranasally (Due et al., 2003, Infect. Immun. 71: 2810-2818). For oral immunization, several rounds of high doses of spores ($\geq 10^{10}$) were necessary and the long-term immunogenic stability of these preparations has not been rigorously tested. Moreover, the exposure of the antigen to proteases in the GI tract may reduce the availability of immunogenic protein to the GI immune system (Duc et al. 2003).

Orally administered spores of *B. subtilis* survive passage through the gastrointestinal tract of mice and may germinate in the intestines to yield replicative vegetative cells; the intestinal tract becomes briefly colonized (Spinosa et al., 2000, Res. Microbiol. 151: 361-368; Casula et al., 2002, Appl. Environ. Microbiol. 68: 2344-2352). If spores were designed to generate antigen only after germination in the intestinal tract, such a spore-based vaccine would address the issues of antigen degradation during storage and during passage through the GI tract and would potentially be stable indefinitely. The *B. subtilis* spore-based vaccine induces a serum antibody response to *Yersinia pseudotuberculosis* invasin by spores engineered to display invasin on the vegetative cell surface after germination and outgrowth (Acheson et al., U.S. Pat. No. 5,800,821, issued Sep. 1, 1998). Oral inoculation with *B. subtilis* spores engineered to express TTFC after germination in the vegetative cell cytoplasm was shown to induce protective antibodies (Uyen et al., 2007, Vaccine 25(2): 356-365). It is not known how well engineered strains of *B. subtilis* colonize the intestine of humans or if there would be interference of colonization from other intestinal micoflora.

Because of the lack of immune responses found by some to live bacterial vectors given orally, another approach to mucosal immunization is the intranasal route. Attenuated *Salmonella typhi* expressing TTFC elicited protective immunity to tetanus toxin after the vaccine was administered intranasally, but not orally (Galen et al., 1997, Vaccine 15(6-7): 700-708). Use of attenuated pathogenic bacteria as vectors has the general disadvantage that sufficient attenuation of virulence is required to assure safety. For this reason, bacteria that are generally regarded as safe are preferable. For instance, *Lactobacillus plantarum* expressing TTFC was shown to protect against tetanus toxin challenge after intranasal administration (Grangette et al., 2001, Infect. Immun. 69(3):1547-1553). Like lactobacilli, *B. subtilis* is also generally regarded as safe, and is neither pathogenic nor toxigenic to humans, animals, or plants (Sonenshein et al 1993). *B. subtilis* has been extensively studied as a model gram-positive bacterium, and is advantageous for genetic manipulation. Stable genetically engineered constructs can be integrated into the bacterial chromosome, making it a good candidate for vaccine preparation.

Bacterial genera such as *Bacillus* and others that produce spores, and fungal species are within the scope of embodiments of the methods and compositions herein, if they satisfy criteria of suitability for engineering vaccines, viz., production of stable spores, and non-toxicity to animals of spores and vegetative cells. For example, cells of non-toxic streptomycete strains such as *Streptomyces lividans*, *S. coelicolor*, and *S. reticuli* may be engineered by conventional genetic techniques to express cytoplasmically an antigen encoded by the genome of an infectious agent, such that the antigen is synthesized in soluble form, during vegetative growth of the cells. The antigen while made as a soluble material becomes associated with spores during the sporulation process. The spores are prepared by conventional techniques into a vaccine composition, and when administered to a subject results in an immune response capable of protecting the subject from infection by the infectious agent that is the source of the antigen.

Compositions including *Bacillus* spores and vegetative cells expressing antigen are administered to the subject, for example by contacting the mucosal tissues. Mucosal tissues or mucosae or mucosal cells are epithelial linings of tissue that function to modulate absorption into and secretion from of nutrients and signaling macromolecules to and from underlying organs and tissues. Mucosal tissues are found for example lining nose, throat, mouth, eye, eyelid, esophagus, female genitalia, male genitalia, anus, urinary tract, and digestive tract.

The term, "antigen" as used herein and in the claims refers to a protein or a portion of a protein, isolated from nature or synthesized, or expressed in and purified from a recombinant cell, or a peptide, or a derivatized version thereof containing one or a few additional amino acids, including sequences of amino acids that are of biological origin, or are not found in nature. The antigen is a peptide of sufficient length to provoke an immune response in an animal having an immune system, generally at least about 4 to 7 amino acids in length.

The term "derivative" as used herein and in the claims may be a protein, peptide, or chemically related foam of that protein having an additional substituent on an amino acid, for example, N-carboxyanhydride group, a γ-benzyl group, an ϵ,N-trifluoroacetyl group, or a halide group attached to an atom of the amino acid of a protein.

The term, "immune response" means any natural function of an immune system, and includes without limitation, any cellular function or organ function characteristic of ability to distinguish a component of self and non-self by an organism, for example, ability to bind to an MHC class I or class II protein, or ability to bind to a cell having such proteins, ability to activate killer T cells, or to elicit production of antibodies of any type are all within the definition.

Immunizations have been well-known in the medical arts since discovery of cowpox vaccination over two hundred years ago, and include injection by a variety of routes including subcutaneous, and oral delivery, e.g., of Sabin polio vaccine. Discovery herein of efficiency of a spore-based vaccine delivered by an intranasal route is an important and surprising result.

The term, "associated" as used herein and in the claims refers to the physical relationship of an antigen to a spore, or a vegetative cell or portion thereof. During sporulation, the antigen is produced during vegetative phase of cell growth and is physically associated with the spore. The antigen may be displayed on the spore's surface, or may be entrained within the spore coat, and the ability of the spores or vegetative cells or portions thereof to elicit an immune response does not depend on any particular physical location of the antigen within the spore or cell, nor any mechanism of packaging. In contrast to embodiments of the methods and compositions herein, in which the antigen is associated with spores and is not necessarily covalently bound to any particular spore component, Acheson et al., issued Sep. 1, 1998, U.S. Pat. No. 5,800,821 shows a vaccine using spores engineered by genetically manipulating spore-forming bacterial cells to contain a certain DNA sequence encoding an antigen, producing spores produced as a genetic fusion to spore surface proteins during the sporulation phase in the cells.

The term, "adjuvant" as used herein and in the claims refers to any compound which when administered together with an antigen nonspecifically enhances the immune response to that antigen. Adjuvants may be insoluble and undegradable substances (e.g., inorganic gels such as aluminum hydroxide), or water-in-oil emulsions such as incomplete Freund's adjuvant. Generally, adjuvants retard the destruction of antigen and allow the persistence of low but effective levels of antigen in the tissues and also nonspecifically activate the lymphoid system by provoking an inflammatory response. One of the most effective adjuvants is Freund's complete adjuvant having mycobacteria suspended in a water-in-oil emulsion, however the intense inflammatory response it provokes precludes its clinical use. Examples herein show enhanced immune responses with several adjuvants including cholera toxin and a non-toxic *Escherichia coli* heat-labile enterotoxin variant, which are administered with spores.

Both cholera toxin produced by *Vibrio cholerae* and *Escherichia coli* heat labile enterotoxin have been widely used as adjuvants in experimental systems, and each induces significant antibody responses to adjuvants and are also potent mucosal adjuvants for co-administrated, unrelated antigens, especially when give by the oral route. Cholera toxin functions as an adjuvant by inducing antigen specific $CD4^+$ T cells to secrete interleukin 4 (IL-4), IL-5, IL-6, and IL-10. Heat labile enterotoxin produced by some enterotoxigenic strains of *Escherichia coli* functions as an adjuvant by inducing Th1 and Th2 cytokine responses. Both cholera toxin produced by *Vibrio cholerae* and heat labile enterotoxin produced by *Escherichia coli* are multi-subunit macromolecules composed of two structurally, functionally, and immunologically separate A and B subunits (Yamamoto et al., 1997, Proc. Natl. Acad. Sci. USA 94(10): 5267-5272).

The term "thermally-stable" as used herein and in the claims relates to an enhanced persistence of an active substance or pharmaceutical product as a function of time under the influence of a variety of environmental factors, primarily temperature, and is also affected by other conditions such as humidity and light in comparison with a control preparation that is not thermally stable. In making this determination, product-related factors also influence the stability, e.g., the chemical and physical properties of the active substance and the pharmaceutical excipients, the dosage form and its composition, the manufacturing process, the nature of the container-closure system, and the properties of the packaging materials. Also, the stability of excipients that may contain or form reactive degradation products are considered.

Stress testing of the active substance is used to identify the potential degradation products, and to establish degradation pathways and stability of the molecule. The nature of the stress testing depends on the individual active substance and the type of pharmaceutical product involved.

In general, an active substance is evaluated under storage conditions (with appropriate tolerances) that test thermal stability and, if applicable, sensitivity to moisture. The storage conditions and the lengths of time period for study are appropriate to consider storage, shipment, and subsequent use appropriate to the climatic zone or zones in which the active substance is likely intended to be stored. Long-term testing extends for a period about a month, or, about three months, about six months, or about twelve months.

Testing includes a number of product batches in conditions of packaging and temperatures that are representative of the product's intended use.

Data from an "accelerated" storage condition, if appropriate, are obtained to test the product at conditions beyond those intended, i.e., excessively high or low temperatures compared to potential actual ambient conditions. An accelerated storage condition includes tests of conditions that mimic handling issues such as prolonged exposure to excess moisture and variable volume delivery of a composition including the active substance. Calculations of the data obtained under accelerated conditions are then used to extrapolate the presumed stability of the product in normal environments and conditions, although these calculations are an estimate of stability of the product under normal conditions. Data obtained from accelerated storage conditions are combined with other data including long-term testing described above to determine the stability of the product.

U.S. Pat. No. 6,187,319 (Herrmann et al., issued Feb. 13, 2001) describes a method of producing an immune response in an animal to a rotavirus antigen, by administering an isolated rotavirus VP6 polypeptide of a different strain of rotavirus to produce an effective immune response. The VP6 polypeptide was delivered directly, or by using a DNA plasmid or a virus to express the polypeptide in the recipient, with transcriptional and translational regulatory sequences encoded by the plasmid or virus. U.S. Pat. No. 6,165,993 (Herrmann et al., issued Dec. 26, 2000) describes a method of eliciting an immune response or protective immunity with a vaccine having DNA encoding an antigen (e.g., capsid proteins or polypeptides of a rotavirus such as VP4, VP6 and VP7), the antigen encoded by a nucleotide sequence in a plasmid vector.

A feature provided by the present invention herein is a method of immunizing a subject to an infectious agent, the method including steps of: sporulating a vegetative host bacterial cell which contains an isolated nucleotide sequence encoding an antigen of the infectious agent, such that the nucleotide sequence is operably linked to a promoter for cytoplasmic vegetative expression of the antigen, such that the spores are associated with the antigen and, contacting the subject with a composition including the spores, such that the antigen immunizes the subject to the infectious agent. In general, the infectious agent is viral or bacterial. For example, the infectious agent is at least one bacterium selected from the group of consisting of *Bacillus anthracis, Clostridium tetani, Corynebacterium diphtheriae, Bordetella pertussis, Mycobacterium tuberculosis, Salmonella typhimurium, Staphylococcus aureus, Streptococcus pneumoniae, Treponema pallidum, Neisseria gonorrhoeae*, and the like. For example, the infectious agent is at least one virus selected from the group consisting of human immunodeficiency virus (HIV), influenza, polio, herpes, smallpox, measles, mumps, rubella, rotavirus, chicken pox, rabies, West Nile virus, eastern equine encephalitis, norovirus, and the like. An exemplary antigen is a rotavirus antigen.

The method in related embodiments further includes prior to sporulating, obtaining the isolated nucleotide sequence encoding the rotavirus antigen from a rotavirus strain that is bovine or murine. For example, the rotavirus antigen is a viral virion protein, for example, the viral virion protein is selected from at least one of the group consisting of VP2, VP4, VP6, VP7, NSP4, and a portion or a derivative thereof.

In general, the subject is a vertebrate animal. For example, the vertebrate animal is from at least one of the group of an agricultural animal, a high value zoo animal, a research animal, a human, and a wild animal found in a densely populated human environment such as a wild bird.

The method in related embodiments further includes contacting the subject by administering the composition by a route selected from at least one of intravenous, intramuscular, intraperitoneal, intradermal, mucosal, and subcutaneous routes. For example, contacting the subject is by intranasal administration. For example, the intranasal administration includes inhalation or nose drops. Inhalation methods include use of a nebulizer or an atomizer, and include a measured dose.

In general, the vegetative host bacterial cell is a *Bacillus* cell. For example, the *Bacillus* is *Bacillus subtilis*, although other species of bacilli and other spore-forming organisms are also within the scope of the methods herein.

The composition used in the method herein includes in related embodiments an adjuvant, for example, the adjuvant is selected from at least one of the group consisting of cholera toxin, a non-toxic variant of *Escherichia coli* labile toxin, and a portion or a derivative thereof.

The method according to related embodiments further involves observing resistance of the composition to at least one condition selected from the group of heat, drying, freezing, deleterious chemicals and radiation.

An embodiment of the method further involves measuring an antibody titer in serum of an infected subject, such that increase in antibody for the antigen in comparison to a control serum is an indication of efficacy of the immunogenicity of the composition. Suitable control sera include pre-immune serum from the subject, or serum from a different subject receiving a different antigen. Still another feature of the invention provided herein is measuring an amount of viral shedding in the subject afflicted by the infectious agent, such that a decrease in fecal virus compared to that in a control subject also afflicted by the infectious agent and not contacted with the composition, is a measure of efficacy of the immunogenicity of the composition.

A featured embodiment of the invention provided herein is a thermally-stable vaccine composition for immunizing a subject with an antigen from an infectious agent, the composition including spores from a *Bacillus* cell that contains an isolated nucleotide sequence encoding the antigen, the nucleotide sequence being genetically engineered and having been integrated into the host bacterial chromosome or carried on a plasmid and provided with appropriate transcriptional and translational regulatory sequences, such that the cell expresses the antigen cytoplasmically as a soluble component during vegetative growth, and upon sporulation by the cell, the antigen is associated with the spores, and the composition comprising the spores is effective to immunize the subject. For example, the antigen is a viral protein or a portion or a derivative thereof. For example, the viral protein is a viral virion protein. For example, the viral virion protein is selected from at least one of the group consisting of VP2, VP4, VP6, VP7, NSP4, and a portion or a derivative thereof. An exemplary, *Bacillus* is *Bacillus subtilis*.

The composition in related embodiments includes an adjuvant. For example, the adjuvant is selected from at least one of the group consisting of cholera toxin, a non-toxic variant of *Escherichia coli* labile toxin, and a portion or a derivative thereof.

In related embodiment of the composition, the isolated nucleotide sequence encoding the antigen is from a strain that is bovine or murine.

The invention herein also features a vaccination kit that includes a unit dose of the composition according to any of the above embodiments, a container, and instructions for use. In related embodiments, the instructions include storage at a room temperature of from about 4° C. to about 45° C. and the like (calculation of 45° C. is that this temperature is the same as 113° F.).

Pharmaceutical Compositions

An aspect of the present invention provides pharmaceutical compositions, wherein these compositions comprise spores associated with an antigen from an infectious agent, and optionally further include an adjuvant, and optionally further include a pharmaceutically acceptable carrier.

In certain embodiments, these compositions optionally further comprise one or more additional therapeutic agents. In certain embodiments, the additional therapeutic agent or agents are selected from the group consisting of growth factors, anti-inflammatory agents, vasopressor agents, collagenase inhibitors, topical steroids, matrix metalloproteinase inhibitors, ascorbates, angiotensin II, angiotensin III, calreticulin, tetracyclines, fibronectin, collagen, thrombospondin, transforming growth factors (TGF), keratinocyte growth factor (KGF), fibroblast growth factor (FGF), insulin-like growth factors (IGF), epidermal growth factor (EGF), platelet derived growth factor (PDGF), neu differentiation factor (NDF), hepatocyte growth factor (HGF), and hyaluronic acid.

As used herein, the term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences Ed. by Gennaro, Mack Publishing, Easton, Pa., 1995 discloses various carriers used in formulating pharmaceutical compositions and known techniques for the preparation thereof. Carriers are selected to prolong dwell time for example following inhalation or other form of intranasal administration, or other route of administration.

Some examples of materials which can serve as pharmaceutically acceptable carriers include, but are not limited to, sugars such as glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, according to the methods of treatment of the present invention, the immunization is promoted by contacting the animal with a pharmaceutical composition, as described herein. Thus, the invention provides methods for immunization comprising administering a therapeutically effective amount of a pharmaceutical composition comprising active agents that include a spore preparation having an associated antigen from an infectious agent, to a subject in need thereof, in such amounts and for such time as is necessary to achieve the desired result. It will be appreciated that this encompasses administering an inventive vaccine as described herein, as a preventive or therapeutic measure to promote immunity to the infectious agent, to minimize complications associated with the slow development of immunity (especially in compromised patients such as those who are nutritionally challenged, or at risk patients such as the elderly or infants).

In certain embodiments of the present invention a "therapeutically effective amount" of the pharmaceutical composition is that amount effective for promoting appearance of antibodies in serum specific for the chosen antigen, or disappearance of disease symptoms, such as amount of virus in feces or in bodily fluids or in other secreted products. The compositions, according to the method of the present invention, may be administered using any amount and any route of administration effective for generating an antibody response. Thus, the expression "amount effective for promoting immunity", as used herein, refers to a sufficient amount of composition to result in antibody production or remediation of a disease symptom.

The exact dosage is chosen by the individual physician in view of the patient to be treated. Dosage and administration are adjusted to provide sufficient levels of the active agent(s) or to maintain the desired effect. Additional factors which may be taken into account include the severity of the disease state, e.g., exposure to infectious agent in the past or potential future exposure, or exposure to a seasonal allergen; age, weight and gender of the patient; diet, time and frequency of administration; drug combinations; reaction sensitivities; and tolerance/response to therapy. Long acting pharmaceutical compositions might be administered every 3 to 4 days, every week, or once every two weeks depending on half-life and clearance rate of the particular composition.

The active agents of the invention are preferably formulated in dosage unit form for ease of administration and uniformity of dosage. The expression "dosage unit form" as used herein refers to a physically discrete unit of active agent appropriate for one dose to be administered to the patient to be treated. It will be understood, however, that the total daily usage of the compositions of the present invention will be decided by the attending physician within the scope of sound medical judgment. For any active agent, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of active agent which ameliorates at least one symptom or condition. Therapeutic efficacy and toxicity of active agents can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use.

The therapeutic dose shown in examples herein is at least about $10^8$, about $3\times10^8$, about $10^9$, or at least about $3\times10^9$ spores/dose/animal. As bacterial spores are readily produced and are inexpensively engineered and designed and stored, greater doses for large animals are economically feasible. For an animal several orders of magnitude larger than experimental animals used in examples herein, the dose is easily adjusted, for example, to about $3\times10^{10}$, about $3\times10^{11}$, to $3\times10^{12}$ or about $3\times10^{13}$, for animals such as humans and small agricultural animals. However doses of about $3\times10^{14}$, $3\times10^{15}$, or even about $3\times10^{16}$, or about $3\times10^{17}$, for example for a high value zoo animal or agricultural animal such as an elephant, are within the scope of the invention. For preventive immunizations, or periodic treatment, or treatment of a small wild animal, smaller doses such as less than about $3\times10^{9}$, or less than about $3\times10^{8}$, or even less than about $3\times10^{7}$ per dose, are within the scope of the invention.

Administration of Pharmaceutical Compositions

After formulation with an appropriate pharmaceutically acceptable carrier in a desired dosage, the pharmaceutical compositions of this invention can be administered to humans and other mammals topically (as by powders, ointments, or drops), orally, rectally, mucosally, sublingually, parenterally, intracisternally, intravaginally, intraperitoneally, bucally, ocularly, or nasally, depending on the severity and nature of the infectious agent being treated.

In various embodiments of the invention herein, oral and intranasal inoculation using spores and vegetative cells of *B. subtilis* engineered to express TTFC are compared. It was observed that high titers of antibodies, sufficient for protection against a lethal dose of tetanus toxin, were produced in mice after intranasal administration of vegetative cells expressing cytoplasmic TTFC or spores displaying TTFC as a fusion protein to a spore coat protein. These vaccines proved to have a long shelf life at elevated temperatures when stored in the dry state.

While intranasal administration was demonstrated to be surprisingly effective in examples herein, the antigen associated with spores and/or vegetative cells, preferably lyophilized, following vegetative cytoplasmic expression of the antigen prior to sporulation leads to a vaccine that is administered in any of a variety of routes. For example, it is envisioned that for agricultural animals, such as immunizing chicken or ducks for viral influenza, oral or intranasal administration would be highly suitable.

Liquid dosage forms for oral administration include, but are not limited to, pharmaceutically acceptable emulsions, microemulsions, solutions, suspensions, syrups and elixirs. In addition to the active agent(s), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of an inventive pharmaceutical composition include ointments, pastes, creams, lotions, gels, powders, solutions, sprays, inhalants, or patches. The active agent is admixed under sterile conditions with a pharmaceutically acceptable carrier and any needed preservatives or buffers as may be required. For example, ocular or cutaneous infections may be treated with aqueous drops, a mist, an emulsion, or a cream. Administration may be therapeutic or it may be prophylactic. Prophylactic formulations may be present or applied to the site of entry of potential disease organisms, such as, in the case of topical infectious organisms such as herpes virus, to wounds, such as contact lenses, contact lens cleaning and rinsing solutions, containers for contact lens storage or transport, devices for contact lens handling, eye drops, surgical irrigation solutions, ear drops, eye patches, and cosmetics for the eye area, including creams, lotions, mascara, eyeliner, and eyeshadow. The invention includes products which contain the compositions having the lyophilized vegetative cells or spores (e.g., gauze bandages or strips), and methods of making or using such devices or products. These devices may be coated with, impregnated with, bonded to or otherwise treated with a vaccine composition. For sites of disease entry that are primarily spread by droplet infection, such as rhinovirus and influenza, intranasal administration is suitable.

The ointments, pastes, creams, and gels may contain, in addition to an active agent of this invention, excipients such as animal and vegetable fats, oils, waxes, paraffins, starch, tragacanth, cellulose derivatives, polyethylene glycols, silicones, bentonites, silicic acid, talc, zinc oxide, or mixtures thereof.

Powders and sprays can contain, in addition to the agents of this invention, excipients such as talc, silicic acid, aluminum hydroxide, calcium silicates, polyamide powder, or mixtures of these substances. Sprays can additionally contain customary propellants such as chlorofluorohydrocarbons.

Transdermal patches have the added advantage of providing controlled delivery of the active ingredients to the body. Such dosage forms can be made by suspending spores in the matrix applied to the patches, or dispensing the compound in the proper medium. Absorption enhancers can also be used to increase the flux of the antigenic peptide released from spores into the compound, for passage across the skin. The rate can be controlled by either providing a rate controlling membrane or by dispersing the compound in a polymer matrix or gel.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized prior to addition of spores, for example, by filtration through a bacterial-retaining filter, or by incorporating sterilizing agents in the form of sterile solid compositions which can be dissolved or dispersed in sterile water or other sterile injectable medium prior to use. In order to prolong the effect of an active agent, it is often desirable to slow the absorption of the agent from subcutaneous or intramuscular injection. Delayed absorption of a parenterally administered active agent may be accomplished by dissolving or suspending the agent in an oil vehicle. Injectable depot forms are made by forming microencapsule matrices of the agent in biodegradable polymers such as polylactide-polyglycolide. Depending upon the ratio of active agent to polymer and the nature of the particular polymer employed, the rate of active agent release can be controlled. Examples of other biodegradable polymers include poly(orthoesters) and poly(anhydrides). Depot injectable formulations are also prepared by entrapping the agent in liposomes or microemulsions which are compatible with body tissues.

Compositions for rectal or vaginal administration are preferably suppositories which can be prepared by mixing the active agent(s) of this invention with suitable non-irritating excipients or carriers such as cocoa butter, polyethylene glycol or a suppository wax which are solid at ambient temperature but liquid at body temperature and therefore melt in the rectum or vaginal cavity and release the active agent(s).

Solid dosage forms for oral, mucosal or sublingual administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof.

Solid compositions of a similar type may also be employed as fillers in soft and hard-filled gelatin capsules using such excipients as milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent(s) may be admixed with at least one inert diluent such as sucrose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active agent(s) only, or preferentially, in a certain part of the intestinal tract, optionally, in a delayed manner. Examples of embedding compositions which can be used include polymeric substances and waxes.

Uses of Pharmaceutical Compositions

As discussed above and described in greater detail in the Examples, spores, spore preparations, vegetative cells, and vegetative cell preparations, e.g., by lyophilization, particularly bacterial spores, e.g., spores of a *Bacillus*, are used to prepare a heat resistant stable active vaccine by associating with an antigen from an infectious agent during sporulation. In general, it is believed that these vaccines will be clinically useful in immunizing subjects for resistance to infectious diseases. The present invention encompasses the treatment of a variety of infectious diseases arising from infection with bacteria, viruses, fungi, and parasites. The vaccines herein are particularly useful to treat compromised patients, particularly those anticipating therapy involving, for example, immunosuppression and complications associated with systemic treatment with steroids, radiation therapy, non-steroidal anti-inflammatory drugs (NSAID), anti-neoplastic drugs and anti-metabolites.

In addition, vegetative cells and spores associated with antigens from tumors, tumor cells/cell lines, and allergy producing proteins are contemplated. Allergy producing proteins and macromolecules include for example dust mite proteases, cat and dog salivary proteases, and proteins found in pollens of allergens such as pollen of grass and trees such as, ragweed, timothy and maple trees. The unprecedented stability of the vaccine compositions, and the rapid response as shown by appearance of serum antibodies following intranasal administration, indicates that the vaccines can be used by patients in a home setting, and can be supplied in suitable single dose or measured dose formats, to be used as needed, for example, seasonally.

A skilled person will recognize that many suitable variations of the methods may be substituted for or used in addition to those described above and in the claims. It should be understood that the implementation of other variations and modifications of the embodiments of the invention and its various aspects will be apparent to one skilled in the art, and that the invention is not limited by the specific embodiments described herein and in the claims. The present application mentions various patents, scientific articles, and other publications, each of which is hereby incorporated herein in its entirety by reference.

The invention having how been fully described, it is exemplified by the following examples and claims which are for illustrative purpose only and are not meant to be further limiting.

EXAMPLES

Example 1

Genetic Engineering of Rotavirus VP6 and Chromosomal Insertion

VP6 is the inner capsid protein of rotavirus and has a molecular weight of approximately 45 kd, and is a known immunogen for use in vaccines to treat rotaviral infection. Fusions of the bovine and murine VP6 coding regions to a version of the Pspac promoter (Yansura et al., 1984, Proc. Natl. Acad. Sci. USA 81:439-443) were integrated at the sacA locus of the *B. subtilis* chromosome. The Pspac promoter was altered by introducing two site-directed mutations, C-12T and A+1G. These mutations increased the strength of the promoter. The VP6 coding regions were recovered from pCR.2.1-VP6 bovine (obtained from Dr. L. J. Saif, Ohio State University, Wooster, Ohio) and pBluescript-VP6 murine (GenBank accession no. U36474; obtained from Dr. H. B. Greenberg, Stanford University, Palo Alto, Calif.) by PCR and were cloned initially in vector pBB1378. The latter plasmid carries the *B. subtilis* veg promoter and a kanamycin resistance gene surrounded by the 5' and 3' ends of the sacA locus. An appropriately placed ribosome binding site was incorporated into VP6 constructs during the PCR step. The relevant fragments containing the ribosome binding site and the VP6 coding sequences were excised from the resulting plasmids by treatment with PacI and SacI and were cloned in similarly digested pBB1375. The latter plasmid carries the mutant Pspac promoter and a kanamycin resistance gene surrounded by the 5' and 3' ends of the sacA locus. When introduced into competent cells of *B. subtilis* strain BB2534 [ΔthyA ΔthyB trpC2 ΔsacA::(thyA⁺ cat)], the resulting transformants, BB2543 for bovine VP6 and BB2547 for murine VP6, arose by double crossover recombination at the sacA locus. *B. subtilis* strains BB2666 (containing bovine VP6) and BB2667 (containing murine VP6) are Thy$^+$ versions of the latter strains, respectively. The control strain, BB2643, had the same genetic organization as BB2666 and BB2667, except that the VP6 coding sequence was absent.

Example 2

Growth of Bacteria and Preparation of Vegetative Cells and Spores

*Bacillus subtilis* type 168 strain was used to construct the recombinant strains expressing TTFC. *E. coli* strain JM107 was used for cloning experiments. Bacterial strains were routinely grown in Luria broth (LB) and plates containing solid LB medium were prepared with neomycin (5 µg/ml) for *B. subtilis*, or kanamycin (25 µg/ml) or ampicillin (100 µg/ml) for *E. coli*. For some experiments, *B. subtilis* cells were grown in a defined medium (TSS) supplemented with glucose (0.5-1%), ammonium chloride (0.2%) and sodium glutamate (0.2%).

*B. subtilis* strains grown overnight on L agar plates were used to inoculate 4-L cultures in DS medium (Fouet et al., 1990; J. Bacteriol. 172: 835-844). After incubation with shaking (200 rpm) at 37° C. for 48 hrs, the mixture of spores and non-sporulating bacteria was harvested by centrifugation, washed with sterile deionized water, treated with egg white lysozyme (1 mg/ml) to kill non-sporulating cells, washed five additional times with sterile deionized water and stored at 4° C. in sterile water. Spores were titered by direct counting using a Petroff-Hauser chamber and by comparing colony-forming ability before and after heating a sample to 80° C. for 10 min.

The following bacterial strains were used in the examples: control *B. subtilis* spores (not carrying genes encoding antigens for vaccines), and *B. subtilis* capable of displaying either bovine or murine-derived VP6 (e.g., bovine (Bo)VP6 or murine (Mu) VP6 as described herein).

Example 3

Administration and Response Testing

BALB/c female mice of about 4-6 weeks were immunized intranasally with spores according to a specific schedule (e.g., dose administered at 0, 14, and 28 days) as shown in the figures. Each animal was administered $3 \times 10^9$ spores per dose.

Adjuvant was used with an antigen in examples herein to co-immunize animals to enhance the immune response. Cholera toxin (CT) produced by various strains of *Vibrio cholerae* promotes Th2 cytokine responses, and improves efficacy of the immune response involving one or more of IgG1, IgE, and mucosal IgA antibodies. *Escherichia coli* LT (R192G) is a mutated variant of a heat-labile enterotoxin produced by enterotoxigenic strains of *E. coli*. The LT (R192G) variant is non-toxic, and induces Th1 and Th2 cytokine responses and improves efficacy of the immune response involving one or more of IgG1, IgG2a, IgG2b, and mucosal IgA antibodies. Adjuvant volumes of 20 µl were used for immunization; CT was administered at 10 µg/dose, and *E. coli* LT (R192G) was administered at 5 µg/dose or 10 µg/dose.

Methods to determine effectiveness of immunization of mice administered with VP6 spore preparations (bovine or murine-derived VP6 spores or a negative control) included: mice were sampled for titer of serum anti-VP6 antibody, which was measured using ELISA. Mice were challenged orally with the agent that causes epizootic diarrhea of infant mice (EDIM), rotavirus, and were monitored for the course of rotavirus infection by measuring appearance of virus VP6 antigen in feces.

Example 4

Immunization with Bovine or Murine-Derived VP6 Spore Preparations in Presence of CT Caused Increased Serum Anti-VP6 Antibody Titer Animals were immunized with VP6 spores (with or without CT) and were tested for appearance of anti-VP6 antibody in serum. The mice were immunized intranasally on days 0, 14, and 28 and were tested on days 14, 28 and 42.

Animals immunized with spore preparations associated with bovine- or murine VP6 (FIG. 1, triangles or circles) showed significant production in serum of anti-VP6 as measured by titer response at day 28 and day 42 compared to animals administered control VP6 spores. Murine-derived VP6 spore preparations showed a slightly greater ability to elicit an antibody titer response than bovine-derived VP6 at day 42, and bovine derived VP6 spores resulted in a slightly greater response at day 28. See FIG. 1. Animals immunized with spore preparations of BB2643, a *B. subtilis* strain that does not contain rotavirus-derived sequences (with or without CT; squares) produced almost no serum anti-VP6 ELISA titer response at any of the tested dates.

Immunizing animals with bovine- or murine-associated VP6 spore preparations with CT adjuvant increased the serum anti-VP6 titer response compared to immunizing with bovine or murine-derived VP6 spore preparations absent adjuvant, at each of day 28 and day 42. (FIG. 1, open) The relative increase for serum anti-VP6 titer response for bovine-associated VP6 spore preparations with CT compared to control spore preparations absent adjuvant was similar at day 28 and day 42.

Intranasal immunizations with bovine- or murine-associated VP6 spore preparations caused increased serum antibody titer compared to control spore preparations not displaying VP6. Also, use of an adjuvant, i.e., administering bovine- or murine-associated VP6 spore preparations with CT, increased the serum antibody titer even further (open circles, open triangles).

Example 5

Intranasal Immunization with Bovine- or Murine-Associated VP6 Spores with CT Reduced Amount of Rotavirus in Feces in EDIM Rotavirus Infection Model Animals immunized with VP6 spore preparations were challenged orally with rotavirus, using the EDIM animal model of rotavirus infection, and mice were tested for infection by measuring viral antigen in feces by ELISA each day for seven days.

Figure 2:
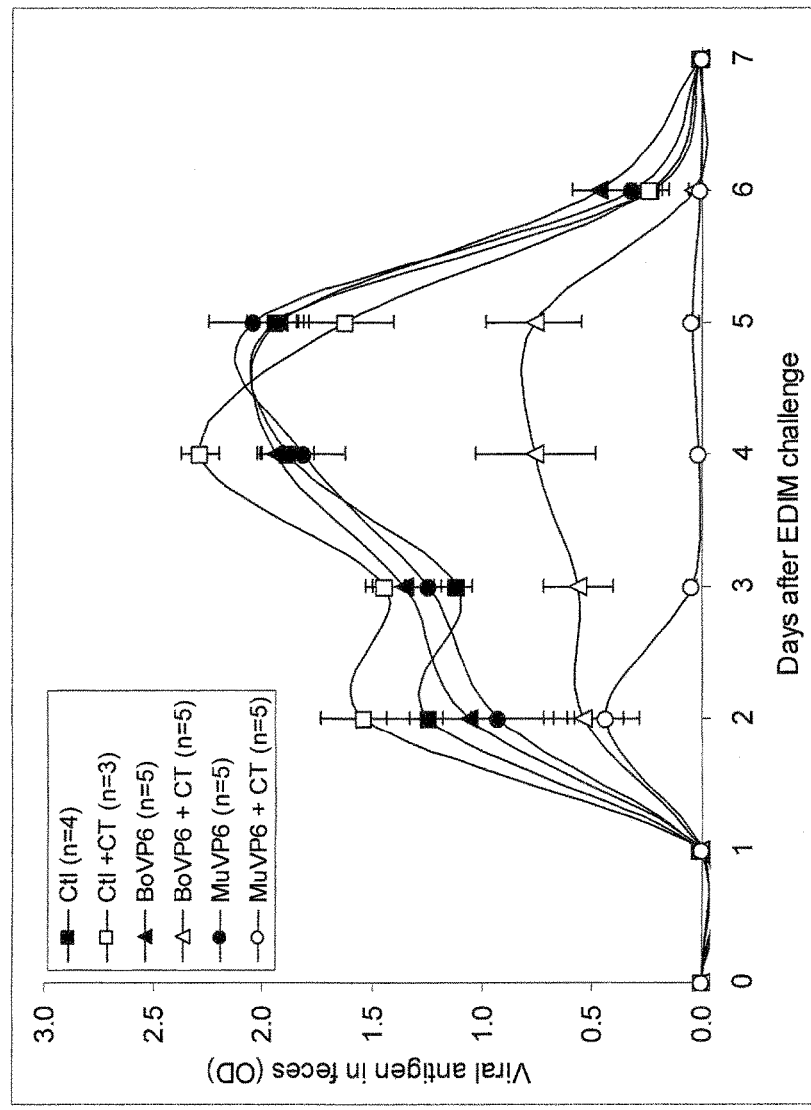
FIG. 2 is a line graph showing amount of rotavirus in feces as a function of time (days) after rotavirus challenge of mice previously immunized with each of: *B. subtilis* control spores (squares) and *B. subtilis* spores associated with either VP6 antigen from rotavirus strains of bovine origin (triangles) or with rotavirus of murine origin (circles). The *B. subtilis* spores were administered with cholera toxin (ct; open symbols) or without cholera toxin (closed symbols). The disease model was epizootic diarrhea of infant mice (EDIM). The data show that fecal viral content was reduced in EDIM mice previously inoculated with murine VP6 associated spores or with bovine VP6 associated spores, compared to control spores, and that adjuvant further decreased the fecal viral content.

Immunizing animals with VP6-associated spore preparations with or without adjuvant CT resulted in almost complete suppression of the disease. Animals administered control spores showed massive viral production from days 2 to 6 (FIG. 2). Bovine- or murine-associated VP6 spore preparations with CT adjuvant resulted in substantially reduced viral presence in comparison to administration of control spore preparations (with or without CT) with the infection appearing only at day 2, or at reduced levels from days 2 to 6. Animals administered murine-associated VP6 spore preparations and CT adjuvant showed substantially no virus in feces on day 3 (less than 0.2 OD). In contrast, animals administered control spore preparations continued to produce massive amounts of virus through day 6.

These data show that intranasal immunizations with VP6-associated spore preparations with CT caused reduced rotavirus infection after EDIM rotavirus challenge. This result is surprising because the VP6 antigen associated with the spores was expressed during vegetative growth of the cells, and as a cytoplasmically soluble product, rather than as a fusion to a sporulation protein during the sporulation phase.

Figure 1:
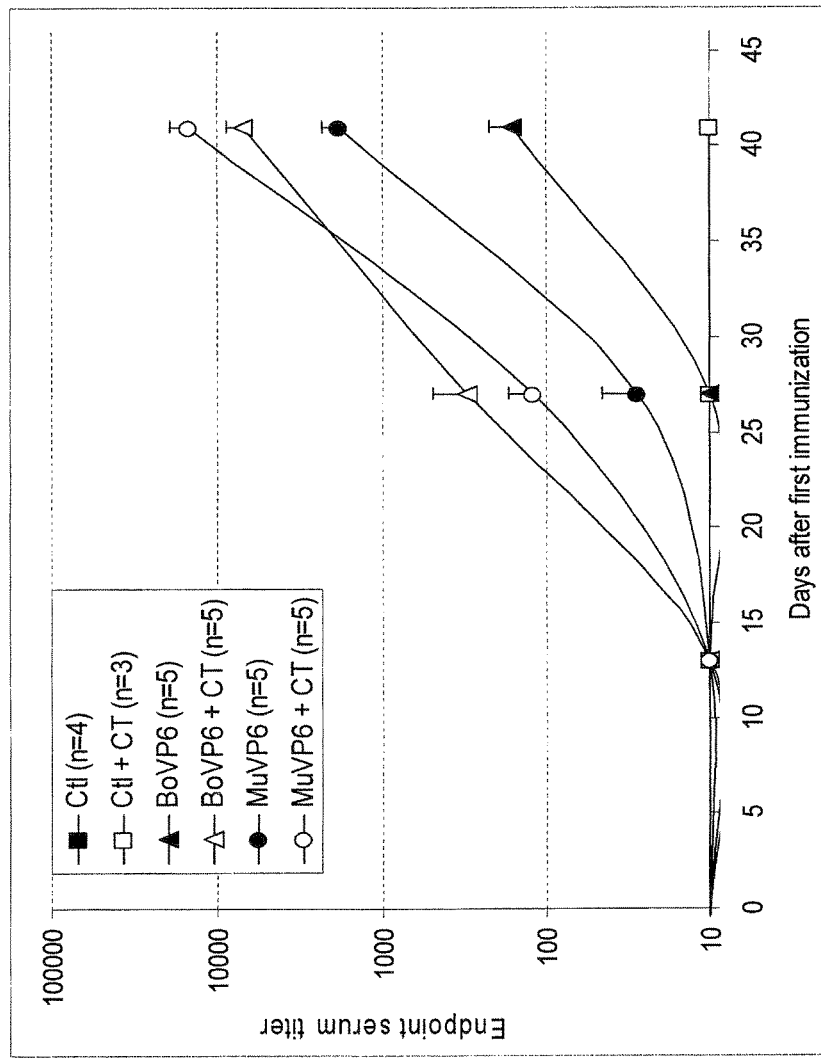
FIG. 1 is a line graph showing serum antibody titer to rotavirus VP6 observed following intranasal immunization of mice with *B. subtilis* control spores (squares) or *B. subtilis* spores associated with bovine (triangles) or murine (circles) VP6 antigen as a function of time (days after the first immunization). *B. subtilis* spores were administered with cholera toxin (open symbols) or without cholera toxin (closed symbols) as an adjuvant. The data show that animals administered VP6 antigen produced antibody, and that antibody titer was improved by use of the adjuvant.

Animals immunized with bovine- or murine-associated VP6 spores showed effective immunization: data show increased serum anti-VP6 antibody titer as measured by ELISA and reduced fecal rotavirus antigen in rotavirus challenged mice (FIG. 1 and FIG. 2, respectively). The use of adjuvant CT with bovine- or murine-associated VP6 spore preparations further improved immune response in mice, as shown by the increased serum anti-VP6 ELISA titer (100-fold increase) and reduced rotavirus presence (3-fold to 10-fold) compared to control administered spore preparations in absence of adjuvant.

To test the effect of adjuvant alone, groups of animals were administered CT with control spore preparations, and the data show no appearance of serum anti-VP6 antibody, or reduction of rotavirus presence in EDIM animals (FIGS. 1 and 2).

Example 6

Intranasal Immunizations with Bovine- or Murine-Associated VP6 Spores with LT (R192G) Show Increased Serum Anti-VP6 Titer Response Animals were administered VP6-associated spore preparations with adjuvant LT (R192G), and were tested for serum anti-VP6 antibody titer. The animals were administered spore preparations intranasally on days 0, 14, and 28 and serum was obtained on days 14, 28 and 42.

Figure 3:
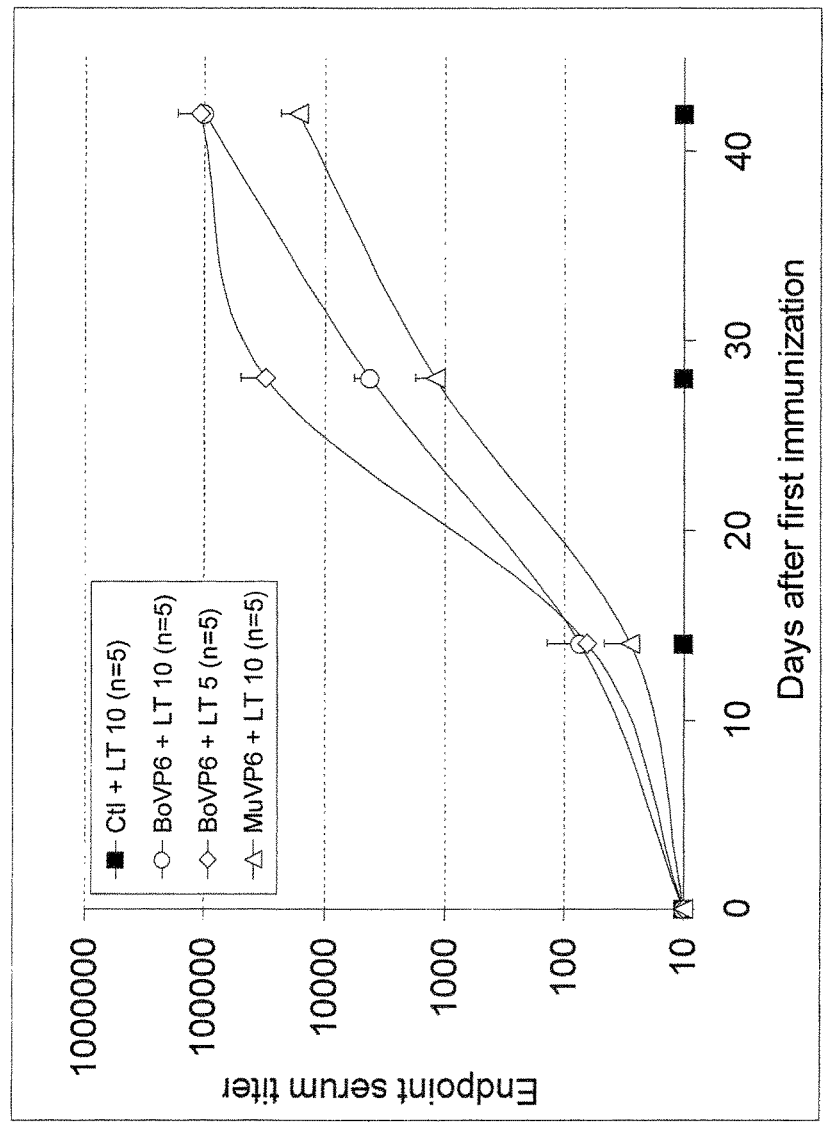
FIG. 3 is a line graph showing serum antibody titer specific for rotavirus VP6 observed after mice were immunized intranasally with *B. subtilis* control spores (squares) or *B. subtilis* spores associated with bovine derived VP6 (circles, diamonds) or murine derived VP6 (triangles) as a function of time (days after first immunization). *B. subtilis* spores were administered with an adjuvant prepared from non-toxic *Escherichia coli* LT (R192G having a mutation of arginine to glycine at residue 192) at 5 µg/dose or 10 µg/dose. The data show that an amount of 5 µg/dose or 10 µg/dose of LT (192G) was effective as an adjuvant. No serum antibody titer was observed in animals administered the control spores, even in the presence of the adjuvant.

It was observed that animals immunized with bovine-associated VP6 spores with 5 μg/dose or 10 μg/dose LT (R192G) produced a substantial titer of antibody (see FIG. 3). Bovine-associated VP6 spore preparations with adjuvant LT (R192G) resulted in greater serum antibody titers to rotavirus VP6, than murine-associated VP6 spores absent adjuvant (FIGS. 1 and 3). Both amounts of LT (R192G) of 5 μg/dose or of 10 μg/dose with the bovine- or murine-associated VP6 spores was effective in increasing serum antibody response to rotavirus VP6.

Control spore preparations without antigen with 10 μg/dose LT (R192G) produced no serum anti-VP6 ELISA titer response at all time periods, similar to the results observed with animals immunized with control spore preparations with 10 μg/dose CT in FIG. 1, as expected. These data shows that adjuvant enhances immune responses to spore preparations containing rotavirus VP6.

Example 7

Intranasal Immunizations with Bovine- or Murine-Associated VP6 Spore Preparations with LT (R192G) Show Reduced Rotavirus Infection in an EDIM Disease Model Animals were immunized intranasally with VP6-associated spore preparations, challenged orally with EDIM rotavirus, and were tested for viral production in feces, by ELISA for presence of the VP6 antigen, for each of seven days.

Figure 4:
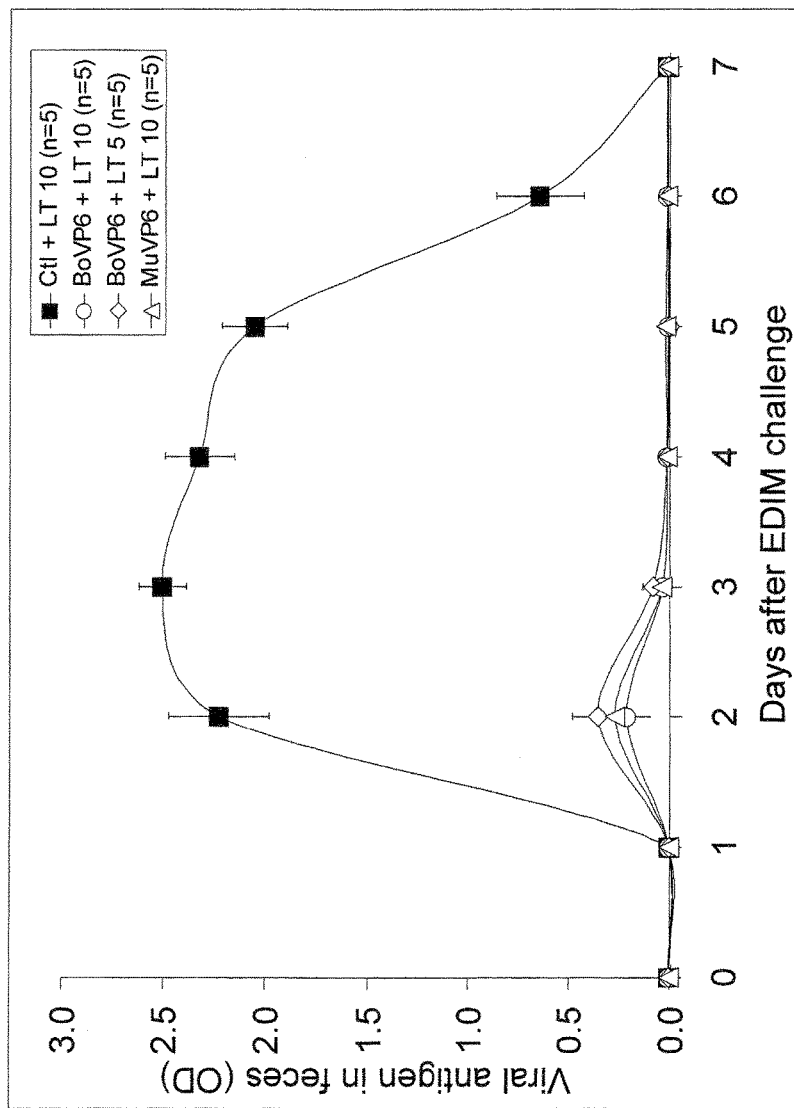
FIG. 4 is a line graph showing amount of rotavirus in feces as a function of time (days) after rotavirus challenge of mice immunized with *B. subtilis* control spores (squares) or *B. subtilis* spores associated with VP6 antigen of rotavirus strains of bovine origin (circles, diamonds) or murine origin (triangles). Spores were administered with an adjuvant prepared from non-toxic *Escherichia coli* LT (R192G) at 5 µg/dose or 10 µg/dose. The data show that the mice immunized with *B. subtilis* spores that were associated with bovine or murine VP6 recovered more quickly from the rotavirus infection than control mice, and that feces produced by the VP6-immunized mice contained far fewer virus particles than feces from the mice administered control spores.

Animals immunized with murine-associated VP6 spore preparations with 10 μg/dose LT (R192G), bovine-associated VP6 with μg/dose LT (R192G), or bovine-associated VP6 with 5 μg/dose LT (R192G) showed substantially reduced disease symptoms (FIG. 4, open symbols). The animals administered bovine- or murine-associated VP6 spores preparations showed almost no viral antigen in feces nor did animals administered bovine VP6 spore-associated preparations with adjuvant LT (R192G) at 5 μg/dose or 10 μg/dose (FIG. 4).

These data show that immunizing intranasally with bovine or murine derived VP6 spores preparations with LT (R192G) substantially reduced rotavirus in feces.

Animals administered bovine- or murine-associated VP6 spores preparations with LT (192G) were effectively immunized, as demonstrated by the increased serum anti-VP6 ELISA titers and the reduced fecal rotavirus content in EDIM rotavirus challenged animals.

*B. subtilis* spore preparations associated with a viral antigen were effective vaccines, generating protective immunity against rotavirus challenge in the EDIM animal disease model. Animals immunized with bovine- or murine-associated VP6 spores had significantly increased serum anti-VP6 response titers as compared to control spores, and an adjuvant such as CT or LT (R192G) further increased the serum antibody response to rotavirus VP6.

Example 8

Recombinant Strains Expressing TTFC

To construct a recombinant strain that expresses TTFC during vegetative growth stage, vector pBB1375 for expression of cloned DNA under the control of a highly active version of the semi-synthetic spac promoter was constructed by site-directed mutagenesis. Plasmid pBB1375 was derived from pSac-Kan (Middleton et al., 2004, Plasmid 51:238-245) by deleting the BseRII fragment (resulting in pBB1364) and then introducing Pspac between the BglII and XbaI sites. The version of the spac promoter in pBB1427 has two single-nucleotide mutations (SEQ ID No: 1) in conformance with the consensus sequences for promoters recognized by the sigma-A form of *B. subtilis* RNA polymerase (FIG. 5). The ribosome binding site (RBS) and ATG initiation codon of the *B. subtilis* gsiB gene were inserted between the spac promoter and tetC. The tetC sequence from positions 2855 to 4237 of the tetanus toxin gene of *Clostridium tetani* (GenBank no. X04436) were amplified and fused to the ATG initiation codon and the ribosomal binding site of the *B. subtilis* gsiB gene and cloned in parent plasmid pBB1375 to create pBB1427.

Competent cells of *B. subtilis* strain 168 were prepared by the two-step transformation method (Dubnau et al., 1994, Res. Microbiol. 145(5-6): 403-411). The plasmid pBB1427 was used to transform the competent cells (of genotype ΔthyA Δ thyB sacA::[thyA$^+$ cat]) to neomycin-resistance. Transformants arose by double-crossover recombination, resulting in the insertion of the Pspac-tetC construct within the sacA locus. A representative clone carrying genetic information for expression of TetC peptide cytoplasmically was named BB2646. A control strain, BB2643, carrying the Pspac promoter at the sacA locus without the appended tetC coding sequence was also prepared. This strain is a negative control that lacks genetic information encoding any antigen, i.e., carries an empty vector.

A strain displaying TTFC on the surface of spores as a fusion protein with CotC, a spore coat protein, was constructed by introducing into pSac-Kan a 374-bp DNA fragment that includes the cotC promoter and coding sequence fused in-frame at its C-terminus with a 3-alanine-codon linker and the coding sequence of TTFC (residues 2581 to 4237 of the tetanus toxin gene). The resulting plasmid, pBB1367, was introduced into the ΔthyA ΔthyB sacA::[thyA$^+$ cat] *B. subtilis* recipient strain by transformation as described above, leading to integration at the sacA locus and resistance to neomycin. A resulting transformant was named BB2645.

Strains carrying three integrated copies of the Pspac-tetC or cotC-tetC construct at different loci (sacA, thrC and amyE) in the *B. subtilis* chromosome were constructed. These strains, BB3059 for Pspac-tetC and BB3184 for cotC-tetC, were constructed by methods analogous to those for the single copy integrants. The CotC fusion causes expression of the antigen on a spore coat protein. Expression of antigens on the surface of spores, or on the surface of vegetative cells or cytoplasmically in vegetative cells is illustrated in FIG. 21. Constructs are shown in FIG. 22.

Example 9

Preparation of Vegetative Cells and Extraction of Vegetative Cell Lysates

Vegetative *B. subtilis* cells of strains BB2643 and BB2646 were prepared for use in immunization by growth at 37° C. in LB to an absorbance at 600 nm ($OD_{600}$) of 0.8-1.0. For vegetative cell lysates, cells were grown to $OD_{600}$=1.5 in LB medium or defined medium, the cell suspension was washed and lysed by sonication, and collected by high-speed centrifugation. Proteins concentrations were measured using the Pierce Protein Assay kit (Thermo Fisher Scientific, Rockford Ill.). For Western blotting, proteins were subjected to SDS-PAGE and blotted on nitrocellulose membranes. After successive incubation of the membrane with rabbit polyclonal anti-tetanus toxin antibody (1:500) and goat anti-rabbit IgG conjugated with horseradish peroxidase (Pierce, 1:500), the protein bands were visualized by chemiluminescence (Pierce), following the manufacturer's instructions (FIG. 6).

Example 10

Immunofluorescence Microscopy

*B. subtilis* strains (BB2643 and BB2646) grown in LB medium were fixed in situ as described previously (Harry et al., 1995, J. Bacterial. 177: 3386-3393). Cultures were vortexed to disrupt clumps of bacteria before fixation. A 0.25-ml volume of bacterial culture was mixed with concentrated fixative solution to give 2.4% (vol/vol) parafamialdehyde, 0.04% (vol/vol) glutaraldehyde, and 30 mM Na—PO4 buffer (pH 7.5) and the mixture was incubated for 10 min at room temperature (20-22° C.) and then for 50 min on ice. The fixed bacteria were washed three times in PBS, pH 7.4, at room temperature and were resuspended in 100 μl of GTE (50 mM glucose, 20 mM Tris-HCl, pH 7.5, 10 mM EDTA). A freshly prepared lysozyme solution in GTE was added to a final concentration of 2 mg/ml. Samples (10 μl) were immediately distributed into wells of a multiwell microscope slide (ICN Biochemicals; Aurora, Ohio) that had been treated with 0.1% (wt/vol) poly-L-lysine (Sigma). After 4 min, the liquid was aspirated from the wells, which were then allowed to dry completely. The slides were immersed in methanol at −20° C. for 5 min and then at −20° C. in acetone for 30 s and allowed to dry. Ten of blocking solution, 2% bovine serum albumin (BSA) in PBS (BSA-PBS) was added to each well, and slides were incubated for 15 min at room temperature and washed nine more times. Samples were incubated with polyclonal rabbit anti-tetanus toxin for 1 h at room temperature, washed three times, and were incubated with anti-rabbit immunoglobulin G (IgG)-fluorescein isothiocyanate (Southern Biotech; Birmingham, Ala.) for 1 h at room temperature. After three washings, the samples were observed and photographed with a Zeiss fluorescence microscope fitted with a Nikon DMX1200 digital camera, and data were analyzed with Lucia GF software.

Example 11

Immunization Regimens

Groups of five 6- to 8-week old female BALB/c mice were inoculated via the intranasal route with vegetative cells of various *B. subtilis* strains *B. subtilis* vegetative cells were cultured in LB broth for 4-6 hr until the culture reached an $OD_{600}$ of 0.8 to 1.0 at 600 nm. After harvesting, the cell pellets were resuspended in an equal volume of PBS. Spores were harvested after 48-72 hr of incubation with shaking in DS medium (Fouet et al., 1990). The spores were washed repeatedly with sterile deionized water, treated with lysozyme (1 mg/ml) and washed again several times. Residual contamination by vegetative cells, as detected by phase contrast microscopy, was 1% or less. Spores were stored in deionized water at 4° C.

Mice were inoculated intranasally with 20 μl of cell or spore suspension per dose ($10^7$ to $10^9$ vegetative cells or $10^8$ to $10^9$ spores per dose; 10 μl per nare) on days 0, 2, 14, 16, 28, and 30 (6 inoculations) or 0, 14, and 28 (3 inoculations). For a positive control, mice were immunized intramuscularly (i.m.) with 50 μl of a commercial DTaP vaccine adsorbed (triple vaccine for diphtheria, tetanus and pertussis; Tripedia®, Sanofi Pasteur Inc., Swiftwater, Pa., USA) on days 0, 14, and 28 (3 inoculations). Blood samples from inoculated mice were acquired on days −1, 13, 27, and 41.

Example 12

Detection of TTFC-Specific Serum Antibody Responses

Anti-TTFC antibody amount in serial three-fold dilutions of sera was measured by ELISA. Absorbance values of pre-immune sera were used as reference blanks. Dilution curves were drawn for each serum sample and endpoint titers, representing the reciprocal value of the last dilution that gave an optical density ≥0.1, were expressed as the means±S.E. for animals submitted to the same vaccine regimen. Serum TTFC-specific IgG subclass responses were measured with same experimental procedure but using peroxidase-conjugated rabbit anti-mouse IgG1 and IgG2a. Titers lower than 100 (negative samples) were arbitrarily assigned as 33.

Example 13

Tetanus Toxin Challenge

Three weeks following the last immunization, mice were challenged intraperitoneally with purified tetanus toxin (0.8 ng), determined previously to be an amount that is twice $LD_{100}$. Mice were observed for morbidity or mortality daily for 10 days.

Example 14

Recombinant TTFC Expressed in B. Subtilis Vegetative Cells

Figure 6:
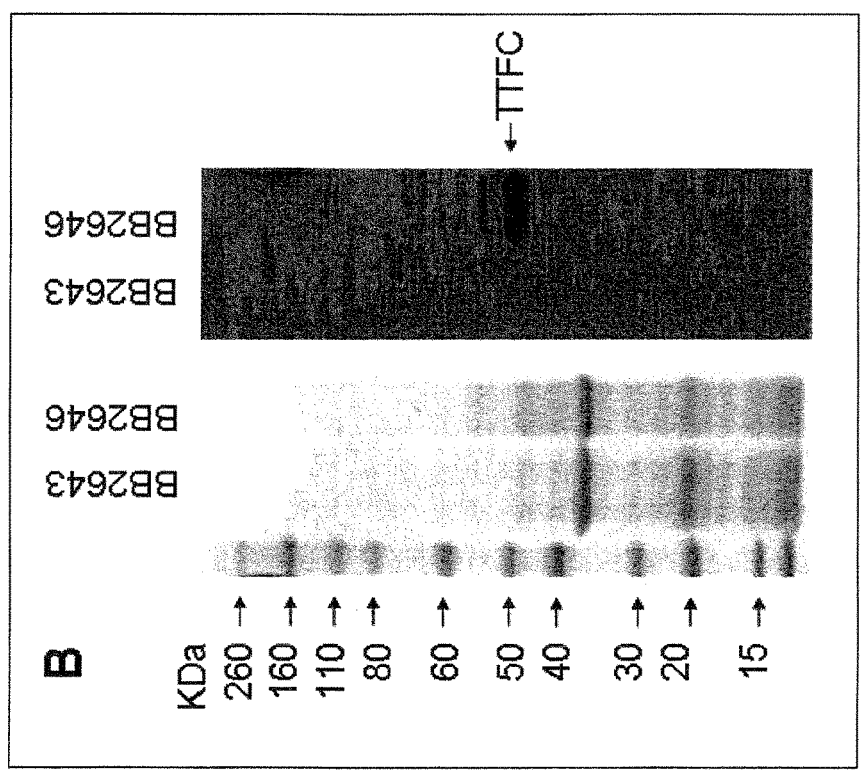
FIG. 6 is a set of photographs showing expression of tetanus toxin C-terminal fragment (TTFC synonymous with TetC) in recombinant *B. subtilis*. Colonies grown of solid medium were labeled with rabbit anti-tetanus toxin (TT) antibody followed by anti-rabbit IgG-FITC conjugate of TTFC-expressing strain BB2646 but not control BB2643 strain, and expression by colonies was observed by presence of fluorescein stain.

A recombinant strain of B. subtilis was constructed to express the heavy chain C fragment of tetanus toxin (TTFC), corresponding to the 457 C-terminal amino acids of the 1315-residue tetanus holotoxin, from a strong and constitutively active mutant version of the spat promoter. This construct was integrated at the sacA locus in strain BB2646. TTFC expression in BB2646 was confirmed by Western blotting and immunofluorescent (IF) staining (FIG. 6).

Example 15

Oral Immunization with BB2646 Spores

Figure 7:
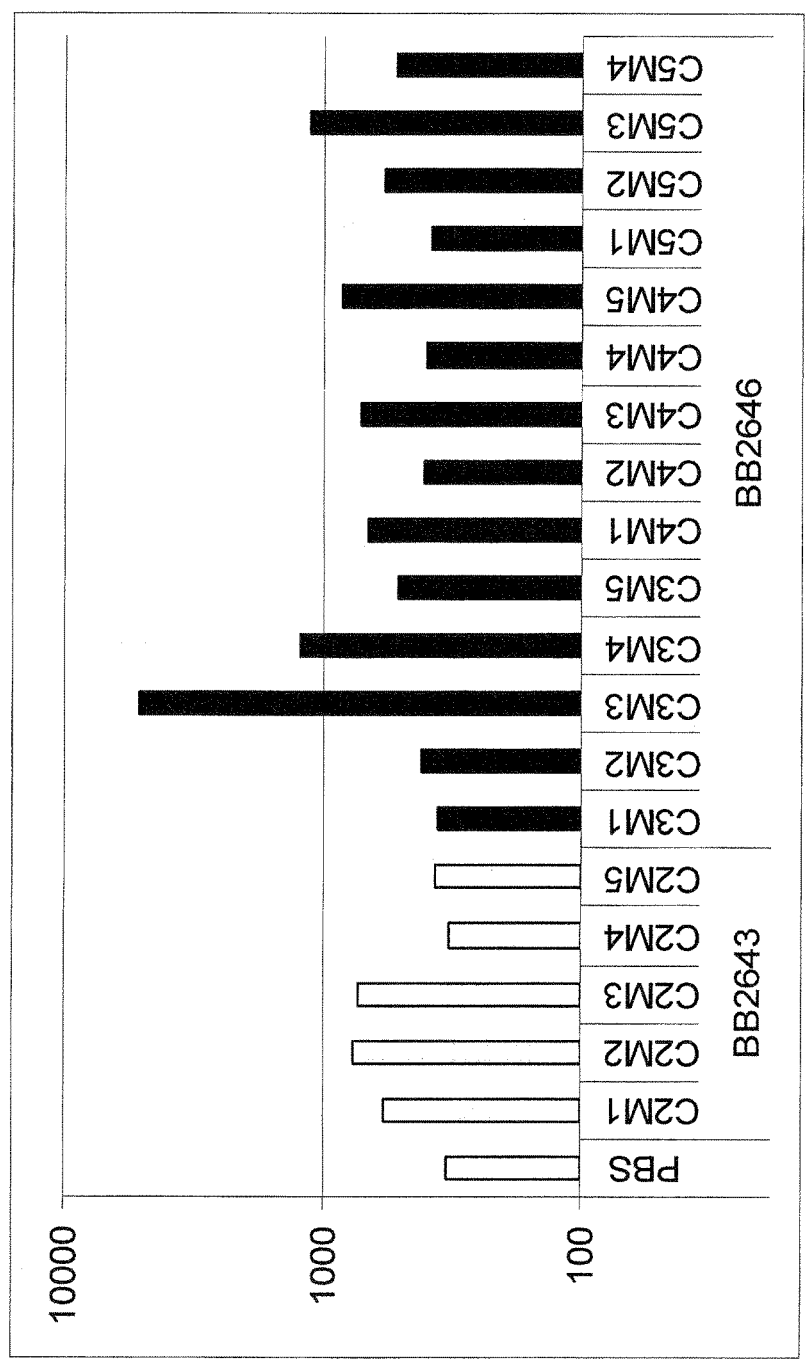
FIG. 7 is a bar graph showing serum anti-TTFC antibody titers after oral immunization of BALB/c mice with each of strains BB2646 carrying tetanus toxin C-terminal fragment (TetC synonymous with TTFC), and strain BB2643, a negative control.

Ability of spore preparations of strain BB2646 to generate a protective immune response after oral immunization of mice was tested. Mice immunized with the spore preparations showed very little increase in anti-TTFC serum antibody titer even after six inoculations with more than $10^{10}$ spores per inoculation, compared to the control strain BB2643 (FIG. 7). Constructs in which the TTFC-encoding sequence was fused to a vegetative cell wall protein (WapA) or a spore coat protein (CotC) were also tested. In neither of the latter cases was any significant increase in anti-TTFC titers in serum observed. Although some colonization of the mouse GI tract by the recombinant strain could be detected, the BB2646 titer in fecal samples declined within 7 days.

Example 16

Intranasal Immunization with BB2646 Spores

Figure 8:
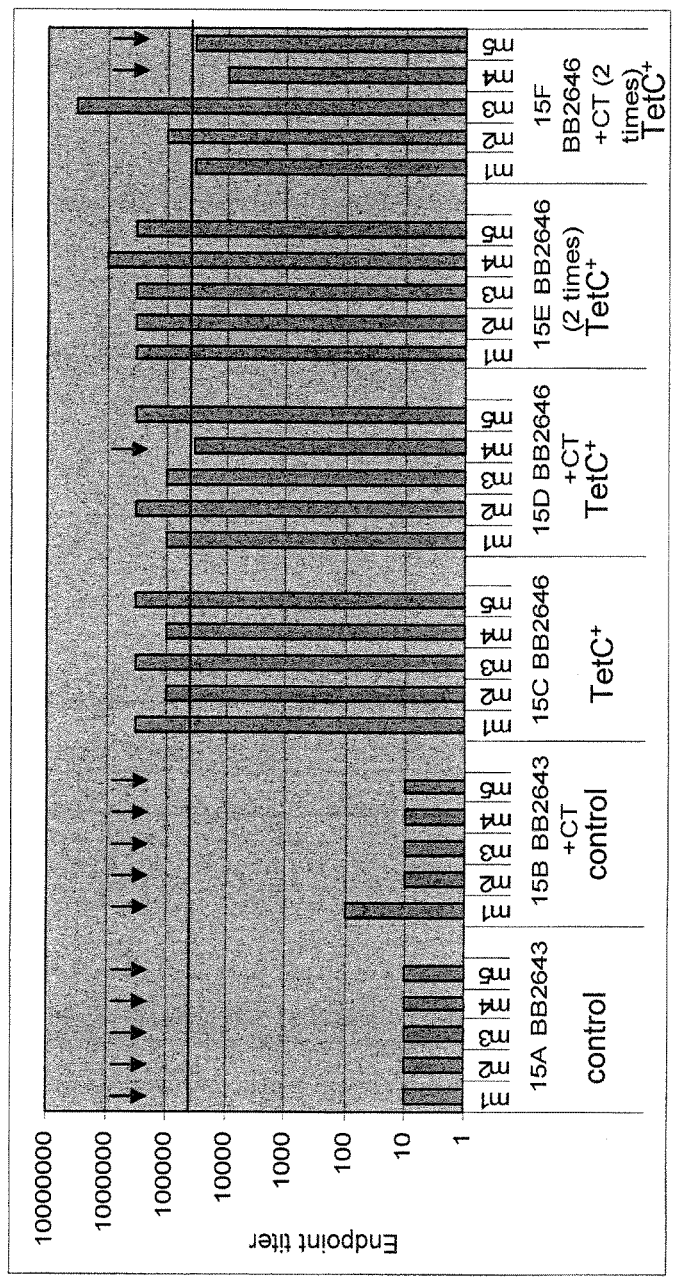
FIG. 8 is a bar graph showing serum anti-TTFC antibody titers after intranasal immunization of BALB/c mice with *B. subtilis* vegetative cells expressing TetC cytoplasmically or after intra-muscular (i.m.) immunization with a conventional DTaP vaccine (positive control). For immunization with *B. subtilis*, mice were inoculated intranasally with $1 \times 10^8$ cells in a volume of 20 µl on days 0, 14, and 28 or on days 0, 2, 14, 16, 28, and 30. For DTaP vaccination, mice were injected i.m. with 50 µl of DTaP vaccine as provided by the manufacturer. Arrows indicate mice that died after challenge.

Ability of the BB2646 spore preparations from cells expressing the antigen cytoplasmically to immunize mice after intranasal inoculation was tested. In this case, very high levels of serum anti-TTFC antibodies were detected after three rounds of inoculation (one or two doses per round) at two-week intervals (FIG. 8). The titer after the third round of immunization was the same whether the mice received a total of six inoculations or three (FIG. 8) and was also as high as that generated by intramuscular inoculation with commercial DTaP vaccine.

Figure 9:
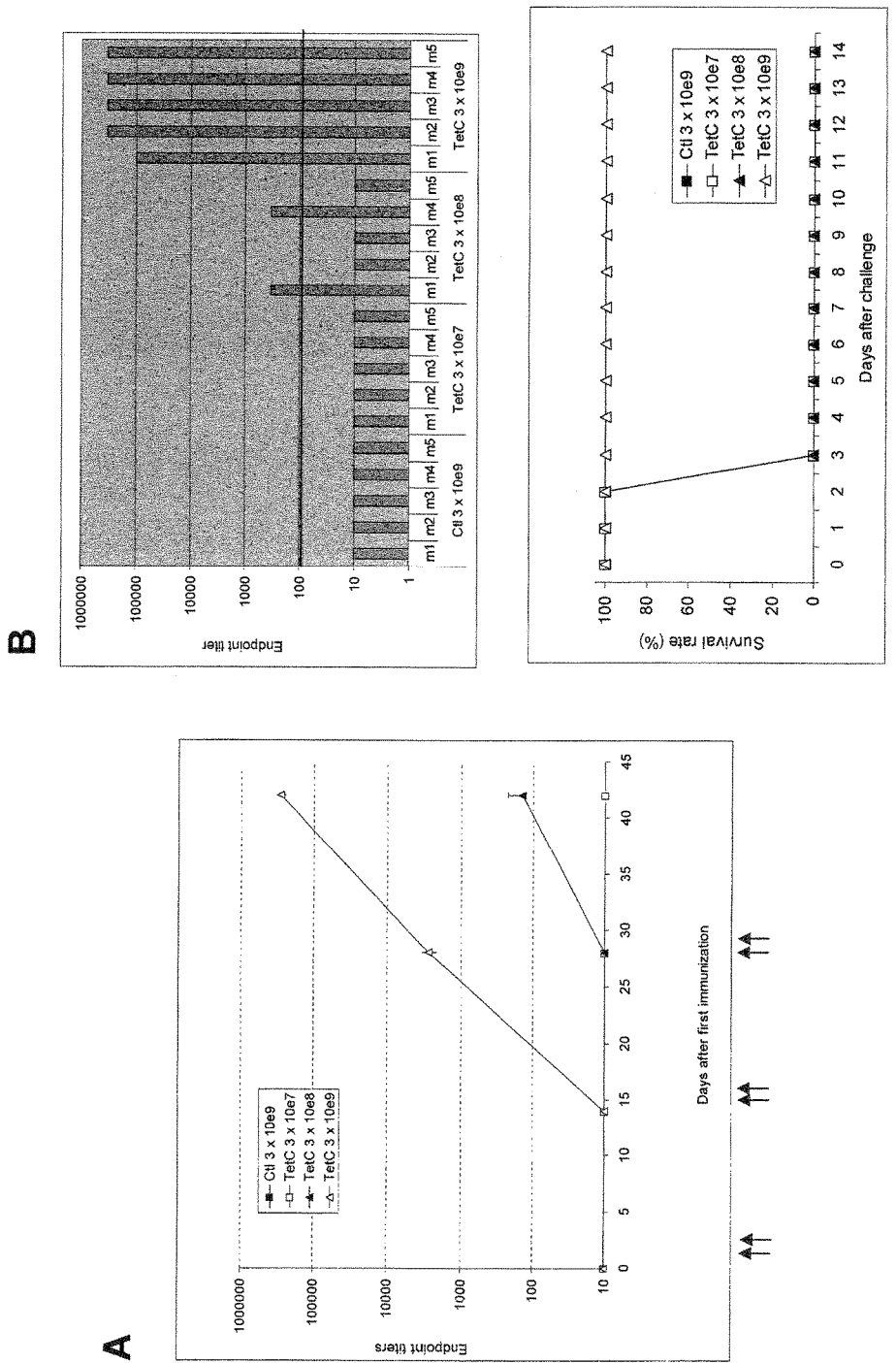
FIG. 9 is a set of line graphs and a bar graph showing dose response of immune response generated by spore preparations of strain BB2646 and protection against lethal tetanus toxin challenge in BALB/c mice. Each immunized mouse was tested for immune response by intraperitoneal injection with an amount of tetanus toxin equivalent to twice the 100% lethal dose ($LD_{100}$) of tetanus toxin and was examined for symptoms at the time indicated on the abcissa. It was observed that more than $10^9$ spores were required for effective immunization.

These mice were completely protected from lethal toxin challenge (FIG. 8). Co-administration of cholera toxin (CT) as an adjuvant did not affect the observed immune response (FIG. 8). Mice inoculated with control spores (strain BB2643) that were isogenic to BB2646 and lacked the TTFC coding sequence gave no detectable antibody response and were fully sensitive to challenge by tetanus toxin (FIG. 8). The dose of spores between $3 \times 10^8$ and $3 \times 10^9$ per dose was observed to give protective immunity (FIG. 9).

Example 17

Mechanism of Intranasal Immunization by BB2646 Spores

Figure 10:
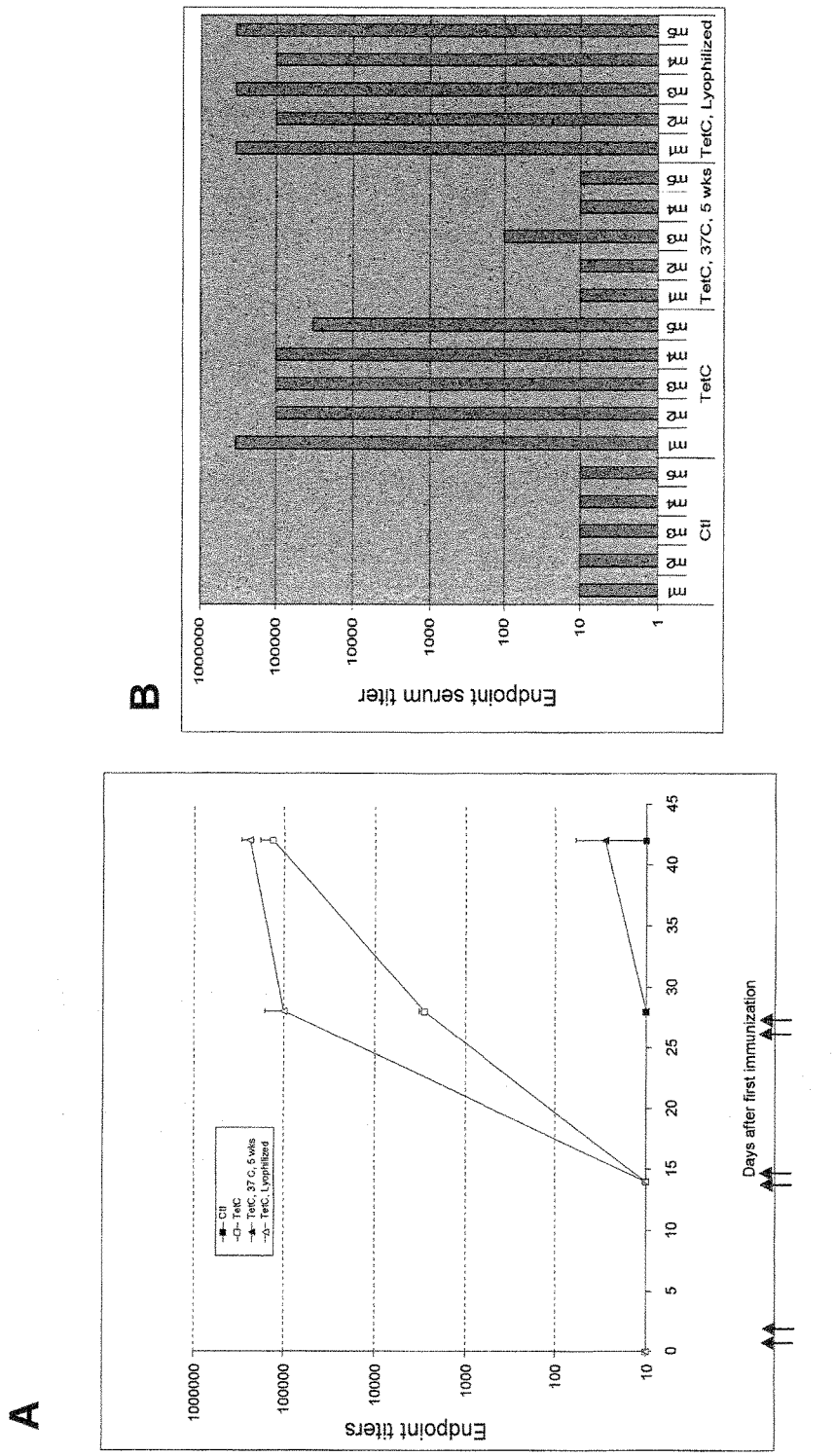
FIG. 10 is a line graph and a bar graph showing effect of incubation at 37° C. on immunogenicity of BB2646 spores. It was observed that immunogenicity was stable at 4° C. after lyophilization, but not in liquid suspension after storing for 5 weeks at 37° C.
Figure 11:
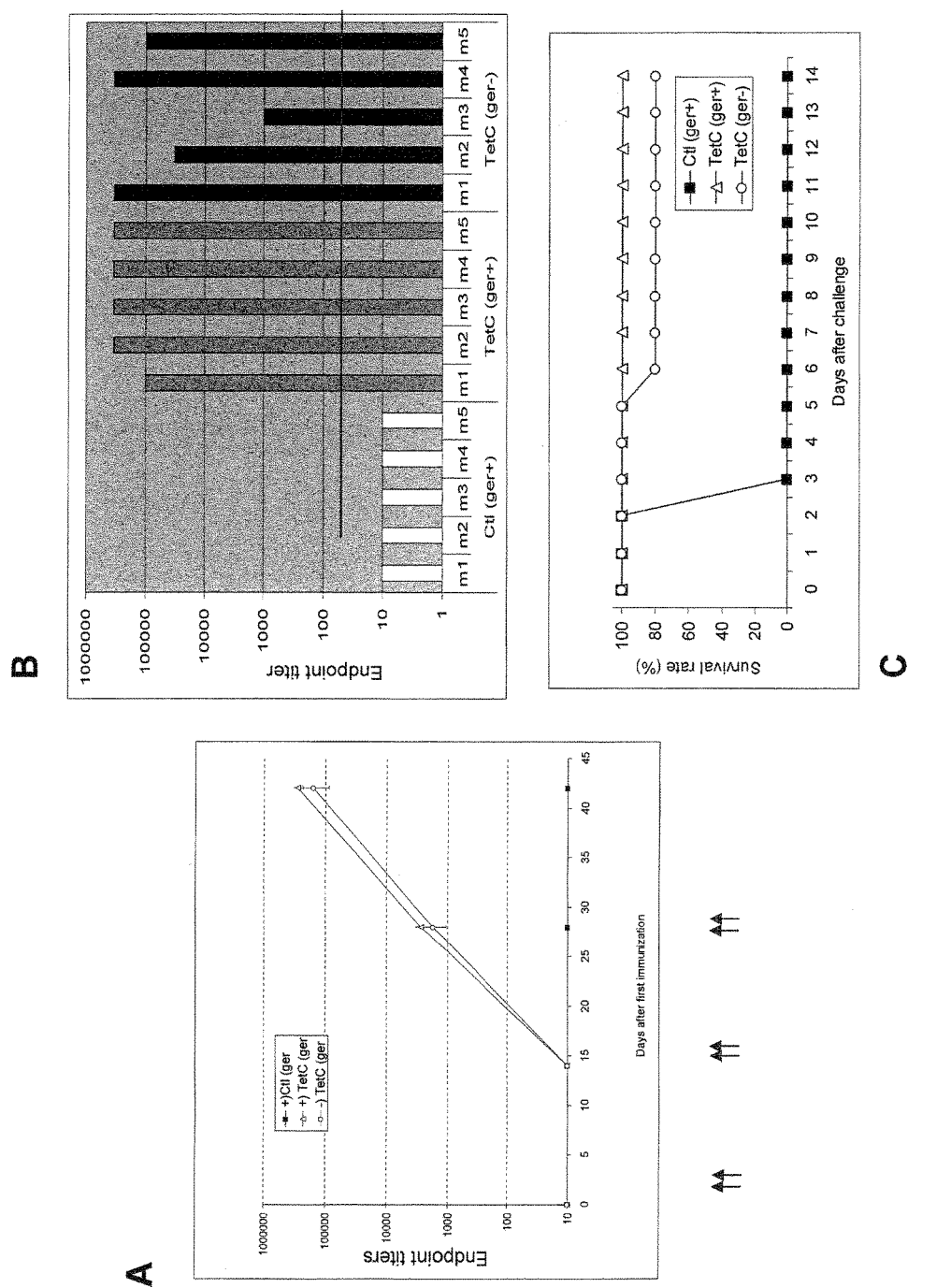
FIG. 11 is a set of graphs showing role of spore germination in immunogenicity of BB2646 spores.

Without being limited by any particular theory or mechanism of action, a model the protective immunity afforded by spore preparations of BB2646 might be due to germination of the spores in the nasopharynx, followed by outgrowth of vegetative cells, expression of TTFC and presentation of the TTFC to cells of the nasopharyngeal immune system. However dissection of the nasopharynx of inoculated mice revealed the presence of spores but not of any detectable level of vegetative cells. Moreover, incubation of the spores at 80° C. for 10 min or at 37° C. for 5 weeks, conditions which do not affect spore viability, greatly reduced immunogenicity of the spore preparation (FIG. 10). In addition, introduction into strain BB2646 of a mutation that greatly reduced the ability of the spores to germinate had only a small effect on immunogenicity (FIG. 11). Finally, purification of the spores by density gradient centrifugation removed the ability to induce an immune response (data not shown). Taken together these results suggest strongly that the spore form of strain BB2646 was not responsible for generating the protective immunity that we had seen.

Example 18

Immunization by Vegetative Cells of BB2646

During spore preparation, contaminating vegetative cells were removed by osmotic shock, treatment with lysozyme and extensive washing to the extent that the level of contamination was no higher than 1% as measured by phase contrast microscopy. Nonetheless, a low level of contamination could have been present. Since it is the vegetative form of BB2646 that expresses the TTFC antigen, whether such vegetative cells could account for the immunization obtained with spore preparations.

Figure 12:
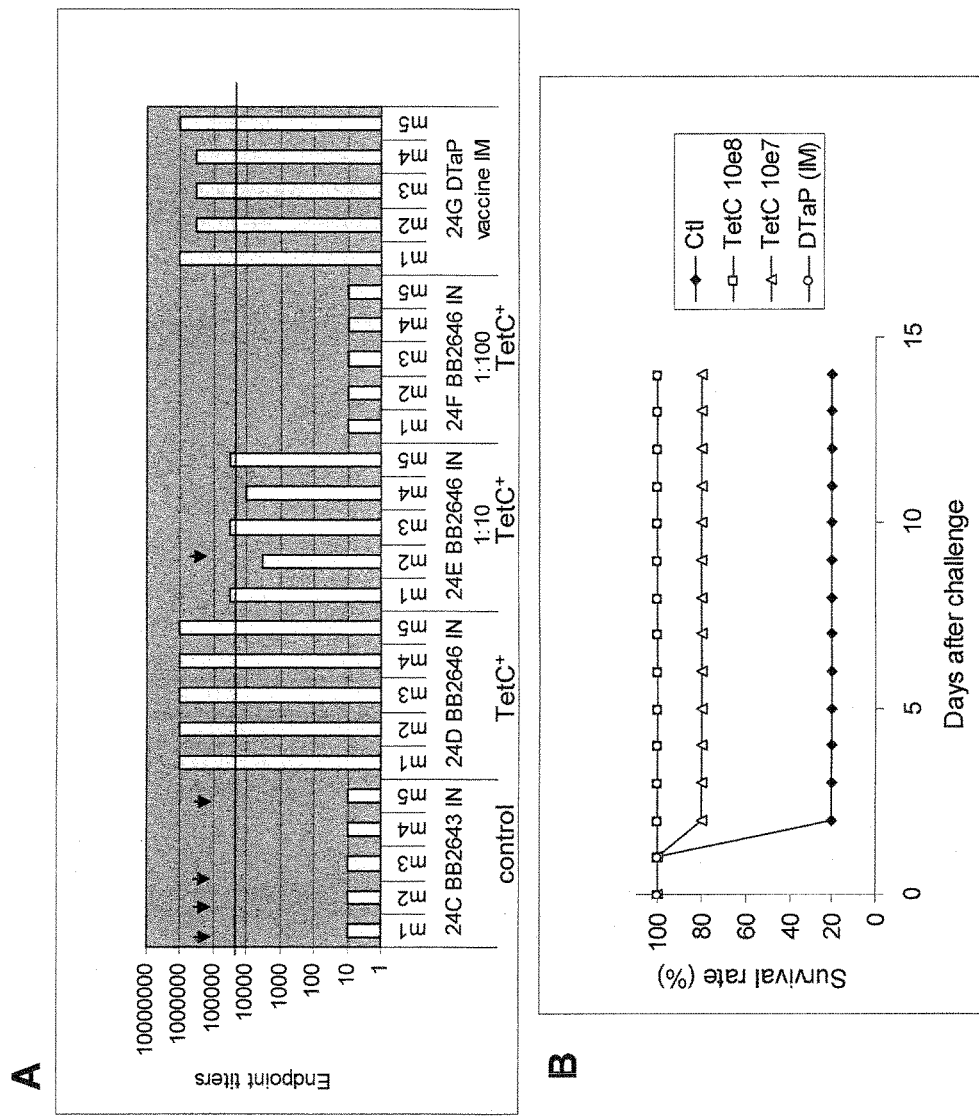
FIG. 12 is a line graph and a bar graph showing antibody endpoint titers (panel A) and survival rate (panel B) of mice following intranasal immunization with vegetative cells of strain BB2646 expressing TetC in cytoplasm, and controls. Survival in mice receiving $10^8$ (open squares) spores and mice receiving intramuscular (IM) injection of DTaP-associated spores was 100%, compared to lower survival levels in mice receiving $10^7$ (open triangles) and control (closed diamonds) animals.

In fact, freshly grown vegetative cells harvested from growth medium and resuspended in PBS were observed to be very active inducers of protective immunity. Three doses of vegetative cells of BB2646 with titers as low as $10^7$ cells per dose were observed to give a strong antibody response and protection against tetanus toxin (FIG. 12). Thus, vegetative cells contaminating the spore preparation could explain protective immunity observed herein.

Figure 13:
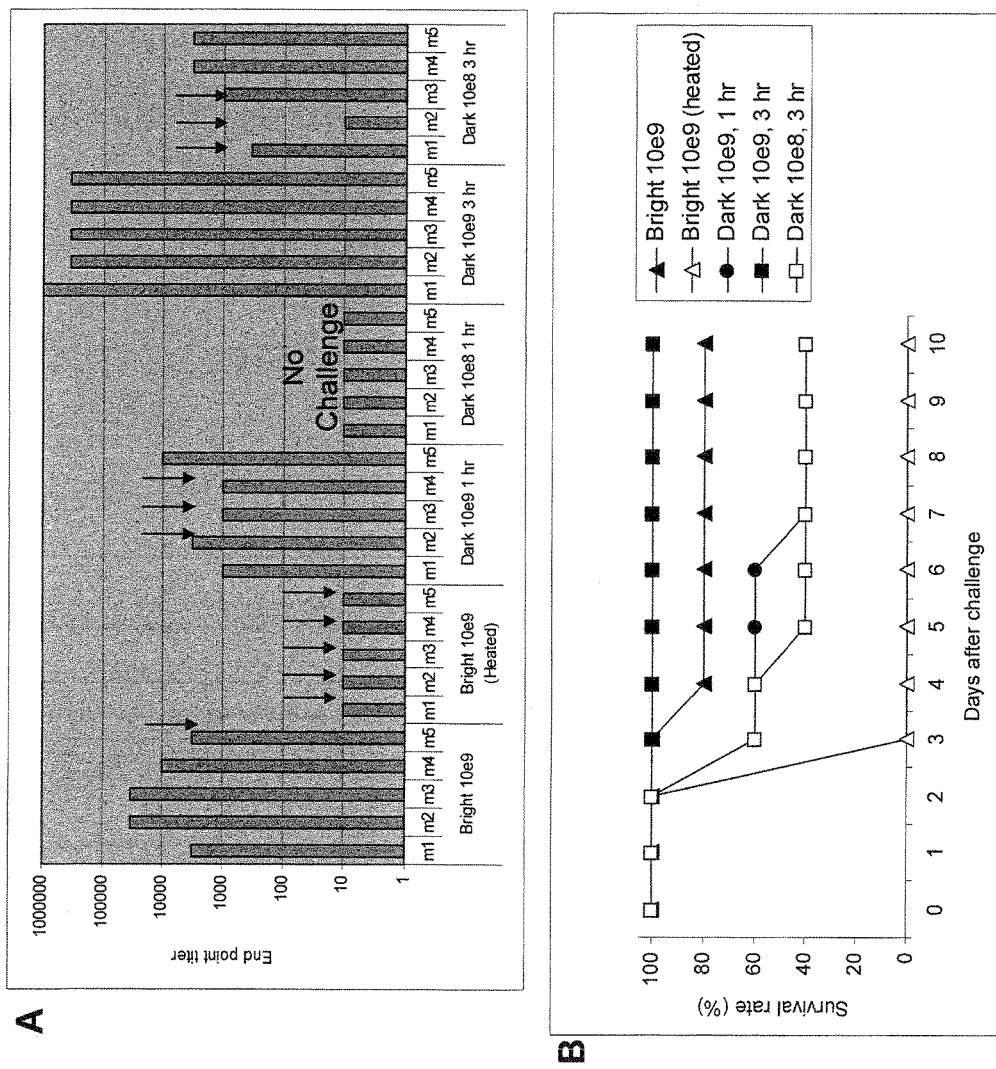
FIG. 13 is a bar graph and a line graph showing a relationship between immunogenicity and germination of BB2646 spores and outgrowth of vegetative cells.

To explore the timing of development of immunogenic vegetative cells from a population of spores, spores of stain BB2646 were heated to 80° C. for 10 min to kill any contaminating vegetative cells and the heated spores were then suspended in LB and incubated at 37° C. At timed intervals samples of the germinating spores were removed and tested for immunogenicity. The data show that unheated spore preparation gave a strong immune response at a dose of $10^9$; heating destroyed immunogenicity (FIG. 13). After 1 hr of incubation at 37° C., an amount of culture equivalent to $10^9$ original spores was highly immunogenic (FIG. 13); microscopic examination revealed that these spores had lost their refractility but had not yet grown out as vegetative cells. After 3 hr in LB, the spore population had been converted almost entirely to vegetative cells. A sample corresponding to $10^9$ original spores generated very high levels of serum antibody and full protection against a tetanus toxin challenge (FIG. 13).

Example 19

Heat Stability of TTFC Expressed in B. Subtilis Vegetative Cells

The rationale for using B. subtilis as a vaccine delivery system is that the spore form of the bacterium is highly resistant to a variety of environmental conditions, including high temperatures, to which conventional vaccines would be very sensitive. Since the active form of the vaccine strain engineered herein was observed to be the vegetative cell rather than the spore, ability of such vaccine strains to survive storage at elevated temperatures was determined. Resistance to high temperatures is particularly important for vaccine distribution and administration in areas of the world that lack consistent and widespread refrigeration.

To evaluate antigenic stability to heating, B. subtilis vegetative cells were incubated at 60° C. for 1 hr in either the wet state (in PBS) or after drying in a Speed-Vac or freeze-drying in a lyophilizer. In the latter cases, cells were resuspended in sterile $H_2O$ after heating.

Figure 14:
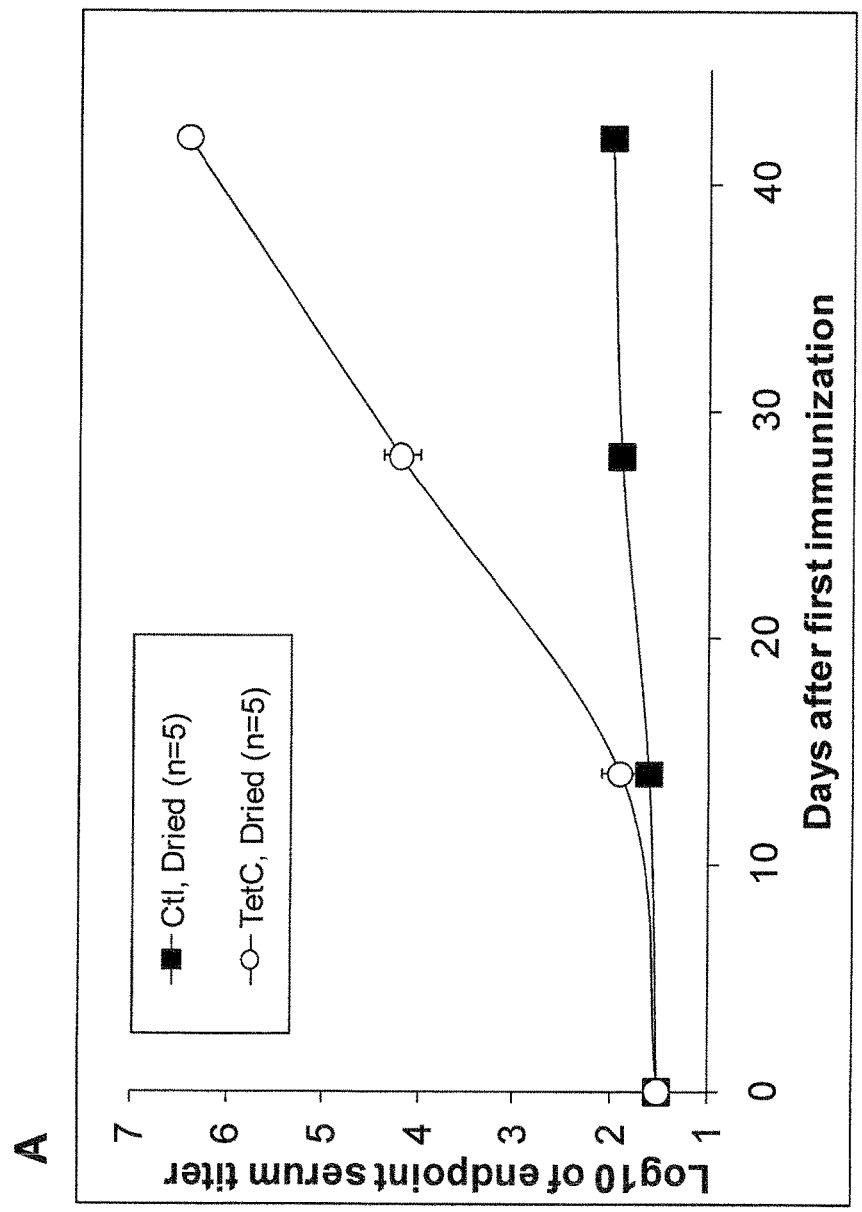
FIG. 14 panel A is a line graph showing serum anti-TetC antibody titers after intranasal immunization of BALB/c mice with dried, heated B. subtilis vegetative cells expressing TTFC cytoplasmically (open circles) or control (closed squares). The dried vegetative cells were treated at 60° C. for 1 hr and resuspended in sterile $H_2O$ before immunization. Mice were inoculated intranasally in a volume of 20 µl per dose on days 0, 14, and 28. Serum titer in mice immunized with TTFC was five orders of magnitude greater than in control mice.
Figure 14:
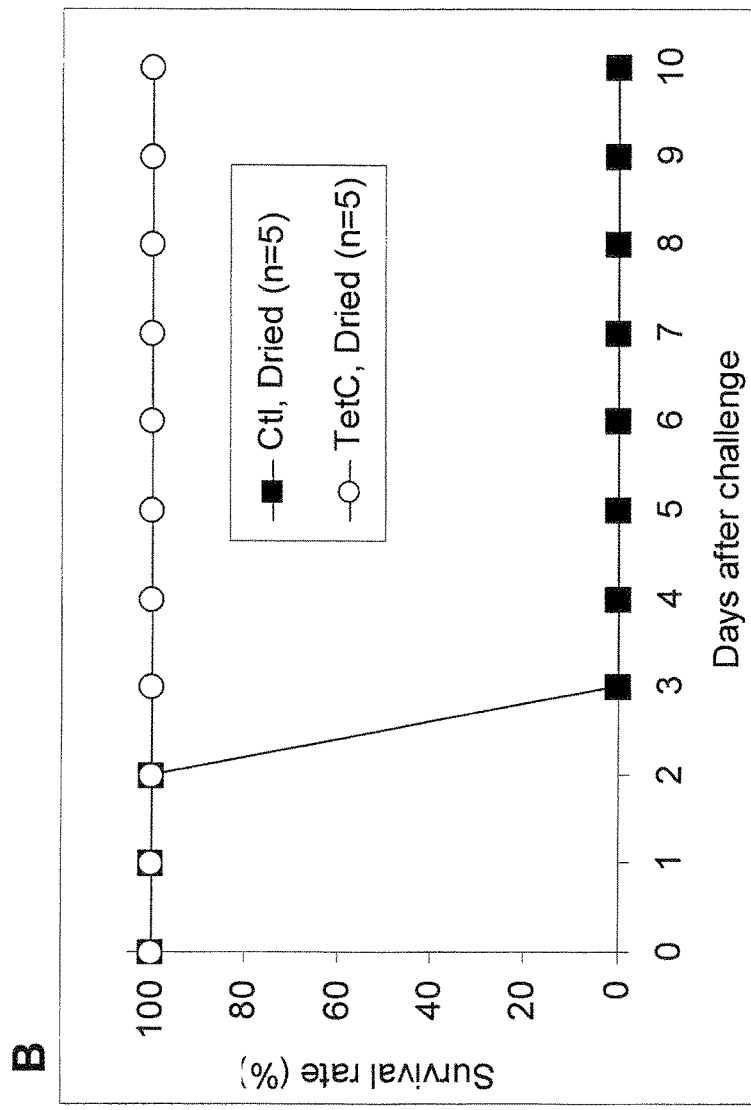

Mice that were immunized with vegetative cells that had been heated to 60° C. in the wet state showed no increase in serum anti-TetC titers and were indistinguishable from mice inoculated with control cells that do not express TTFC (FIG. 14 panel A). When the cells were heated in the dry state, however, very strong immune reactions were generated similar to those obtained with fresh, unheated vegetative cells, demonstrating that the TTFC in dried vegetative cells was still highly immunogenic after heat treatment. The mice immunized with cells that were heated in the dry state were completely protected against lethal tetanus toxin challenge (FIG. 14 panel B).

Figure 15:
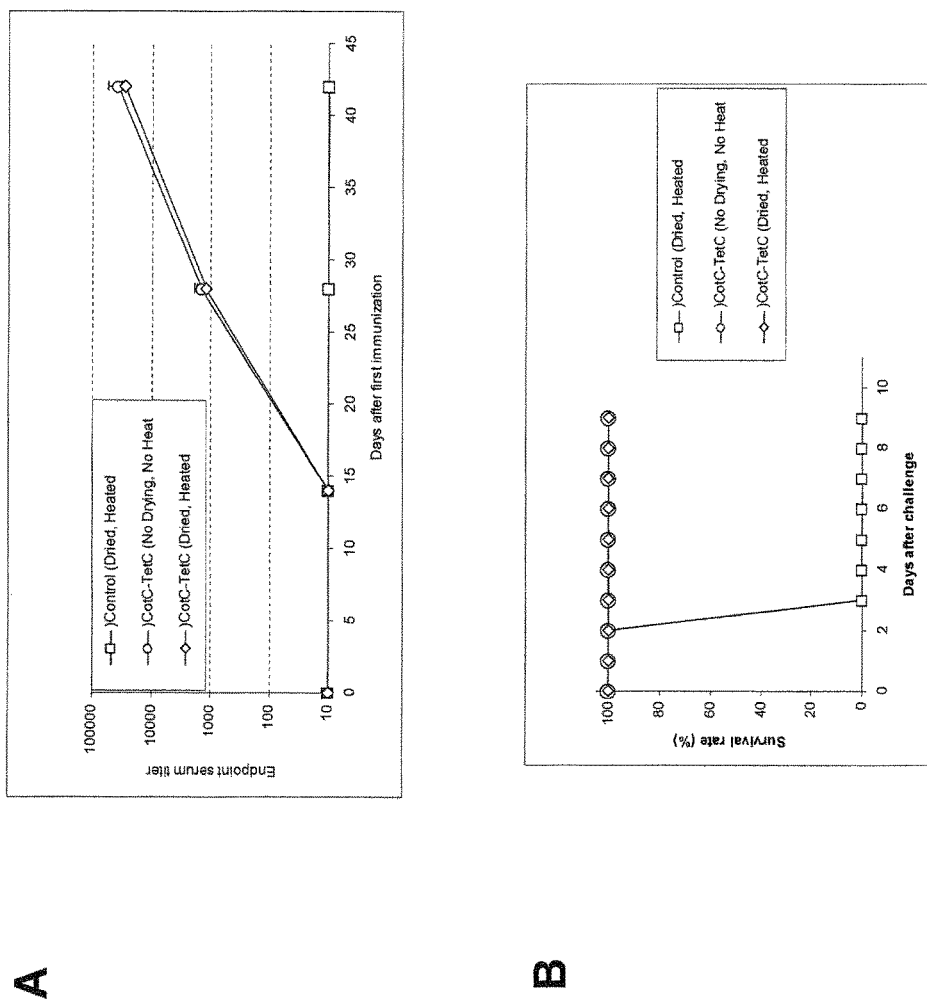
FIG. 15 is a set of line graphs showing serum anti-TetC antibody titers and survival rates in mice after intranasal immunization of BALB/c mice with dried, heated B. subtilis spores displaying TTFC on the spore surface, compared to control spores.

Similar studies were carried out with strain BB2645 that displays the TTFC on the surface of spores by fusion to the spore coat protein CotC. The immunogenicity of dried spores of this strain was entirely resistant to incubation at 60° C. for 60 min (FIG. 15).

Figure 16:
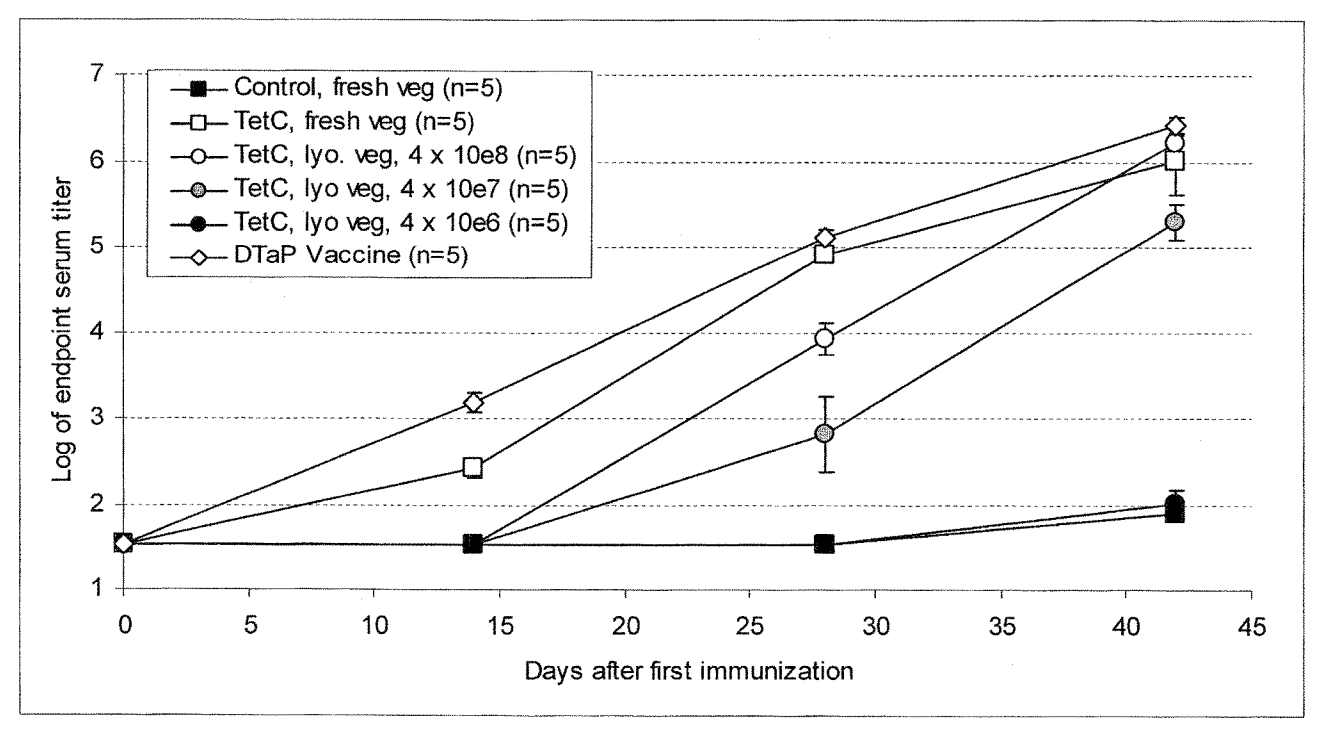
Figure 17:
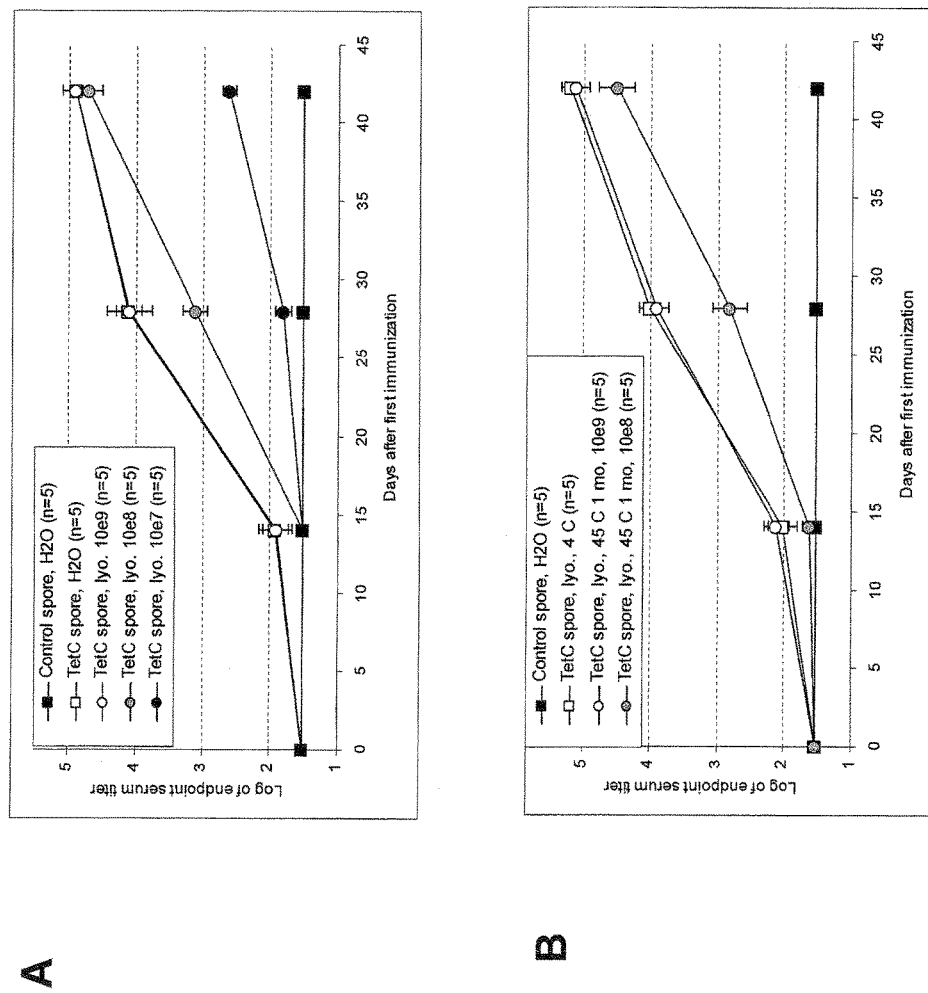
FIG. 17 is a set of line graphs showing antibody development in mice treated with spores incubated at 45° C. for one month (panel B) compared to control (panel A), demonstrating long-term heat stability of strain BB3184, which contains three copies of the cotC-tetC construct.

To assess long-term heat stability at a temperature that is near the limit of ambient conditions anywhere in the inhabited world, the survival of immunogenicity in dried preparations of vegetative cells and spores kept at 45° C. for 30 days was tested. For this example, strains that carried three copies of the Pspac-tetC (BB3059) or cotC-tetC (BB3184) construct were used to increase overall antigen delivery. In both cases, dried cells or spores were completely resistant to high temperature, generating very high serum antibody responses at doses of $10^7$-$10^8$ per round of inoculation (FIGS. 16 and 17).

Example 20

Figure 18:
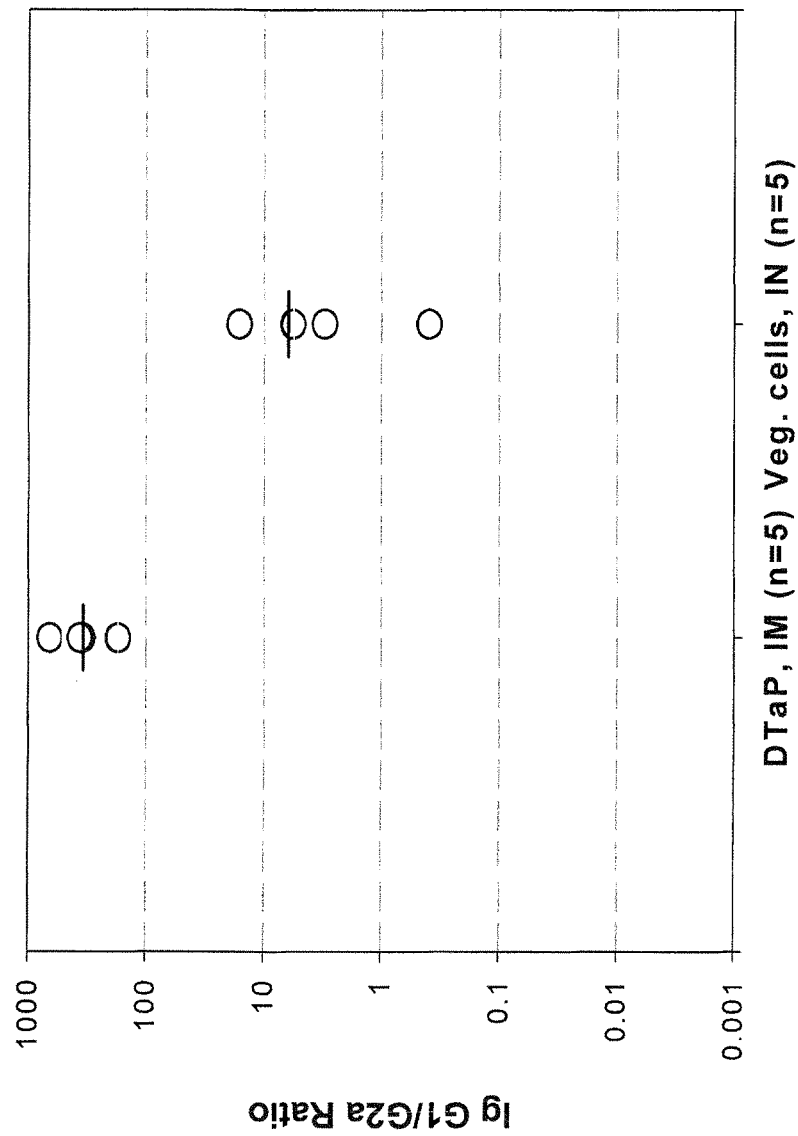

Recombinant B. Subtilis Vegetative Cells Induced a Balanced Th1 and Th2 Immune Response Ratios of IgG2a and IgG1 subclasses in host serum indicate the bias towards a Th1 or Th2 type immune response. Mice inoculated intranasally with recombinant B. subtilis vegetative cells showed increased levels of both IgG1 and IgG2a, giving ratios near unity, whereas the mice receiving the conventional DTaP vaccine given i.m. had increased levels of IgG1 but not of IgG2a, indicative of a Th-2 type immune response (FIG. 18). These results indicate that recombinant B. subtilis vegetative cells induced a balanced immune response.

Example 21

Recombinant B. Subtilis Spores Induced Increased IgA Levels

Figure 19:
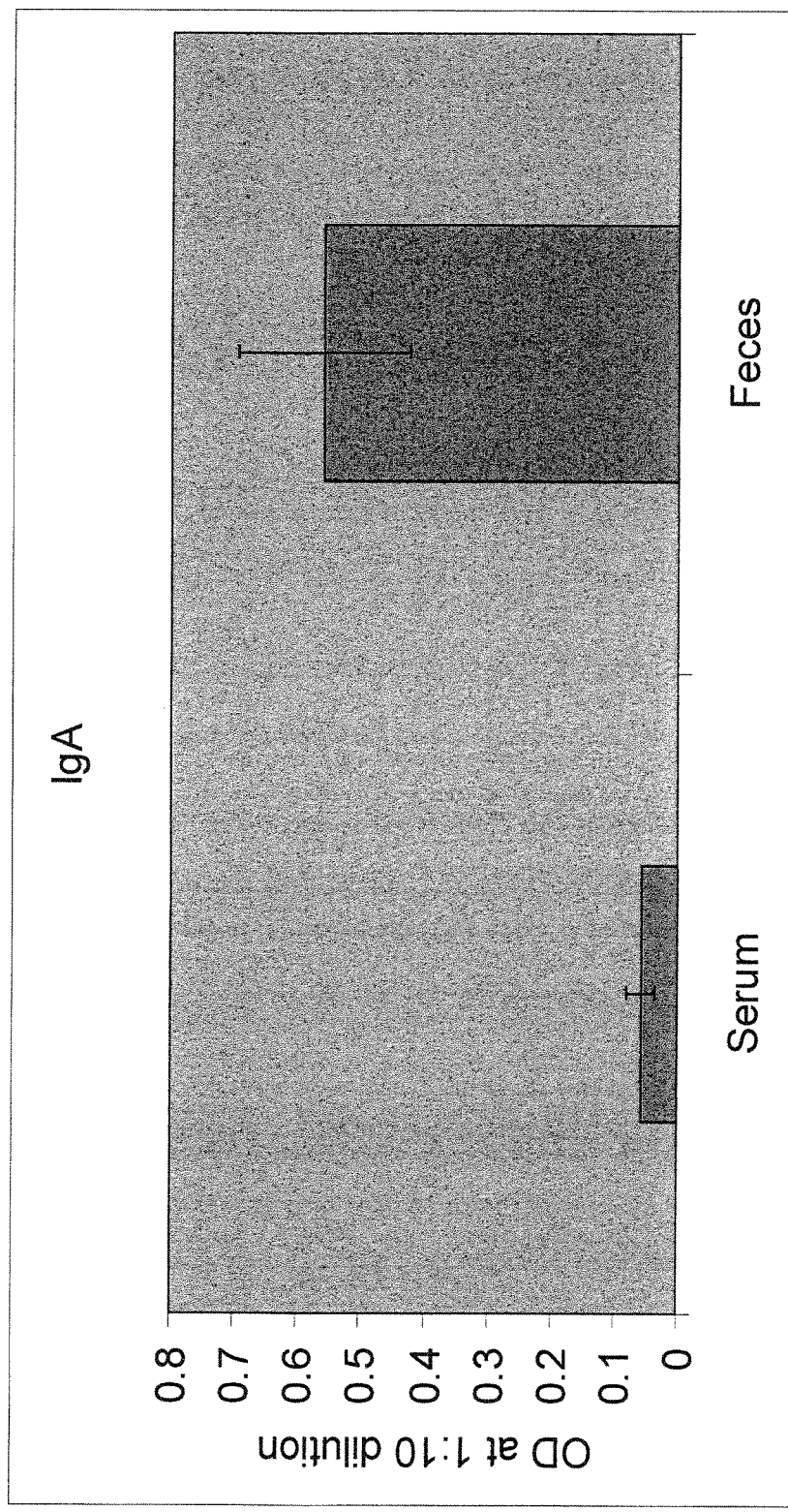
Figure 20:
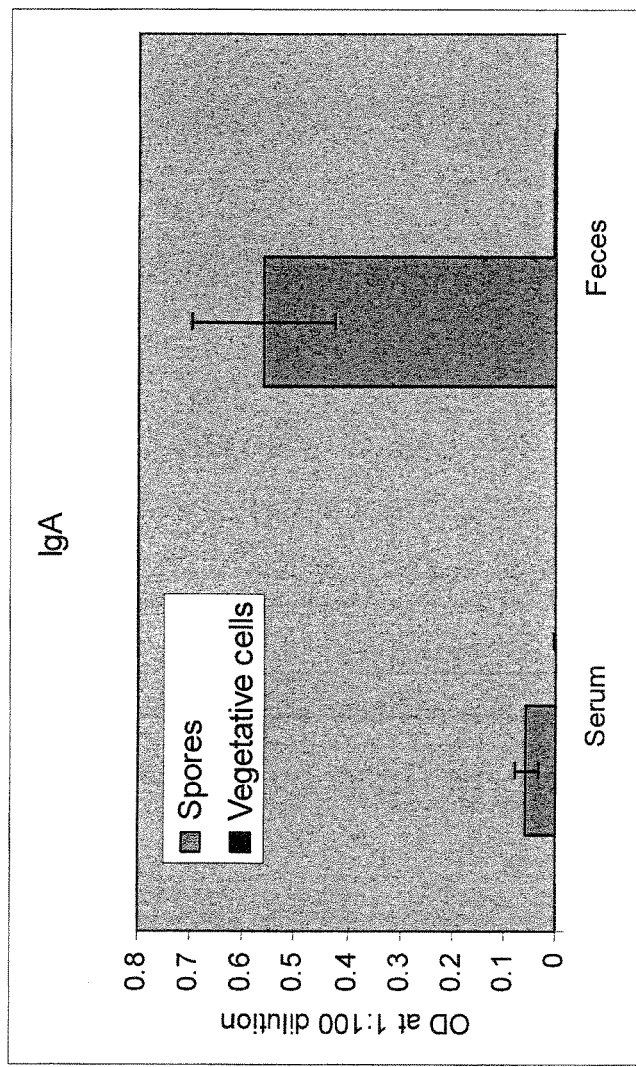
Figure 21:
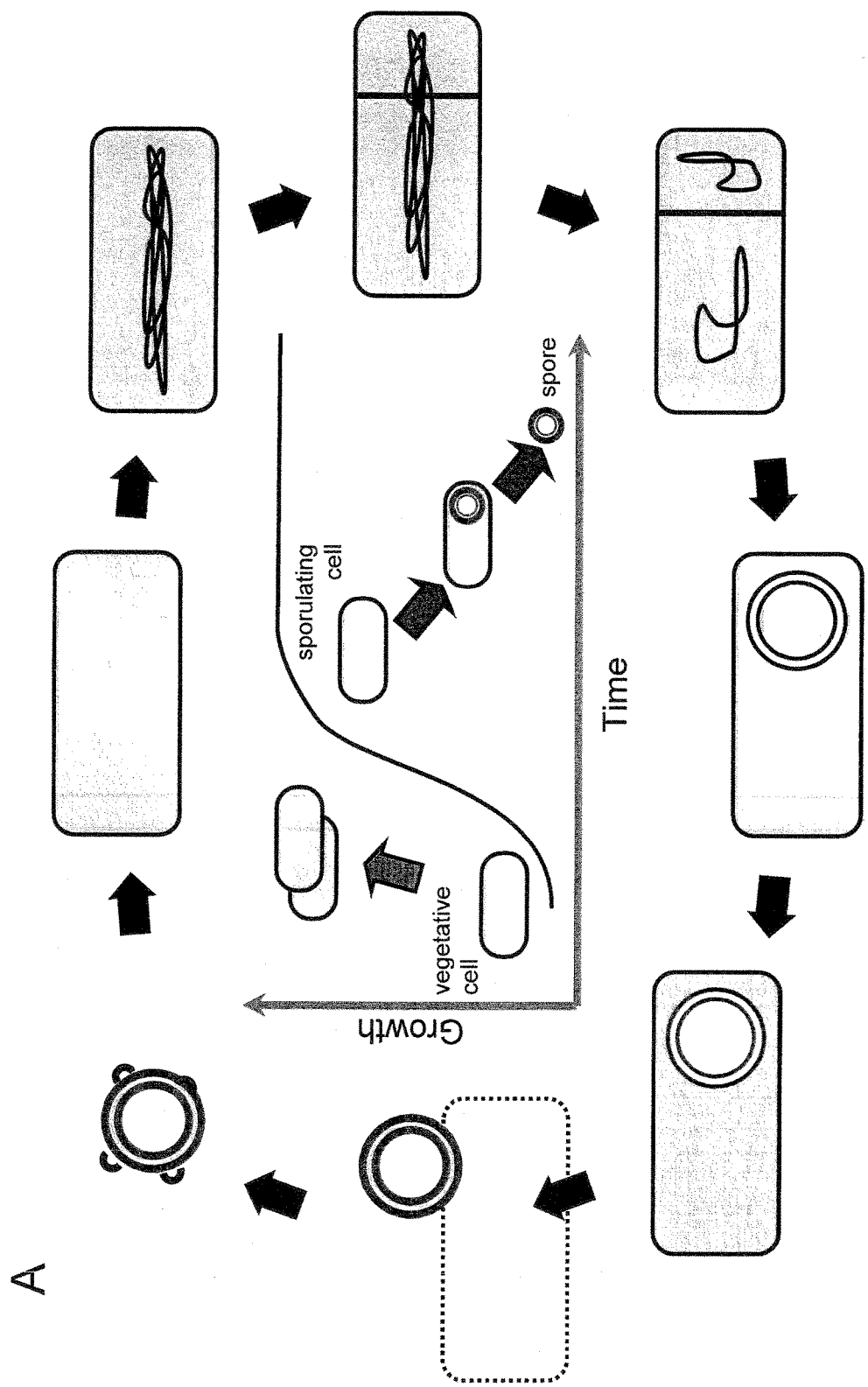
Figure 21:
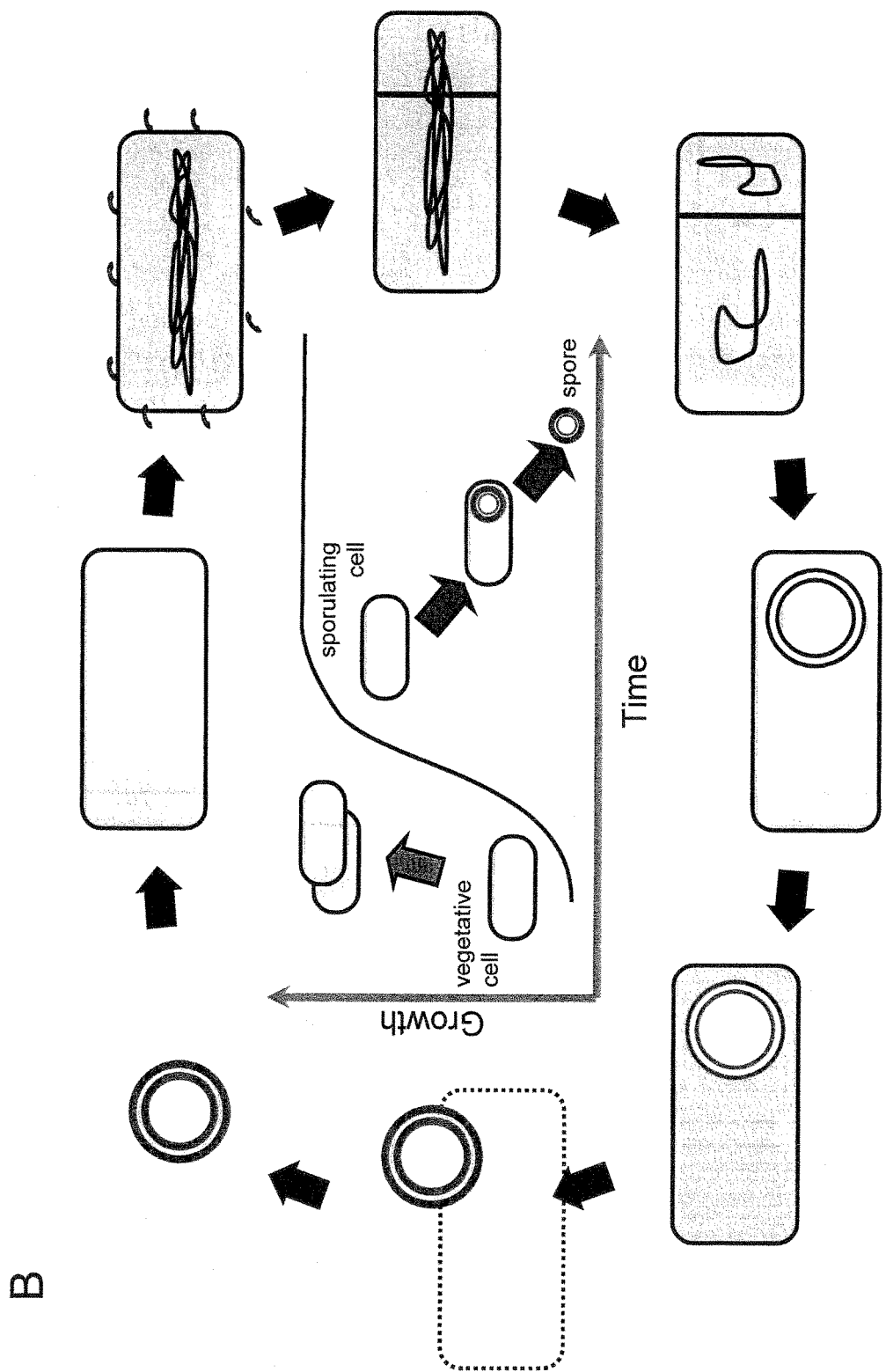
Figure 21:
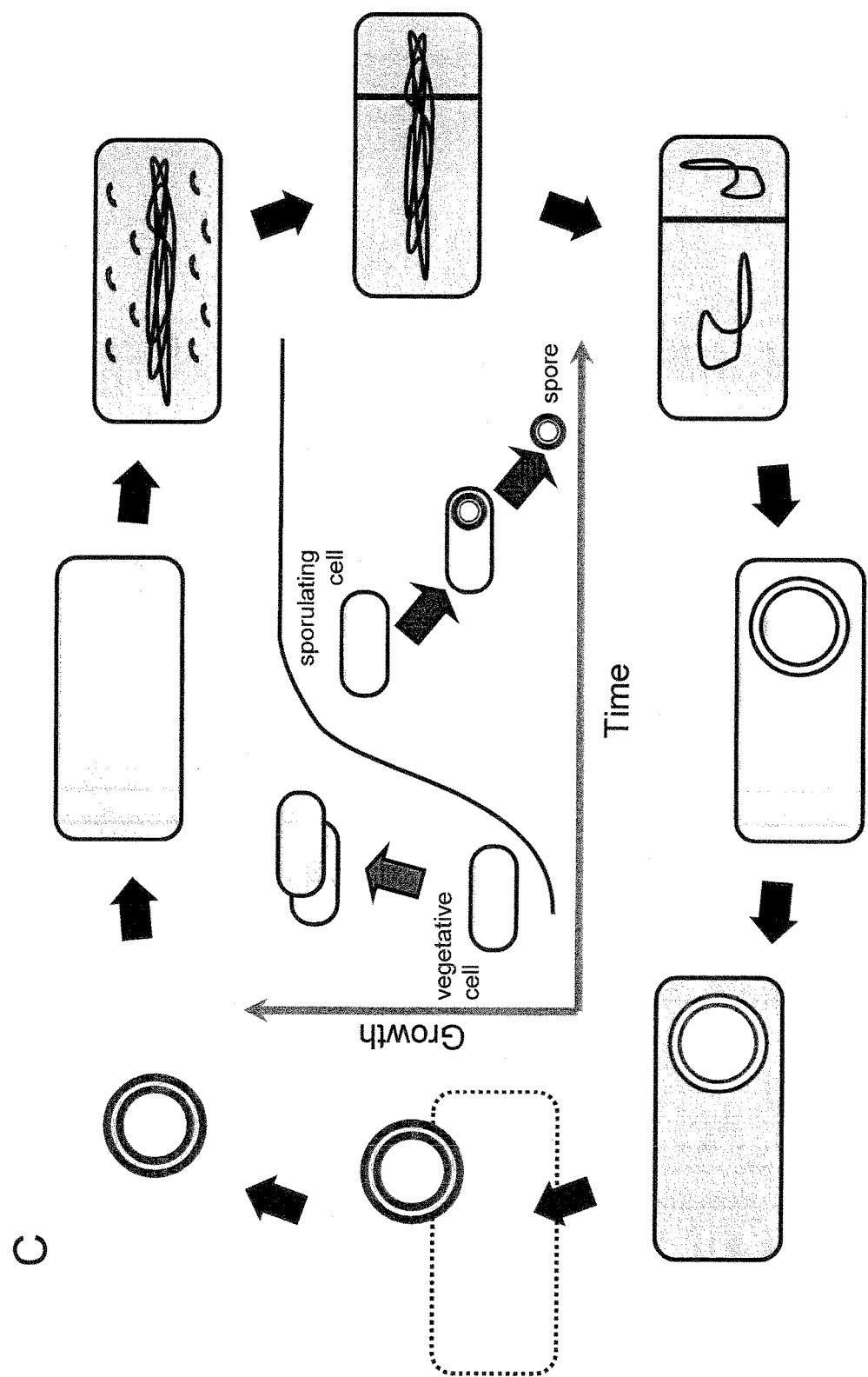
Figure 22:
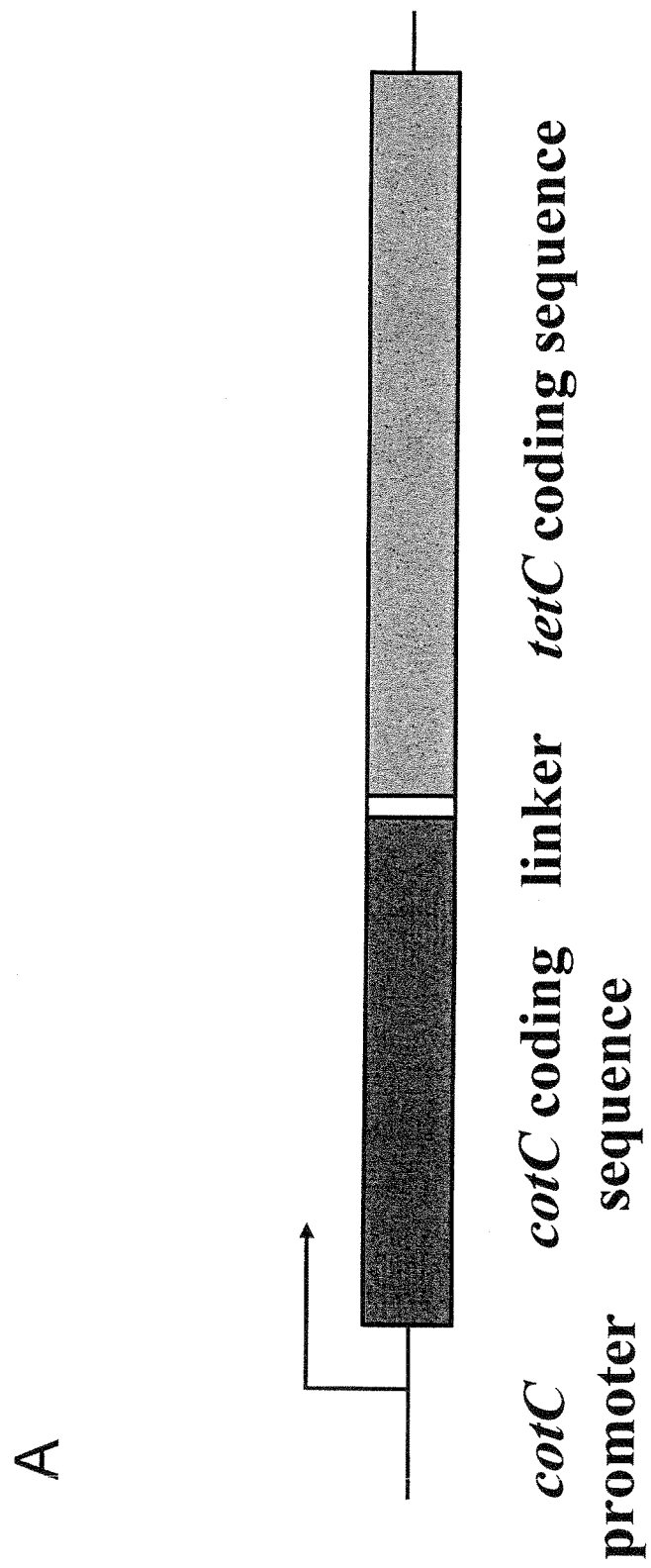
Figure 22:
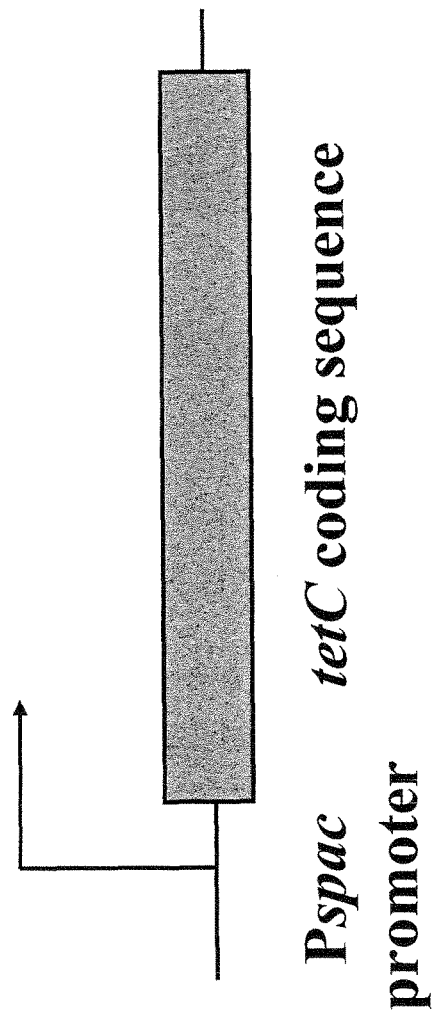

Mice were immunized intranasally with spores of strain BB2666, which expressed bovine VP6 under the control of spat promoter, or the control strain BB2643. See Examples 1 and FIGS. 1-4, and 21. Fecal samples were collected two-weeks after the third round of inoculation and assayed for IgA-type antibodies by ELISA. Mice inoculated with rotavirus vaccine spores showed increased IgA level compared to mice inoculated with control spores (FIGS. 19 and 20).

Example 22

Temperature Stability of B. Subtilis Spores

To test the heat stability of lyophilized B. subtilis spores stored for a period of time, mice were administered intranasally or sublingually with spores and the serum titer was determined.

Figure 23:
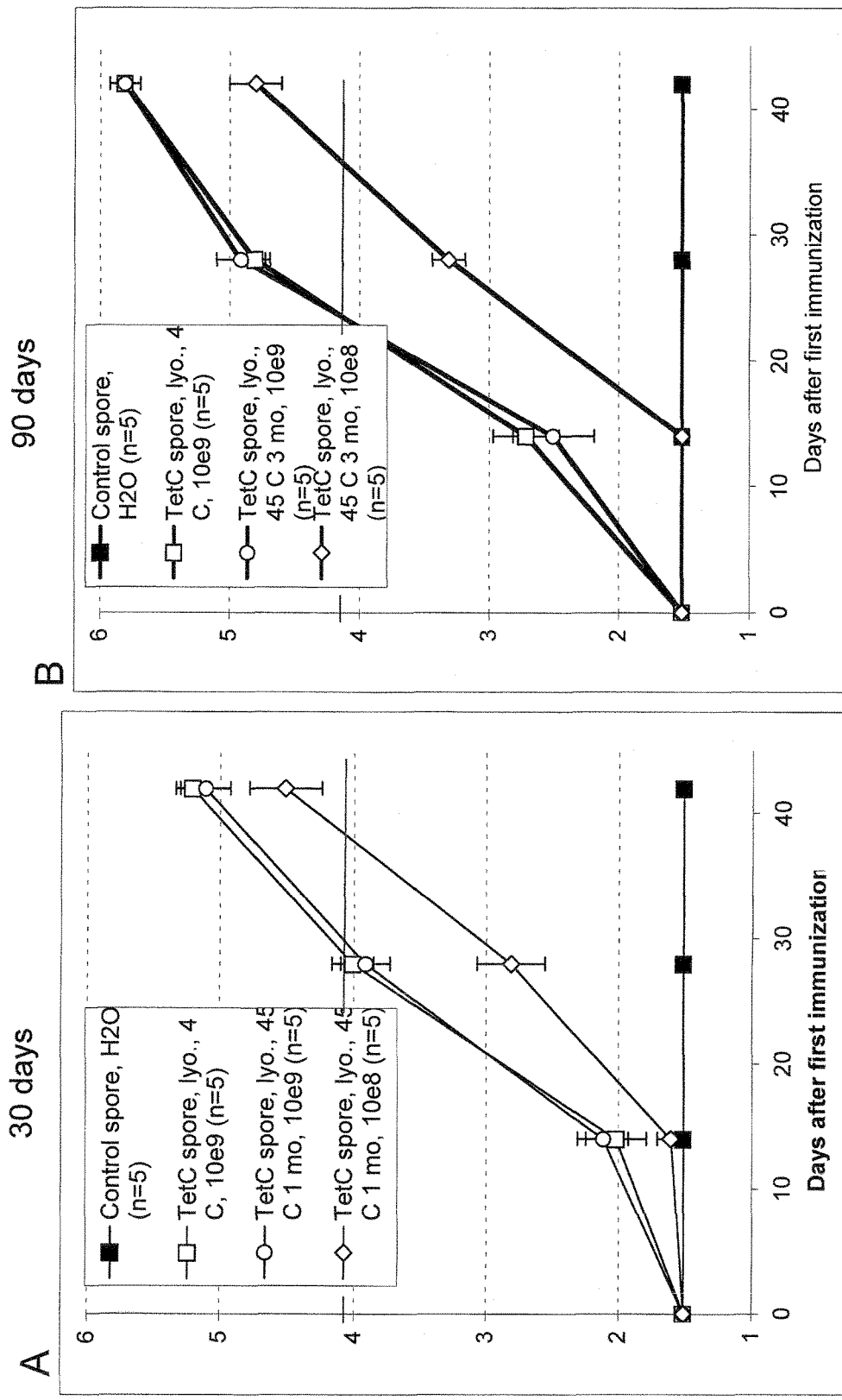
Figure 24:
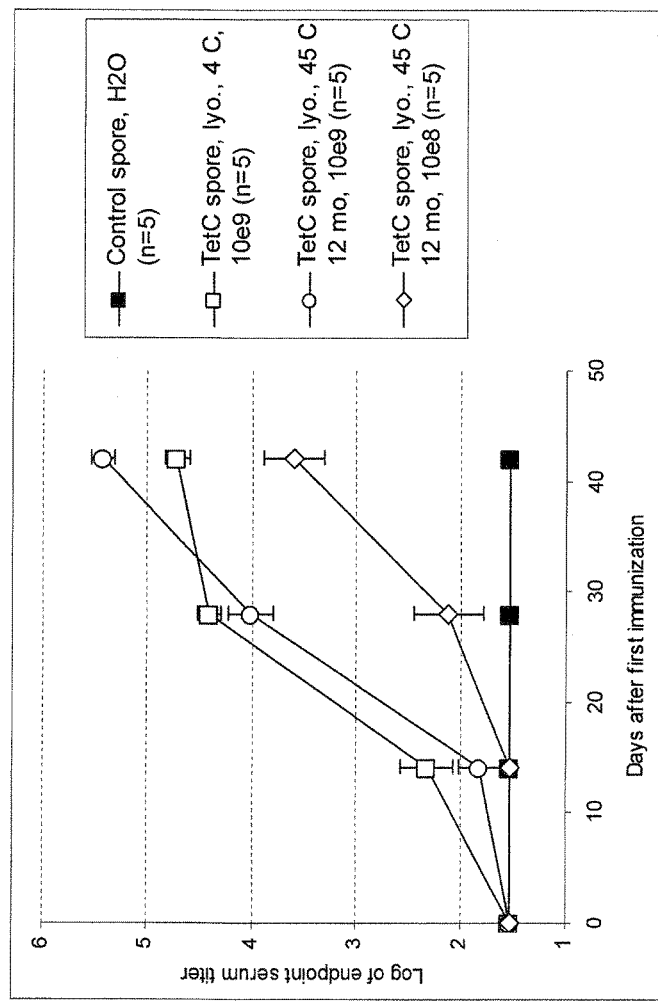

Lyophilized B. subtilis spores BB3184 expressing TetC were lyophilized and stored at 4° C. or 45° C. for 30 days, 90 days, and twelve months. Mice were immunized and serum samples were collected and analyzed for the serum titer. FIG. 23 panels A and B show that the lyophilized B. subtilis spores stored at 4° C. or 45° C. for 30 days and 90 days respectively, produced high serum titer in animals. FIG. 24 shows that lyophilized B. subtilis spores BB3184 stored at 4° C. or 45° C. for twelve months also induced antibody production in animals. Data show that $10^9$ lyophilized B. subtilis spores heated at 45° C. for either 30 days or 90 days induced higher serum titer compared to $10^8$ cells of lyophilized B. subtilis spores incubated at 45° C. for the same amount of time.

Figure 25:
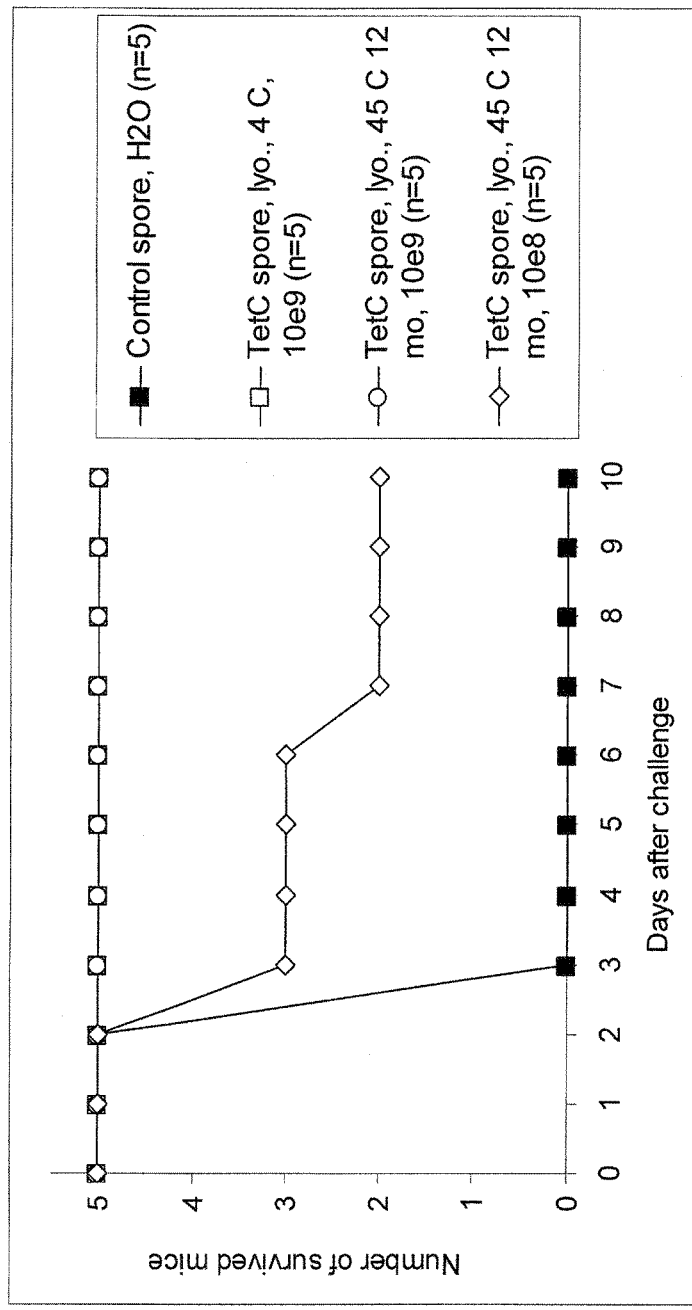

FIG. 25 shows 100% survival rates for subjects immunized with $10^9$ lyophilized B. subtilis spores heated at 45° C. for twelve months or at 4° C. for twelve months. The survival rates for subjects immunized with $10^8$ B. subtilis spores heated at 45° C. for twelve months was 60% three days after challenge, and the survival rate was 40% seven days after challenge Animals immunized with control lyophilized spores died three days after challenge. Thus, the lyophilized B. subtilis spores BB3184 expressing TetC produced antibody production in subjects and were temperature stable vaccines for at least twelve months.

Example 23

Temperature Stability of B. Subtilis Vegetative Cells

Figure 26:
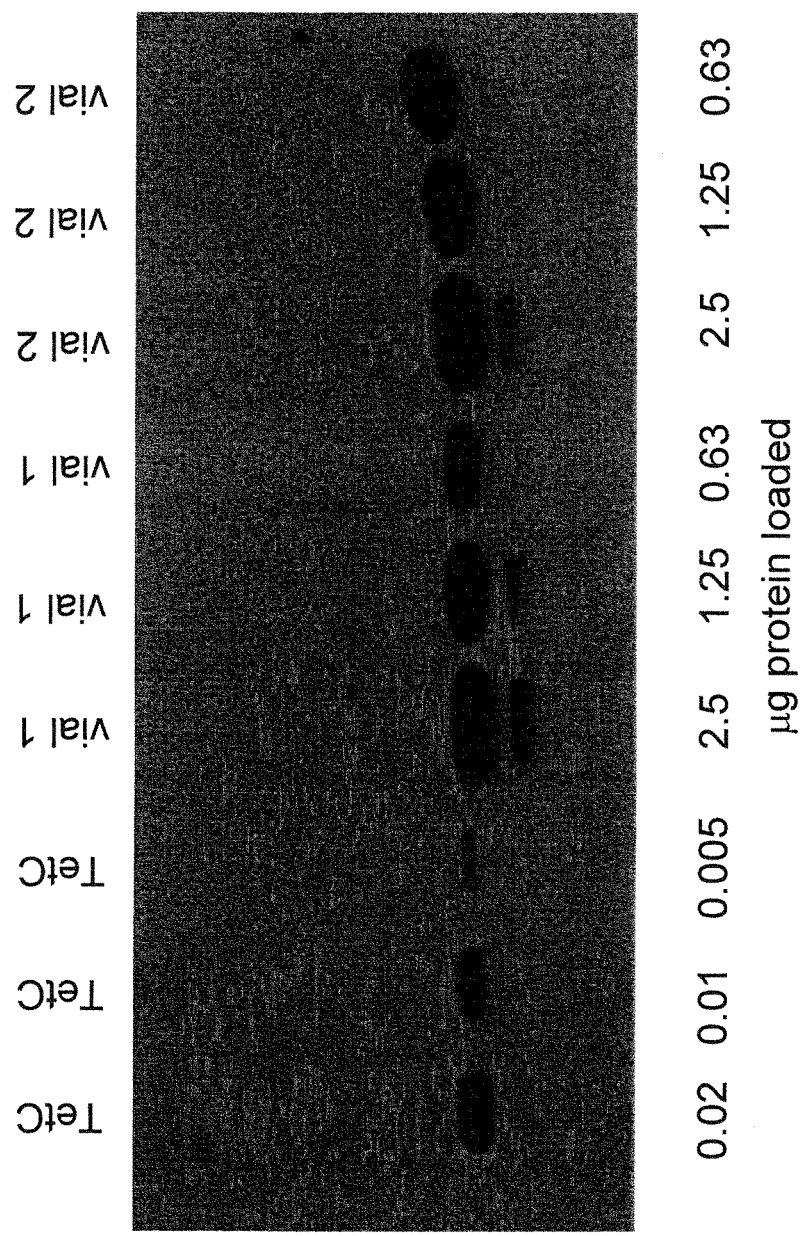
Figure 27:
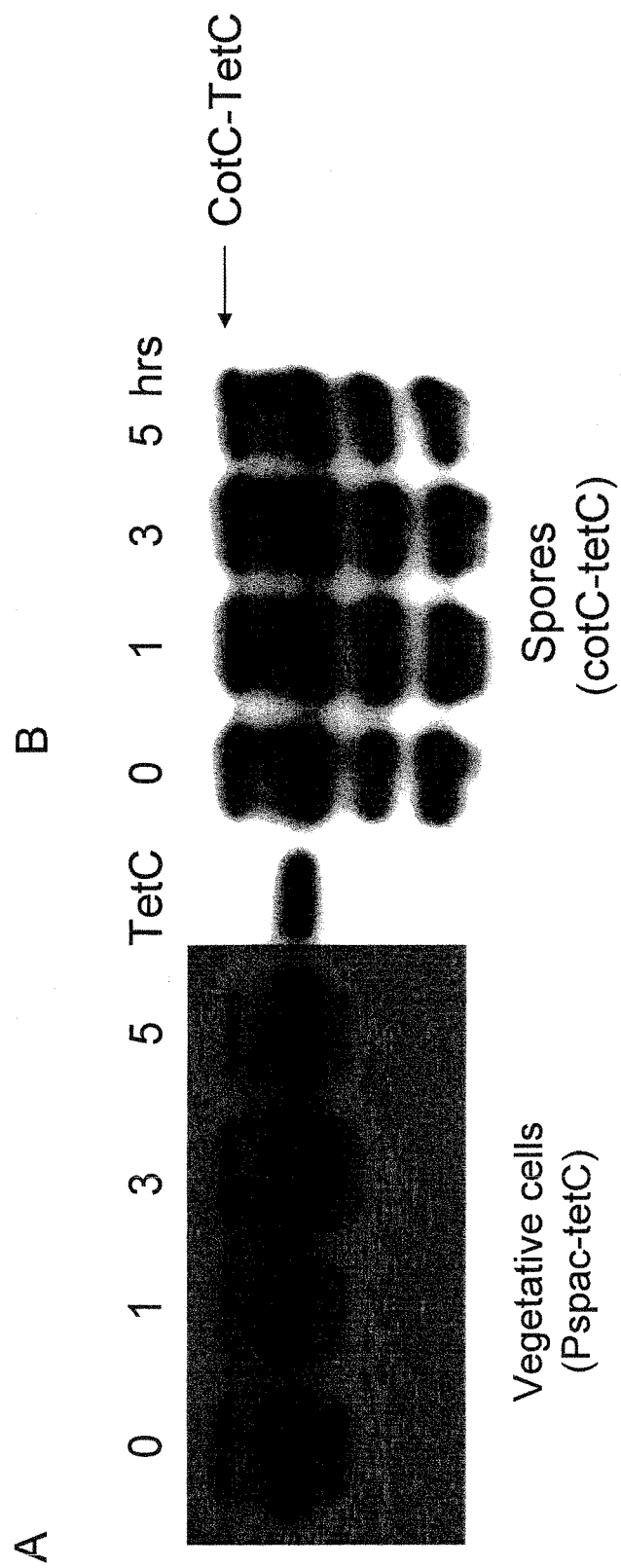

To test the stability of lyophilized B. subtilis vegetative cells expressing TetC, strains were prepared using recombinant methods. FIG. 26 shows that TetC antigen is detectable as a soluble protein in the media of vegetative cells of strain BB3059 which expresses TetC under the control of Pspac promoter. TetC antigen represents about 3% of total soluble protein in vegetative cells BB3059. FIG. 27 shows a Western blot and Coomassie blue-stained gel showing expression of TetC antigen in each of a recombinant B. subtilis vegetative cell strain producing toxin antigen under regulation of the IPTG-inducible Pspac, and in B. subtilis spores as fusion cotC-TetC. These vegetative cells and spores were incubated for at least five hours at 37° C. Thus, lyophilized *B. subtilis* spores BB3184 and lyophilized *B. subtilis* vegetative cells BB3059 display or express antigen that can be detected by assays.

Figure 28:
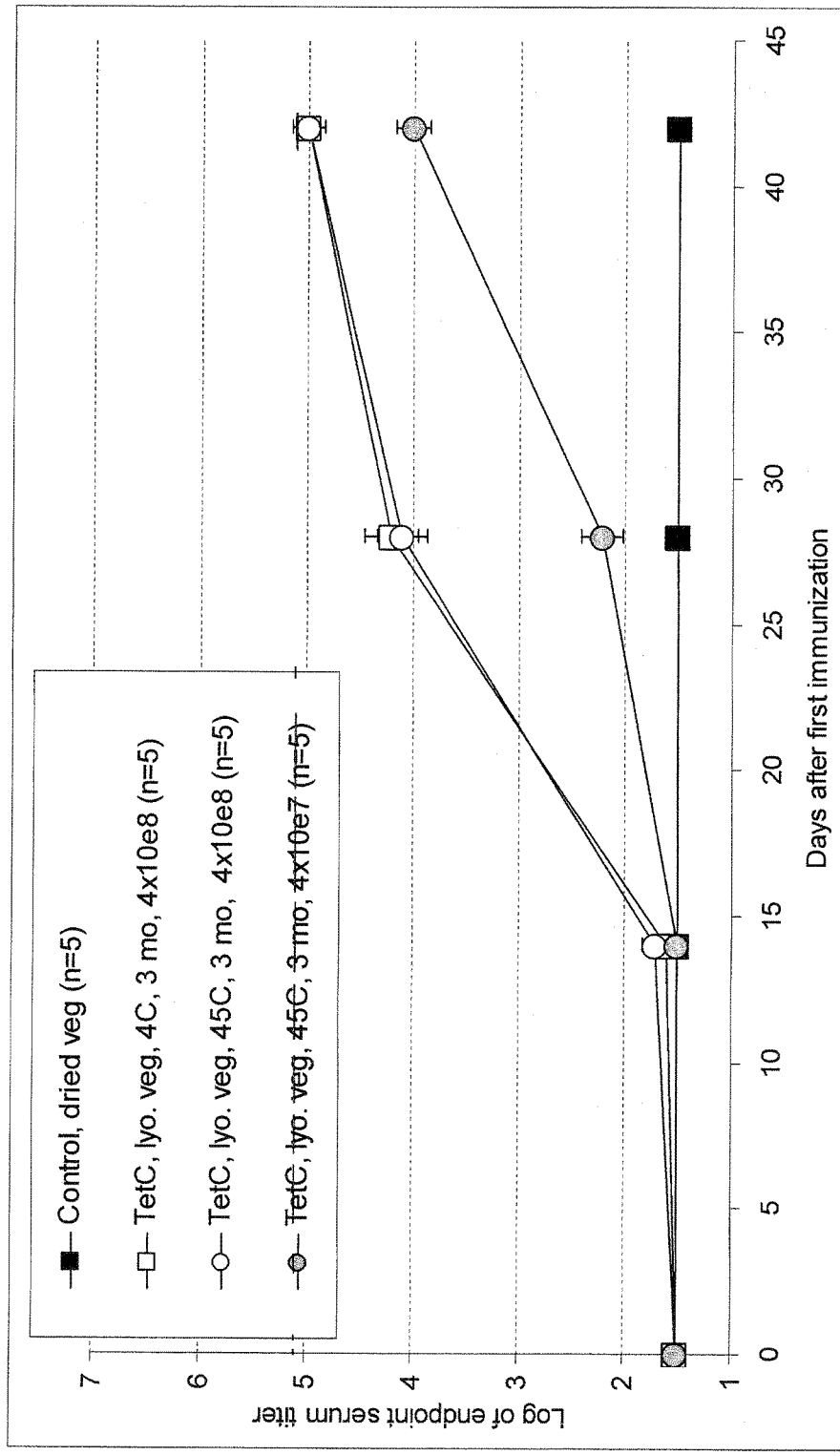

Lyophilized *B. subtilis* vegetative cells BB3059 expressing TetC cytoplasmically and control lyophilized *B. subtilis* vegetative cells BB 2643 were also lyophilized and stored at either 4° C. or 45° C. FIG. 28 panels A and B show that lyophilized *B. subtilis* vegetative cells expressing TetC stored at 4° C. and 45° C. for 90 days induced high serum titer in murine subjects and provided protective immunogenicity to the subjects. FIG. 29 panel A shows that lyophilized *B. subtilis* vegetative cells stored at 4° C. or 45° C. for twelve months induced comparable serum titer in the subjects. These figures show that increased concentration of the lyophilized vegetative cells expressing TetC increased the extent of protective immunogenicity.

FIG. 29 panel B shows 100% survival for murine subjects inoculated with lyophilized *B. subtilis* vegetative cells BB3059 expressing TetC, including those vegetative cells expressing TetC and stored at 4° C. or 45° C. for 12 months. FIG. 29 panel B also shows that subjects immunized with control vegetative cells died three days after challenge.

To further analyze the protective immunogenicity of dried lyophilized *B. subtilis* vegetative cells BB3059 expressing TetC, cells were stored at 45° C. for 17 months and used to immunize subjects. Groups of mice were immunized ($2\times10^8$ cells per dose) either intranasally with the lyophilized *B. subtilis* vegetative cells BB3059, sublingually with lyophilized *B. subtilis* vegetative cells BB3059, or intranasally with control lyophilized *B. subtilis* vegetative cells BB2643 lacking the TetC coding sequence. Sublingual administration involved sedating the subjects then placing 20 µL of the material under the tongue of each subject. This sublingual administration procedure was used in subsequent examples unless otherwise indicated.

Figure 30:
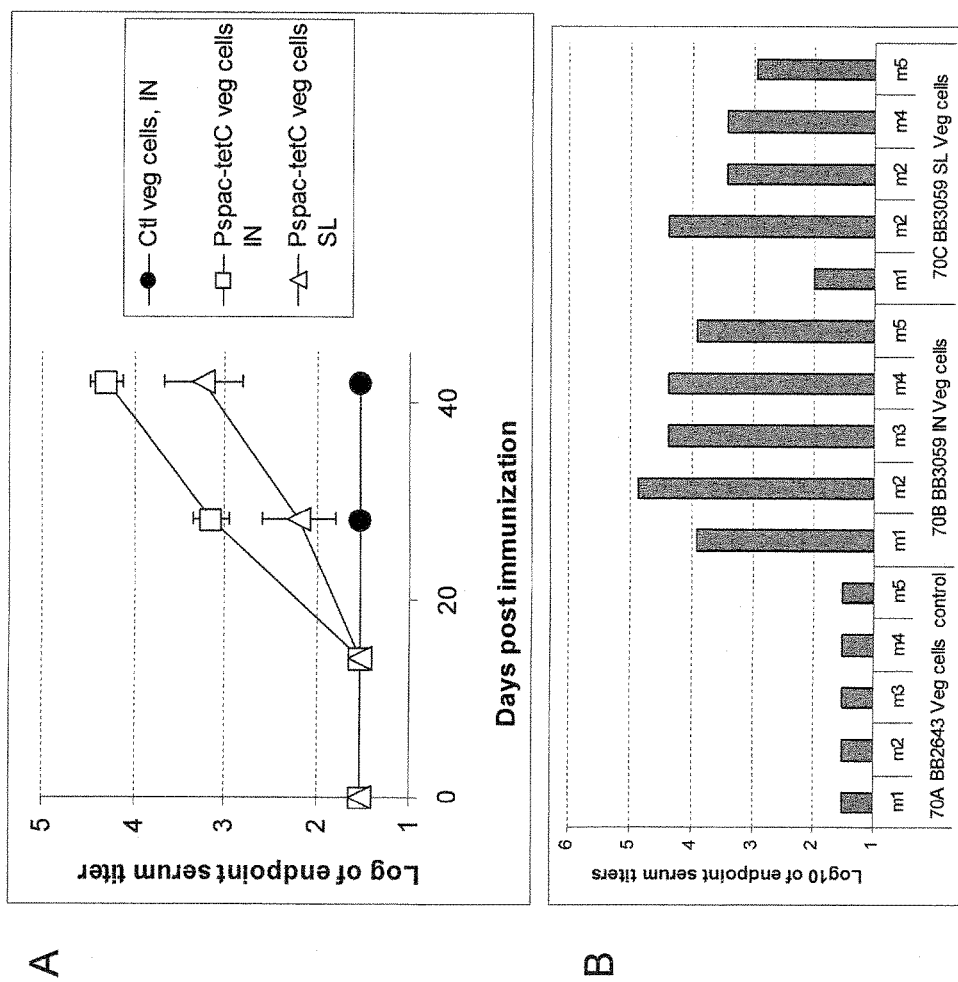

FIG. 30 panel A shows the average amount of serum anti-TetC antibodies detected in the subjects as a function of time (days) after the immunization. Subjects inoculated intranasally with lyophilized *B. subtilis* vegetative cells expressing TetC and mice inoculated sublingually with lyophilized *B. subtilis* vegetative cells expressing TetC showed orders of magnitude greater serum antibody titer than mice intranasally immunized with control lyophilized *B. subtilis* vegetative cells BB2643 (FIG. 30 panel A).

Ability of the lyophilized BB3059 vegetative cells to immunize individual mice after intranasal or sublingual inoculation was also determined and is shown in FIG. 30 panel B. Higher levels of serum anti-TetC antibodies were detected in individual mice intranasally or sublingually immunized with lyophilized *B. subtilis* vegetative cells BB3059 compared to mice immunized with control cells.

Thus, dried lyophilized *B. subtilis* vegetative cells BB3059 expressing TetC were heat-stable and effective vaccines.

Example 24

Analysis of Lyophilized *B. Subtilis* Spores and Vegetative Cells

Figure 32:
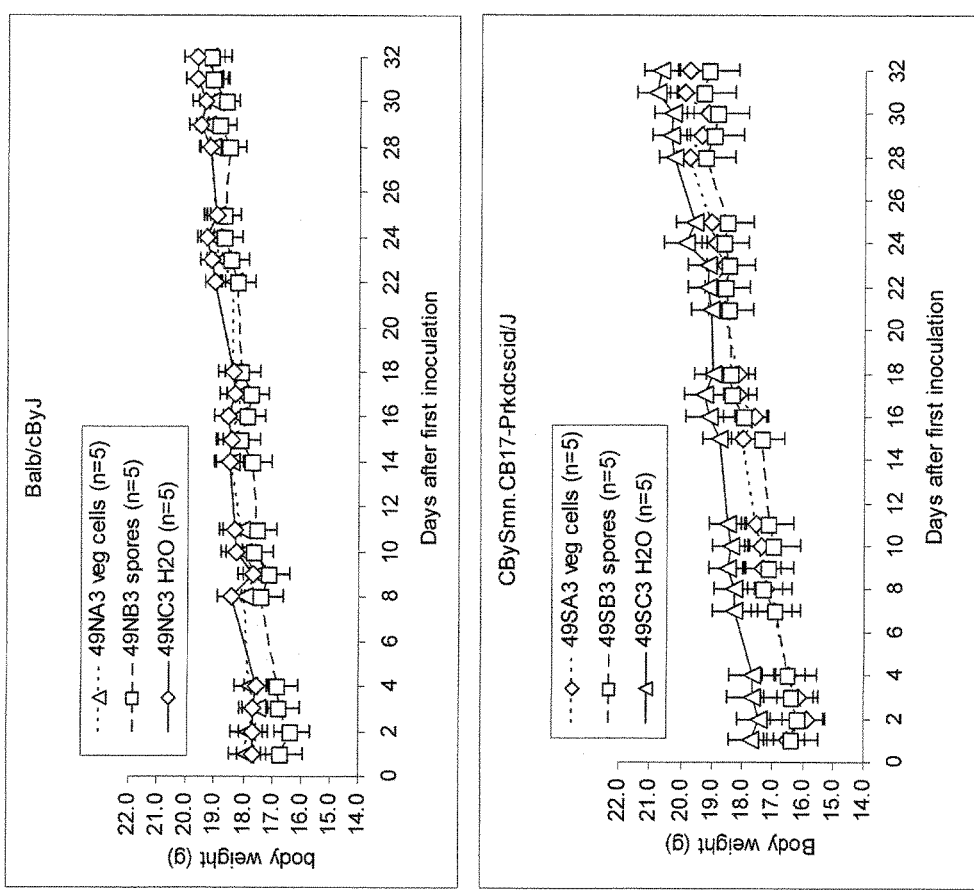

FIG. 31 is a chart showing the safety and vaccination steps used for normal mice and SCID in an analysis performed to determine the effectiveness of the vaccination spores and vegetative cells. Five mice were terminated three days after every immunization and their olfactory lobes, cerebrum, lung, and nasal epithelium including the nasal-associated lymphoid tissue (NALT) were examined. Immunized subjects were found to have normal tissue morphology indicative of protective immunogenicity. Subject body weight was also monitored daily as shown in FIG. 32.

Data show that vaccines were heat stable and fully protective and provided systemic immunity against tetanus when administered intranasally or mucosally. Serum antibody titer values were greater than 30,000 which correlated with 100% protection against two times the lethal amount of tetanus toxin. Serum titer of greater than 10,000 correlating generally with about 80% protection. Further analysis was performed on the vaccines to further optimize the methods and compositions shown herein.

Example 25

Sublingual Administration of Lyophilized *B. Subtilis* Vegetative Cells with mLT Adjuvant To evaluate the effect of mLT adjuvant on serum titer and survival rates, mice were sublingually immunized with lyophilized *B. subtilis* vegetative cells BB3059 expressing cotC-TetC (with or without adjuvant) and control vegetative cells BB2643.

Figure 33:
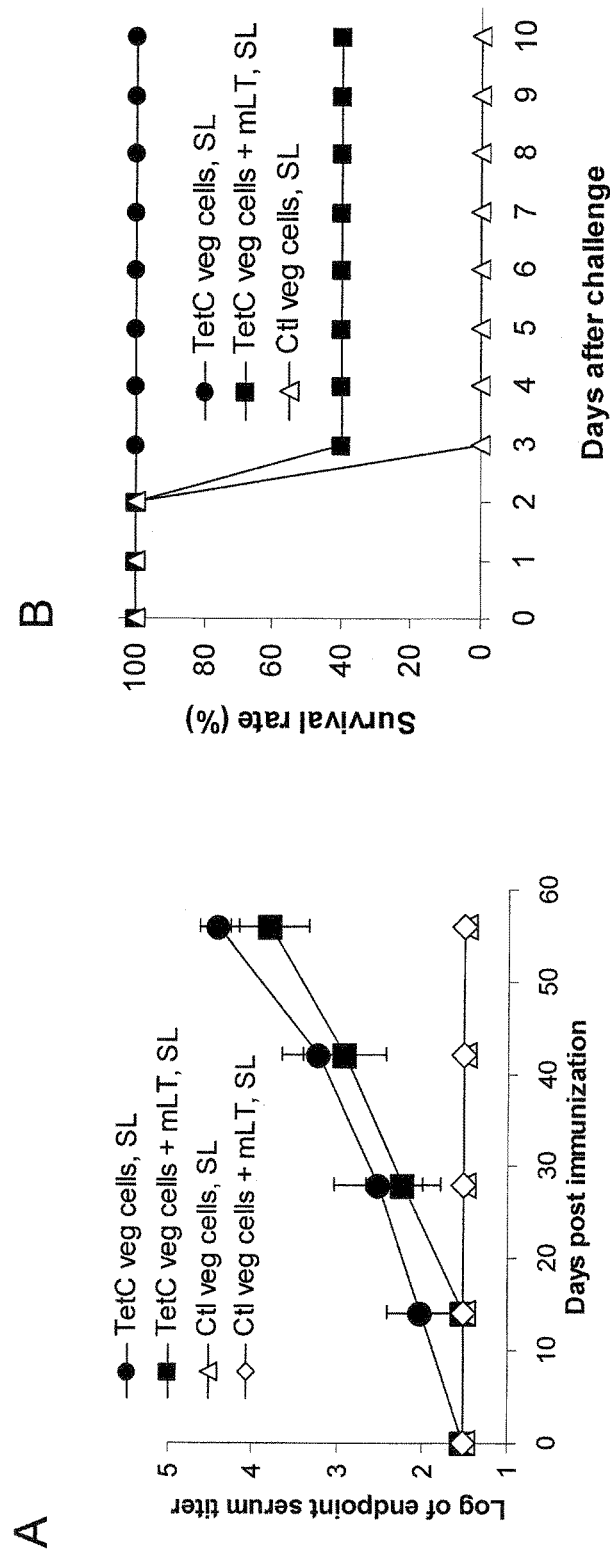

Serum samples were collected after inoculation and assayed by ELISA for serum titer. FIG. 33 panel A shows that regardless of presence of mLT adjuvant, mice inoculated with lyophilized *B. subtilis* vegetative cells BB3059 expressing TetC showed higher serum titer compared to mice inoculated with control vegetative cells. FIG. 33 panel B shows 100% survival for murine subjects sublingually immunized with lyophilized *B. subtilis* vegetative cells BB3059 expressing TetC, compared to 40% for subjects sublingually immunized with lyophilized. *B. subtilis* vegetative cells BB3059 expressing TetC and mLT adjuvant. Subjects sublingually immunized control lyophilized *B. subtilis* vegetative cells BB2643 died three days after challenge.

Example 26

Sublingual Administration of Lyophilized *B. Subtilis* Vegetative Cells and Purified Recombinant TetC Mice were sublingually immunized with lyophilized *B. subtilis* BB3059 expressing TetC (with or without adjuvant), a purified recombinant TetC fragment or a control vegetative cells BB2643 to compare serum titer and survival rates.

Figure 34:
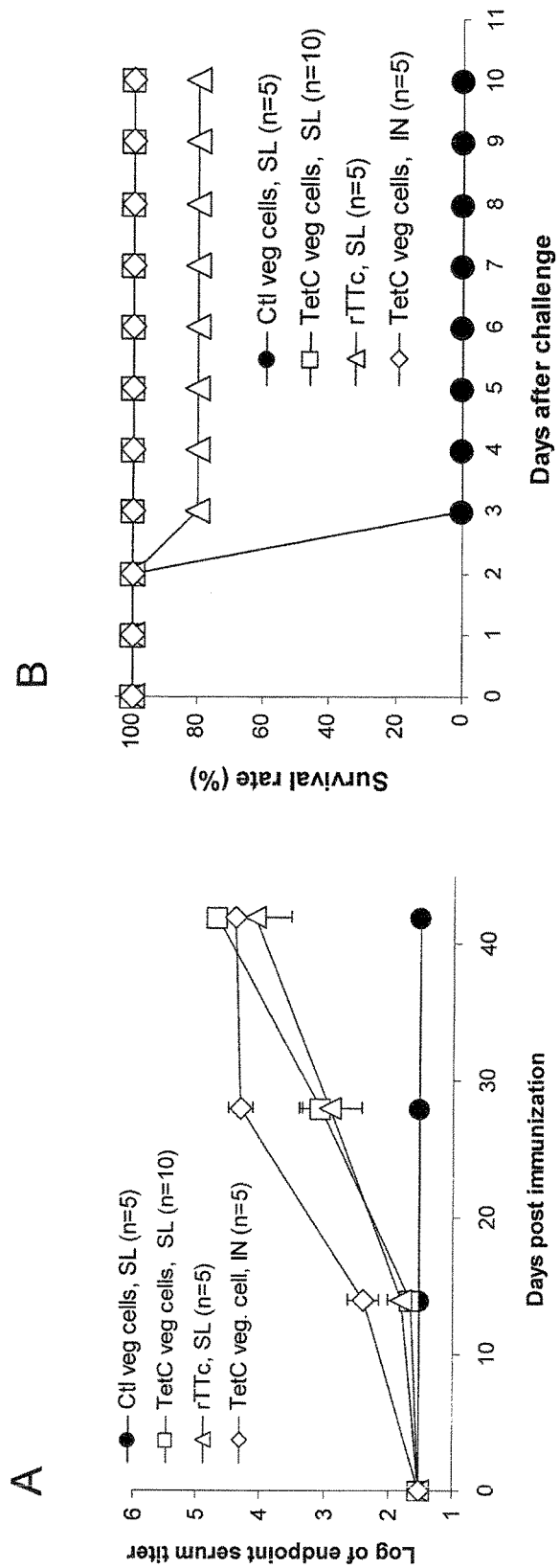

FIG. 34 panel A shows comparable serum titer values for subjects immunized intranasally with lyophilized *B. subtilis* vegetative cells BB3059 expressing TetC, subjects immunized sublingually with lyophilized *B. subtilis* vegetative cells BB3059 expressing TetC, and subjects immunized sublingually with recombinant TetC fragment.

Data in FIG. 34 panel B shows 100% survival for tetanus challenged subjects immunized either intranasally or sublingually with lyophilized *B. subtilis* vegetative cells BB3059 expressing TetC. Subjects immunized sublingually with purified recombinant TetC fragment were observed to have 80% survival three days after immunization. Subjects immunized with control vegetative cells died three days after challenge.

Example 27

Lyophilized *B. Subtilis* Vegetative Cells Expressing TetC Induced a Balanced Th1 and Th2 Immune Response To further investigate the effect administering lyophilized *B. subtilis* vegetative cells expressing TetC has on the immune response, serum from immunized mice were analyzed for IgG1 and IgG2a. Subjects were immunized sublingually with lyophilized *B. subtilis* vegetative cells BB3059 expressing TetC; intranasally with lyophilized *B. subtilis* vegetative cells BB3059 expressing TetC; sublingually with purified recombinant TetC fragment; or intramuscularly with a commercial vaccine for diphtheria, tetanus and pertussis (DTAP; Tripedia®, Sanofi Pasteur Inc., Swiftwater, Pa., USA).

Figure 35:
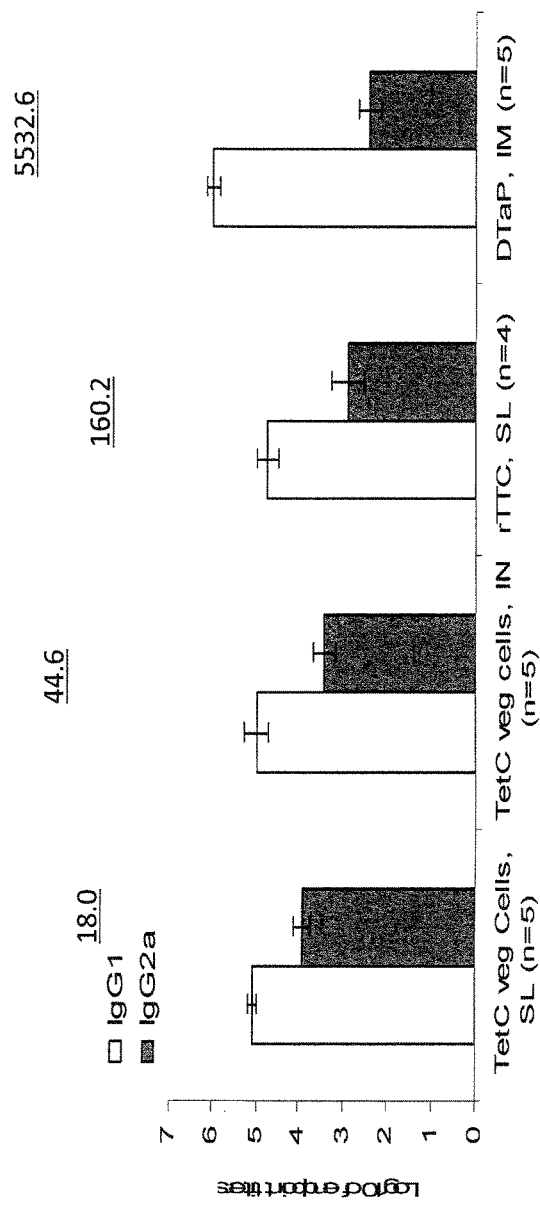

FIG. 35 shows that mice inoculated intranasally or sublingually with recombinant lyophilized *B. subtilis* vegetative cells BB3059 were observed to have very similar levels of IgG1 and IgG2a. The subjects inoculated sublingually with strain BB3059 had a ratio of IgG1 and IgG2a of 18, and subjects inoculated intranasally with strain BB3059 had a ratio of IgG1 and IgG2a of 44.6. The ratio of IgG1 and IgG2a was much more disproportionate for the subjects immunized sublingually with recombinant TetC fragment (160.2) and intramuscularly with the DTaP vaccine (5532.6). The increased ratio of IgG1 compared to IgG2a is indicative of a disproportionate Th-2 type immune response instead of a balanced Th-1 and Th-2 response. Thus data show that intranasally and sublingually administered *B. subtilis* vegetative cells expressing TetC induced a more balanced Th-1 and Th-2 immune response than a recombinant TetC fragment and a commercially available DTAP vaccine.

Example 28

Cytokines Induced by Lyophilized *B. Subtilis* Vegetative Cells Expressing TetC

Serum cytokines induced by inoculation with lyophilized *B. subtilis* vegetative cells BB3059 expressing TetC were also analyzed and compared to results for commercially available DTaP vaccine.

Figure 36:
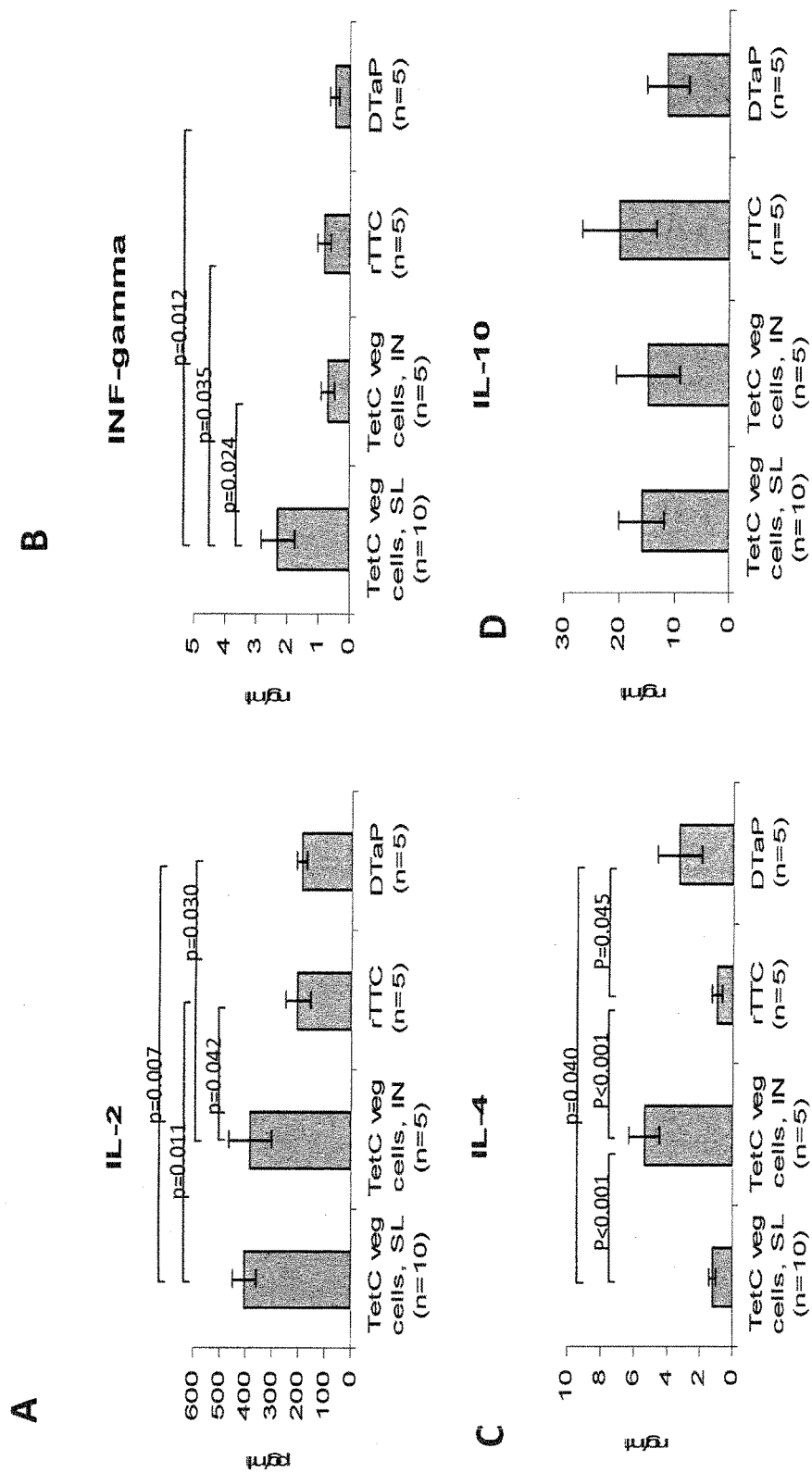

FIG. 36 panels A-D show serum cytokine serum levels two weeks after a third immunization of subjects. The mice were immunized sublingually with lyophilized *B. subtilis* vegetative cells BB3059, intranasally with lyophilized *B. subtilis* vegetative cells BB3059, sublingually with purified recombinant TetC fragment, or intramuscularly with commercial DTAP vaccine.

FIG. 36 panel A shows that subjects sublingually or intranasally immunized with lyophilized *B. subtilis* vegetative cells BB3059 had twice as much interleukin-2 in serum compared to subjects immunized sublingually with either purified recombinant TetC and or intramuscularly with DTAP vaccine. FIG. 34 panel B shows substantial interferon-gamma serum concentrations for subjects sublingually immunized with lyophilized *B. subtilis* vegetative cells BB3059 expressing TetC and subjects immunized with intranasally with lyophilized *B. subtilis* vegetative cells BB3059 expressing TetC, sublingually with purified recombinant TetC, or intramuscularly with DTAP vaccine. FIG. 34 panel C shows increased interleukin-4 serum concentrations for subjects intranasally immunized with lyophilized *B. subtilis* vegetative cells BB3059 expressing TetC. FIG. 34 panel D shows comparable interleukin-10 serum concentrations for subjects immunized sublingually with purified recombinant TetC compared to subjects sublingually or intranasally immunized with lyophilized *B. subtilis* vegetative cells BB3059, or subjects immunized sublingually with DTAP vaccine. Thus, lyophilized *B. subtilis* vegetative cells BB 3059 expressing TetC induced greater or comparable amounts of serum cytokines.

Example 29

Lyophilized *B. Subtilis* Vegetative Cells Expressing TetC Increased Immunoglobulin Levels Fecal, vaginal and saliva anti-TetC IgG and IgA levels were analyzed in mice inoculated with lyophilized *B. subtilis* vegetative cells expressing TetC. Mice were immunized: sublingually with control lyophilized vegetative cells, sublingually with lyophilized *B. subtilis* vegetative cells BB3059 expressing TetC, intranasally with lyophilized *B. subtilis* vegetative cells BB3059 expressing TetC, or intramuscularly with commercial DTAP vaccine.

Figure 37:
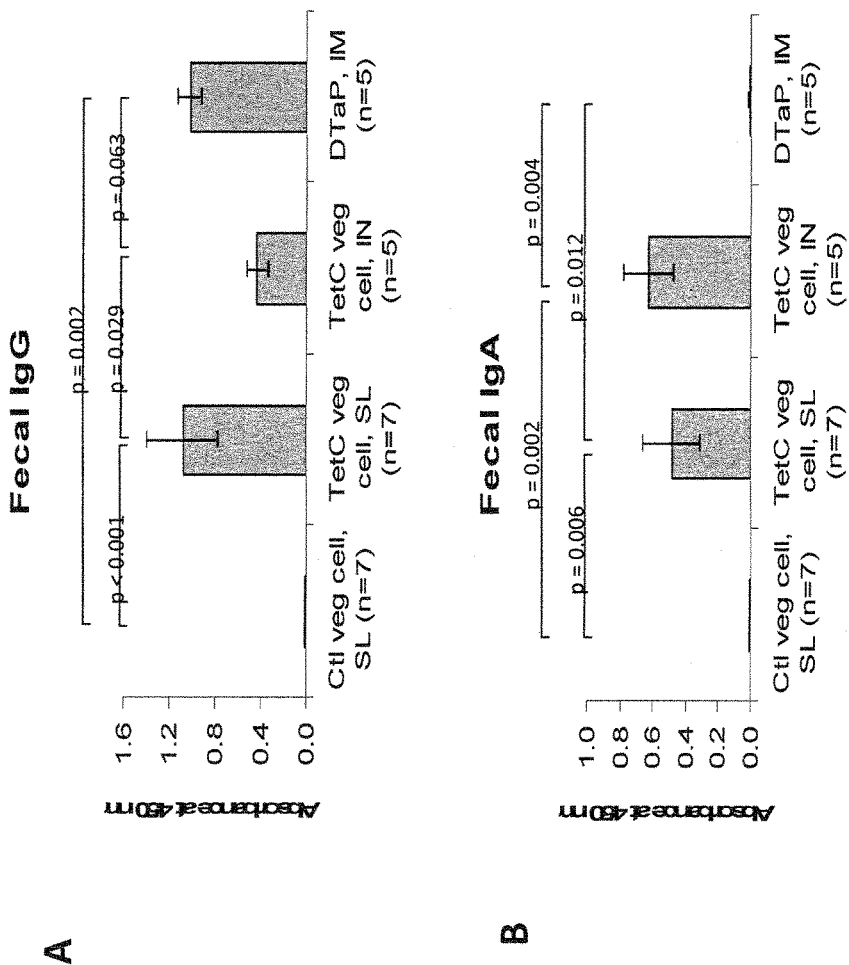

FIG. 37 panel A shows high IgG fecal content in mice inoculated sublingually with lyophilized *B. subtilis* vegetative cells BB3059 expressing TetC, subjects inoculated intramuscularly with commercial DTAP vaccine, and subjects inoculated intranasally with lyophilized *B. subtilis* vegetative cells BB3059 expressing TetC. Little or no IgG fecal content was observed in subjects inoculated sublingually with control lyophilized *B. subtilis* vegetative cells. FIG. 37 panel B shows high IgA fecal content in mice inoculated intranasally with lyophilized *B. subtilis* vegetative cells BB3059 expressing TetC and mice inoculated sublingually with *B. subtilis* vegetative cells BB3059 expressing TetC. Little or no IgA fecal content was observed in mice inoculated sublingually with control lyophilized *B. subtilis* vegetative cells or mice inoculated intramuscularly with commercial DTAP vaccine.

Figure 38:
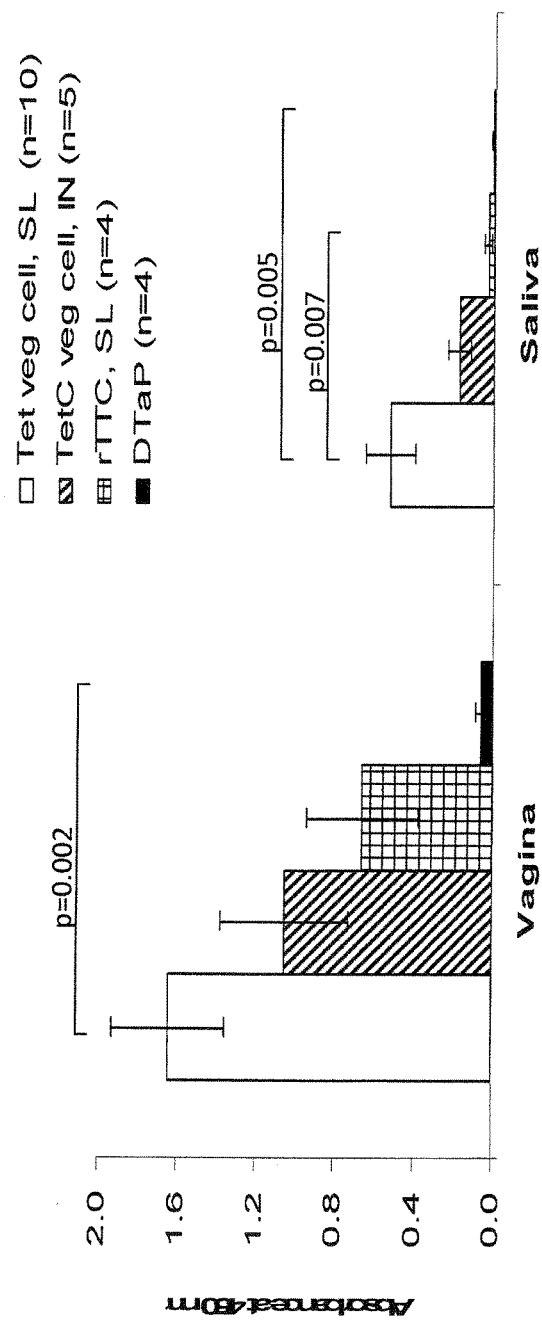

Subjects were immunized sublingually with lyophilized *B. subtilis* vegetative cells BB3059 expressing TetC, intranasally with lyophilized *B. subtilis* vegetative cells BB3059 expressing TetC, sublingually with purified recombinant TetC, or intramuscularly with commercial DTAP vaccine. Murine vaginal samples and saliva samples were assayed for TetC-specific IgA. FIG. 38 shows that higher amounts of TetC-specific IgA were detected in the vaginal samples compared to the saliva samples. In both the vaginal samples and saliva samples, higher amounts of TetC-specific IgA were detected in subjects immunized sublingually with lyophilized *B. subtilis* vegetative cells BB3059 expressing TetC, and the subjects immunized intranasally with lyophilized *B. subtilis* vegetative cells BB3059 expressing TetC. Much lower levels of TetC-specific IgA were detected in subjects immunized sublingually with purified recombinant TetC (30%-60% less) and in subjects immunized intramuscularly with commercial DTAP vaccine (90% less).

Thus, lyophilized *B. subtilis* vegetative cells expressing TetC generally resulted in greater immunoglobulin amounts in excretions or body fluids than results for commercial DTaP vaccine.

Example 30

Lyophilized *B. Subtilis* Vegetative Cells Expressing TetC Increased Immunoglobulin Levels and Reduced MHC Class II Staining MHC class II staining of tissues of mice inoculated with *B. subtilis* vegetative cells expressing TetC compared to tissue inoculated with control vegetative cells was analyzed and compared to commercial vaccines. Mice were immunized sublingually with either lyophilized *B. subtilis* vegetative cells BB3059 expressing TetC or control vegetative cells.

Figure 39:
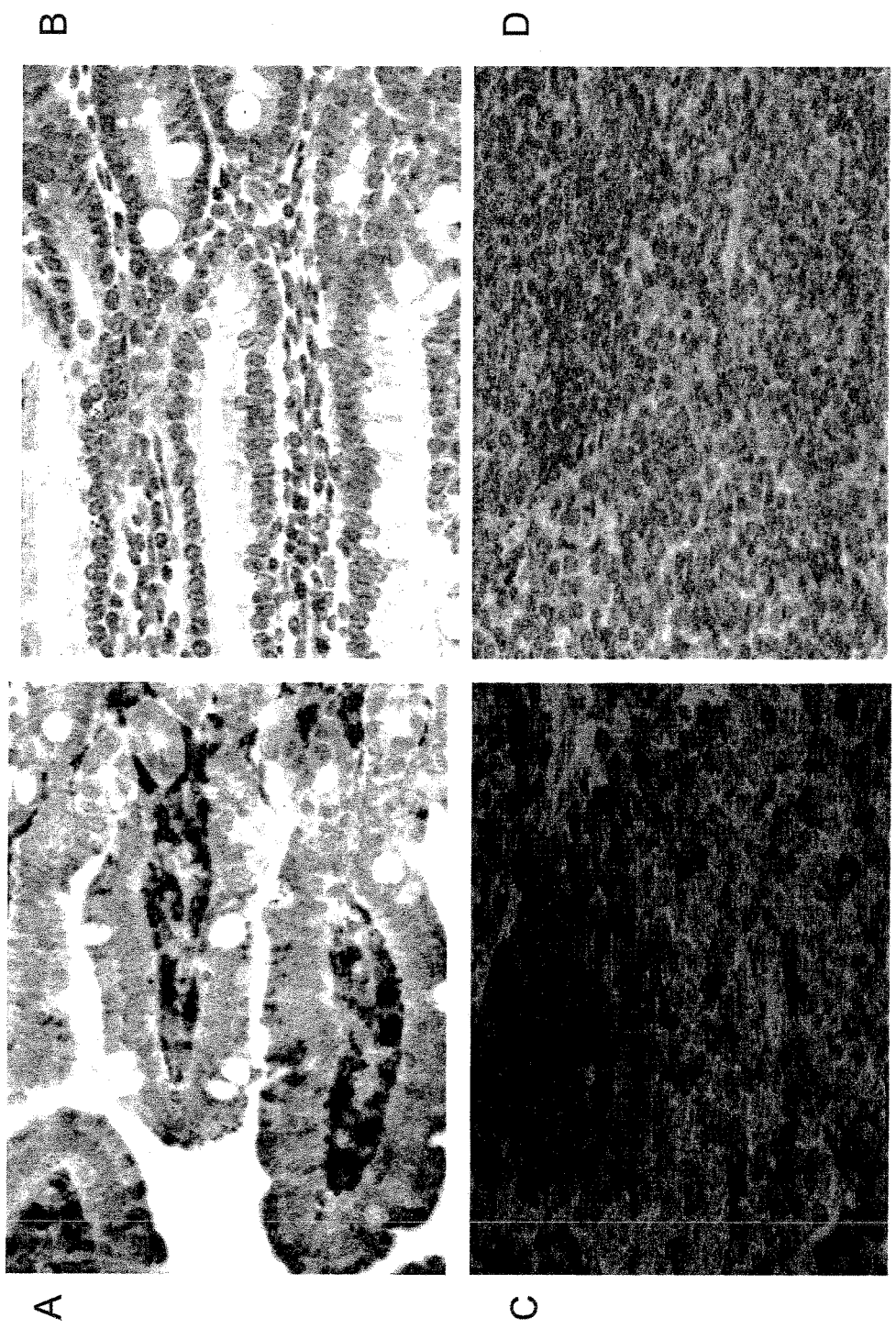

Subjects were sacrificed 24 hours after sublingual immunization and MHC class II deposition staining was performed on the murine spleen tissue (FIG. 39 panels A and B) and murine intestinal tract tissue (FIG. 39 panels C and D).

FIG. 39 shows extensive MHC class II deposition on murine spleen tissue (panel A) and murine intestinal tract tissue (panel C), respectively, from mice sublingually immunized with lyophilized B. subtilis vegetative cells BB3059 expressing TetC. Extensive MAC immunostaining with various patterns of staining of the cells was observed. FIG. 39 panels B and D show MHC class II deposition on murine spleen tissue and murine intestinal tract tissue, respectively, from mice sublingually immunized with control vegetative cells. Little or no MHC class II immunostaining was observed on the murine tissue.

Thus, mice inoculated with lyophilized B. subtilis vegetative cells BB3059 expressing TetC showed much more MHC class II deposition compared to mice inoculated with control cells.

Example 33

Inoculation Using Adjuvant and Lyophilized B. Subtilis Vegetative Cells

Fecal, serum and saliva samples from piglets inoculated with lyophilized B. subtilis vegetative cells BB3059 expressing TetC were analyzed for immunoglobulin levels.

Figure 40:
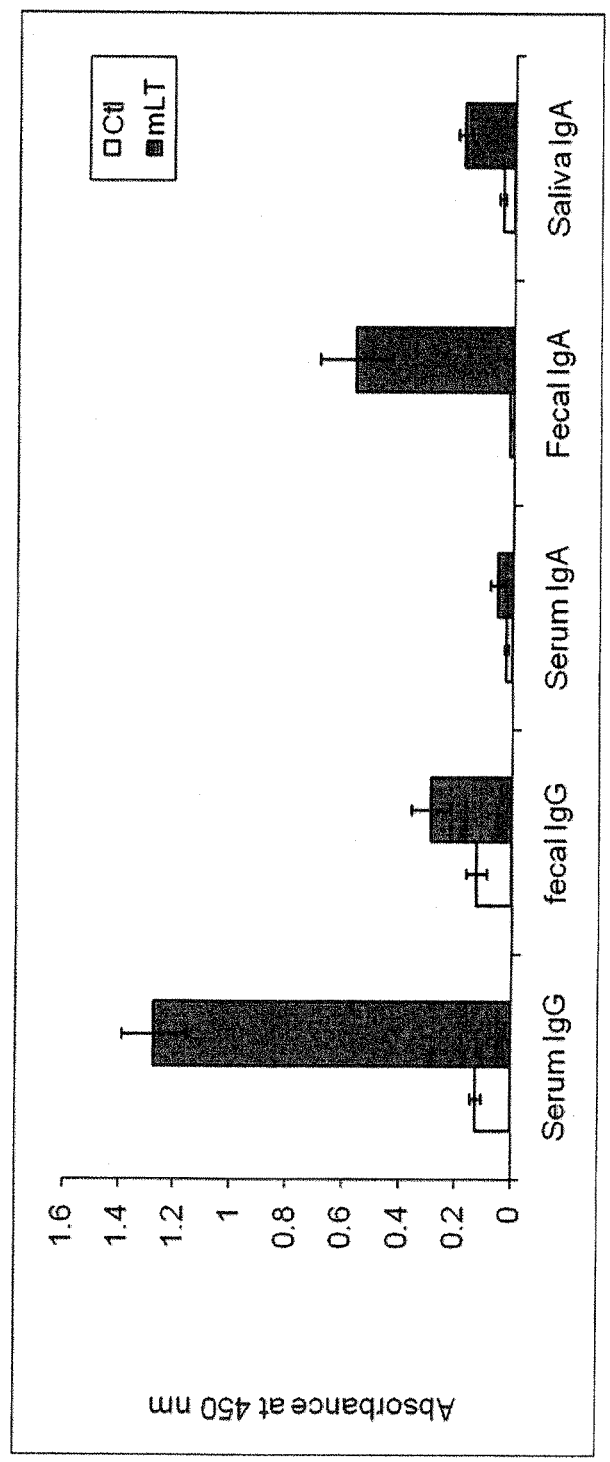

Anti-mLT IgG and IgA levels were detected in serum, fecal and saliva samples from piglets 14 days after a fourth sublingual immunization with lyophilized B. subtilis vegetative cells expressing TetC with adjuvant or without mLT adjuvant. The data in FIG. 40 show that in each of the serum, fecal, and saliva samples animals administered lyophilized B. subtilis lyophilized B. subtilis vegetative cells BB3059 with mLT adjuvant produced higher levels of IgG and IgA than animals administered lyophilized control vegetative cells only.

Figure 41:
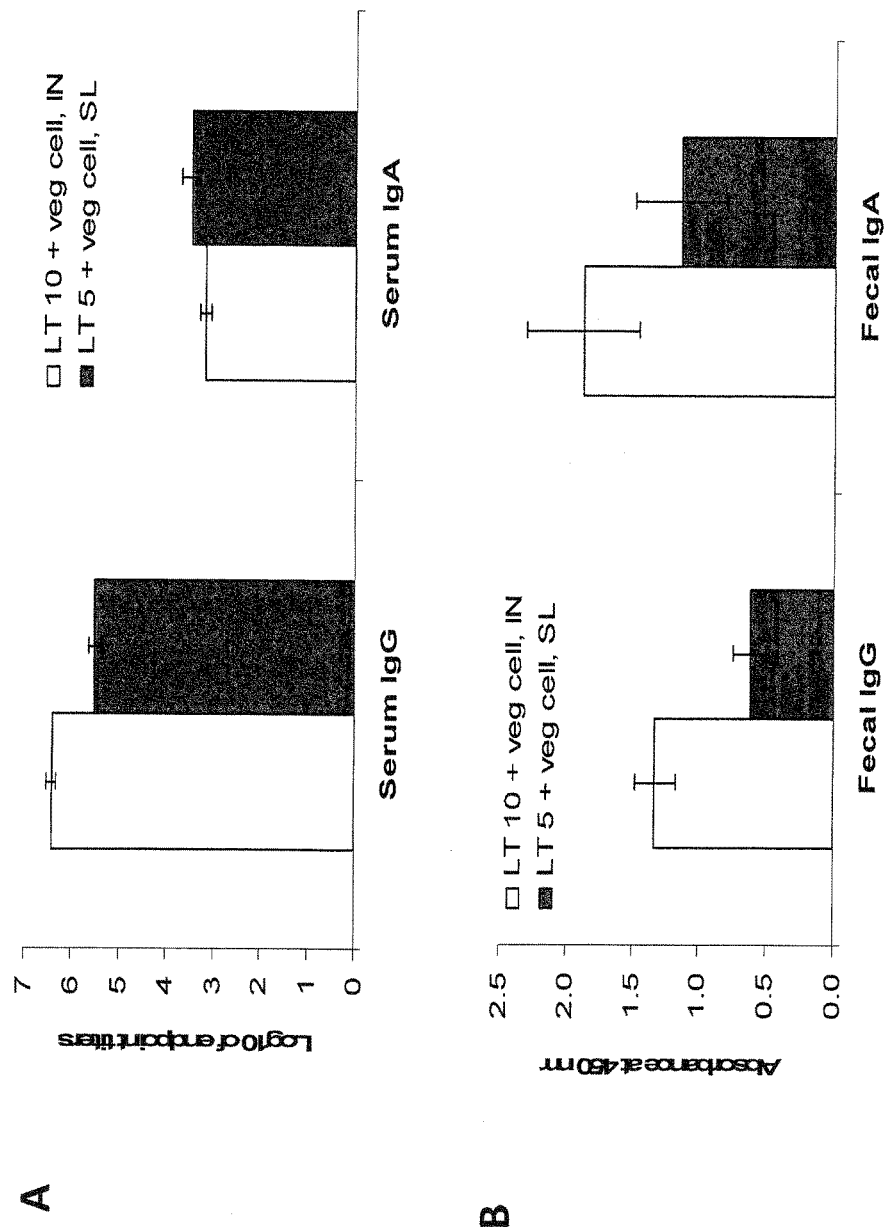

FIG. 41 shows a serum and fecal anti-mLT IgG and IgA titer for mice 14 days after a third immunization or fourth immunization. The subjects were immunized either sublingually with lyophilized B. subtilis vegetative cells expressing TetC and 5 µg of mLT adjuvant (LT 5+veg cells, SL; closed bars), or intranasally with lyophilized B. subtilis vegetative cells expressing TetC and 10 µg of mLT adjuvant (LT 10+veg cells, IN; open bars). FIG. 41 panel A shows comparable serum anti-mLT IgG and IgA for mice sublingually and intranasally immunized. FIG. 41 panel B shows that fecal IgA was higher than fecal IgG for both sublingually or intranasally immunized subjects.

Example 31

Inoculation Using Adjuvant and Lyophilized B. Subtilis Vegetative Cells Expressing TetC Piglets were immunized sublingually with lyophilized B. subtilis vegetative cells BB3059 expressing TetC, sublingually with lyophilized B. subtilis vegetative cells BB3059 expressing TetC and mLT adjuvant, orally with lyophilized B. subtilis vegetative cells BB3059 expressing TetC, and sublingually with control lyophilized B. subtilis vegetative cells. Serum samples were collected and assayed for TetC specific antibodies.

Figure 42:
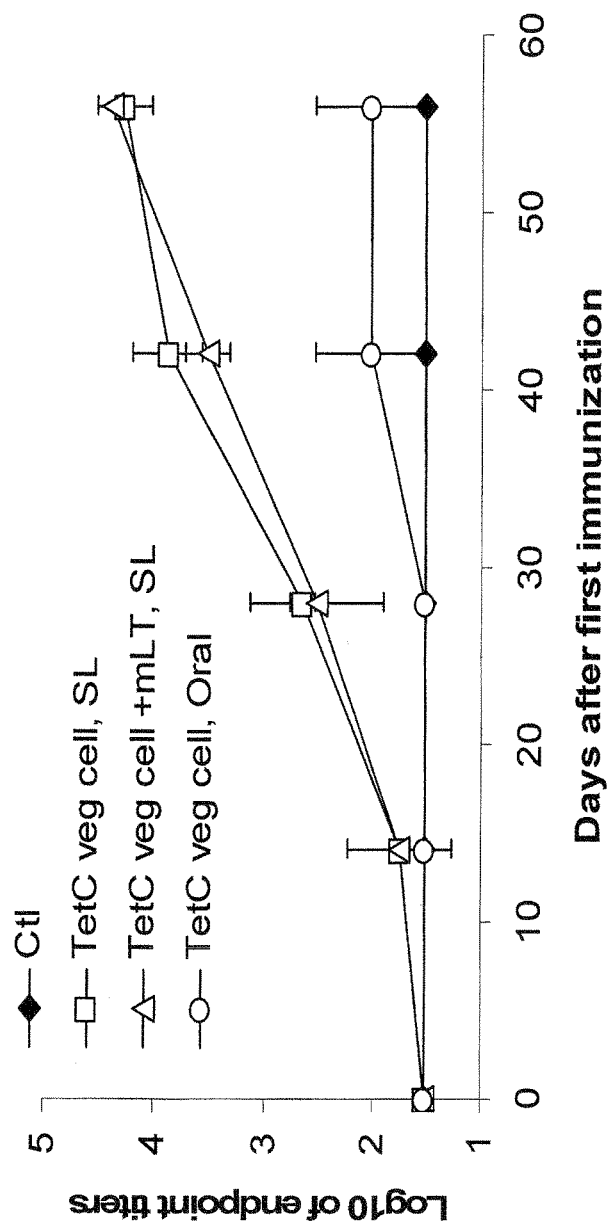

FIG. 42 shows higher serum anti-TetC antibody titer for subjects immunized sublingually with lyophilized B. subtilis vegetative cells BB3059 expressing TetC with or without mLT adjuvant compared to subjects immunized orally with either lyophilized B. subtilis vegetative cells BB3059 expressing TetC or control vegetative cells. No statistically significant difference was observed in immunoglobulin levels between inoculating subjects with strain BB3059 expressing TetC with or without mLT. Control vegetative cells did not induce antibody production in subjects.

Example 32

Optimization of Immunization Schedule

To further determine the optimal immunization schedule, subjects were immunized at different intervals and serum titer was analyzed.

FIG. 43 shows serum titer (ordinate) as a function of time (abscissa) in mice immunized with dried vegetative cell vaccine expressing TetC according to the following schedule: biweekly, monthly, or bimonthly. The data show high serum titer for mice immunized biweekly and monthly.

Example 33

Vaccination Against Ragweed Using Recombinant Lyophilized B. Subtilis Spores and Vegetative Cells Compositions of lyophilized B. subtilis spores and vegetative cells are prepared that encode and express an antigen known to be an allergen, for example, the whole of or a part of antigen E of ragweed (genus Ambrosia or other members of Asteraceae), which is an antigen associated with this pollen.

Spores and vegetative cells are prepared that encode all or a portion of antigen E of ragweed either displaying on the surface of the spore or produced cytoplasmically in the cell. The constructs are grown and production of the antigen is determined by Western blot or immunoassays.

Subjects are inoculated with the lyophilized B. subtilis spores or lyophilized B. subtilis vegetative cells carrying the constructs encoding the ragweed antigen. Serum titer, extent of protective immunogenicity, minimum effective dose, and survival rates are determined, and data are obtained to show that the constructs are potential improved vaccination agents. The constructs are tested using numerous routes of administration, for example sublingual, intranasal, oral, ocular, rectal, vaginal, and intravenous.

Immunological data are obtained to determine the extent that the lyophilized B. subtilis spores and vegetative cells protect cells, tissue and a subject from developing indicia of allergic reactions, or reduce the severity of the allergic reaction to ragweed.

Advantages of inoculating a subject with the lyophilized B. subtilis spores and vegetative cells encoding a ragweed antigen are shown. Improved immunization results are achieved with these constructs compared to standard methods of treating allergies including ingesting prescription drugs for example antihistamines and steroids, or a receiving a regimen of allergy shots that block the effects of IgE antibodies. The lyophilized B. subtilis spores and lyophilized B. subtilis vegetative cells individually or in combination are also shown to be effective.

Sublingual or intranasal immunization schedules can be carried out by the patient using prepared unit dosage kits, greatly reducing or eliminating health care costs for allergy patients. Methods, compositions and kits herein are made for other allergens, for example dust mite proteases and gluten.

Example 34

Vaccination Against Tumor Antigens Using Recombinant Lyophilized B. subtilis Spores and Vegetative Cells Lyophilized B. subtilis spores and vegetative cells containing recombinant constructs encoding and expressing an antigen present on tumor or a protein associated with the presence or growth of a tumor or cancer are prepared. The antigen of the tumor is for example human epidermal growth factor receptor 2 (HER2) which is associated with a class of breast cancer tumors. Such immunization is particularly suitable for breast cancer survivors in remission, to prevent a recurrence and metastasis.

Subjects are administered lyophilized B. subtilis spore or vegetative cell vaccine prepared from cells having constructs encoding the HER2 antigen. The constructs are tested using numerous routes of administration, for example sublingual, intranasal, oral, ocular, rectal, vaginal, and intravenous.

Data show that administering the lyophilized B. subtilis spores and vegetative cells encoding the HER2 antigen protects the subject from the indicia of breast cancer tumors. The lyophilized B. subtilis spores and lyophilized B. subtilis vegetative cells shown herein are also used under different conditions or administration methods, or in combination.

Numerous other lyophilized B. subtilis spores and vegetative cells containing recombinant constructs encoding and expressing an antigen are prepared, for example the vaccination antigen is for example nestin, carcinoembryonic antigen (CEA), cancer antigen 125 (CA-125) and human chorionic gonadotropin (HCG).

a vegetative promoter for cytoplasmic vegetative expression of the antigen in the vegetative cells, or a sporulation promoter for expression of the antigen as a fusion to a spore coat protein on the Bacillus subtilis spores;

collecting the cells or the spores from the culture by centrifugation and heat-stabilizing the antigen by lyophilizing the vegetative cells or the spores to obtain a heat stable vaccine preparation having heat stable immunogenic potency for at least 12 months at a temperature of 45° C. comparable to the vaccine stored at 4° C.; and, contacting a mucosal tissue of the subject with the heat stable vaccine preparation which induces an immune response and immunizes the subject to the infectious agent, the tumor, or to the allergen.

2. The method according to claim 1, wherein the infectious agent is selected from the group of: a bacterium, a fungus, a virus, a protozoan, or a protein product thereof.

3. The method according to claim 2, wherein the infectious agent is at least one bacterium selected from the group consisting of: *Bacillus anthracis*; *Clostridium tetani*; *Clostridium difficile*; *Clostridium perfringens*; *Corynebacterium diphtheriae*; *Bordetella pertussis*; *Mycobacterium tuberculosis*; *Salmonella enterica*; *Staphylococcus aureus*; *Staphylococcus epidermis*; *Streptococcus pneumoniae*; *Streptococcus mutans*; *Treponema pallidum*; *Pseudomonas aeruginosa*; *Neisseria gonorrhoeae*; *Escherichia coli*; *Escherichia coli* O157:H7; *Shigella enteritis*; *Shigella flexneri*; *Campylobacter jejuni*; *Yersinia pseudotuberculosis*; *Yersinia pestis*; *Listeria monocytogenes*; and *Vibrio cholerae*.

---

---

What is claimed is:

1. A method of using a heat stable vaccine preparation to immunize a subject to an infectious agent, a tumor, or an allergen, the method comprising:

providing a *Bacillus subtilis* bacterial cell culture containing *Bacillus subtilis* vegetative cells or providing a preparation of *Bacillus subtilis* spores, the vegetative cells and the spores each expressing an isolated nucleotide sequence encoding an antigen of the infectious agent, the tumor, or the allergen, the nucleotide sequence is operably linked to either:

4. The method according to claim 2, wherein the infectious agent is at least one virus selected from the group consisting of: human immunodeficiency virus (HIV); influenza virus A; influenza virus B; influenza virus A/H1N1; polio; Herpes simplex virus-1; Herpes simplex virus-2; smallpox; measles; mumps; rubella; rotavirus; chicken pox; rabies; West Nile virus; Ebola hemorrhagic fever; eastern equine encephalitis; norovirus; Hepatitis A; Hepatitis B; and Hepatitis C.

5. The method according to claim 2, wherein the infectious agent is at least one fungus selected from the group consisting of: *Cryptococcus Gattii: Cryptococcus neoformans* v. *neoformans; Candida albicans; Aspergillus flavus*; and *Aspergillus fumigatus*.

6. The method according to claim 2, wherein the infectious agent is at least one protozoan selected from the group consisting of: *Entamoeba histolytica; Giardia lamblia; Cryptosporidium parvum; Naegleria fowleri; Naegleria gruberi; Plasmodium falciparum; Plasmodium vivax; Plasmodium malariae*; and *Plasmodium ovale*.

7. The method according to claim 1, wherein the antigen is a rotavirus antigen selected from the group of: bovine, human, and murine origin.

8. The method according to claim 7, wherein the rotavirus antigen is a viral virion protein selected from at least one of the group of VP2, VP4, VP6, VP7, NSP4, and a portion or a derivative thereof.

9. The method according to claim 1, wherein the allergen comprises a macromolecule or portion thereof associated with an increased immunoglobulin level or allergic response in the subject, wherein the allergen comprises an environmental allergen, animal or plant allergen, or food allergen, selected from the group consisting of: allergen associated with pollen, dust mite proteases, fungus, mold, pet dander, saliva, shellfish, seafood, a legume, and peanuts.

10. The method according to claim 1, wherein the subject is a vertebrate animal.

11. The method according to claim 10, wherein the vertebrate animal is selected from at least one of the group consisting of: an agricultural animal, a high value zoo animal, a research animal, a human, and a wild animal in a dense human environment.

12. The method according to claim 1, wherein contacting the mucosal tissue of the subject further comprises administering the composition by a route selected from at least one of the group of: intravenous, intramuscular, intraperitoneal, intradermal, intrapulmonary, intravaginal, rectal, oral, buccal, sublingual, intranasal, intraocular, and subcutaneous.

13. The method according to claim 1, wherein contacting the mucosal tissue of the subject comprises applying to the mucosal tissue at least one from the group of: an aerosol, a mist, a nose drop, an eye drop, a mouth drop, a capsule, a tablet, a pill, a powder, a granule, a fluid, a suspension, an emulsion, a gel, a patch, and a lozenge.

14. The method according to claim 1, wherein contacting the mucosal tissue of the subject further comprises contacting the mucosal tissue with an adjuvant.

15. The method according to claim 14, wherein the adjuvant is selected from at least one of the group or: cholera toxin, a non-toxic variant of *Escherichia coli* labile toxin, and a portion or a derivative thereof.

16. The method according to claim 1, further comprising observing resistance of the composition to at least one condition selected from the group of: heat, drying, freezing, deleterious chemicals, and radiation.

17. The method according to claim 16, wherein observing the resistance to heat comprises observing resistance at 60° C. or 45° C. for at least one period of time selected from the group of: at least one month, at least six months, at least one year, and at least two years.

18. The method according to claim 16, wherein observing resistance comprises observing a heat treated composition maintaining ability to confer full protective immunity or partial protective immunity, wherein the partial protective immunity comprises a percentage of the full protective immunity, wherein the percentage comprises at least 40%, at least 50%, at least 60%, at least 70%, at least 80%, or at least 90%.

19. The method according to claim 1, further comprising:
measuring an antibody titer in serum of the subject administered the composition, wherein an increase in antibody for the antigen in comparison to a control serum is an indication of efficacy of the immunogenicity of the composition.

20. The method according to claim 1, further comprising:
measuring an amount of antigen shedding in the subject having been afflicted by the infectious agent, wherein a decrease in fecal antigen as compared to that in a control also afflicted by the infectious agent and not contacted with the composition is a measure of efficacy of the immunogenicity of the composition.

21. The method according to claim 1, wherein the antigen comprises a *Clostridium tetani* toxin antigen, wherein the nucleotide sequence is operably linked to the promoter for the cytoplasmic vegetative expression of the *Clostridium tetani* toxin antigen or for expression of the *Clostridium tetani* toxin antigen as the fusion to the spore coat protein, and the vegetative cell and the spore are associated with the *Clostridium tetani* toxin antigen.

22. A method of using a heat stable vaccine preparation to immunize a subject to an infectious agent, a tumor, or an allergen, the method comprising:
providing *Bacillus* vegetative cells expressing an isolated nucleotide sequence encoding an antigen or the infectious agent, the tumor, or the allergen, the nucleotide sequence is operably linked to a Pspac promoter containing a sequence comprising SEQ ID NO: 1 for cytoplasmic vegetative expression of the antigen;
collecting the cells from the culture by centrifugation, and heat-stabilizing the antigen by lyophilizing the vegetative cells to obtain the resulting heat stable vaccine preparation; and,
contacting a mucosal tissue of the subject with the heat stable vaccine preparation which induces an immune response and immunizes the subject to the infectious agent, the tumor, or to the allergen.

23. A method of using a heat stable vaccine preparation to immunize a subject to an infectious agent, a tumor, or an allergen, the method comprising:
providing *Bacillus subtilis* spores expressing an isolated nucleotide sequence encoding an antigen of the infectious agent, the tumor, or the allergen, the nucleotide sequence is operably linked to a gene for a spore coat protein for expression of the antigen as a fusion to the spore coat protein;
collecting the spores from the culture by centrifugation, and heat-stabilizing the antigen expressed on the spore coat protein by lyophilizing the spores to obtain the resulting heat stable vaccine preparation which is stable for at least 12 months at a temperature of 45° C. comparable to the vaccine stored at 4° C.; and,
contacting a mucosal tissue of the subject with the heat stable vaccine preparation which induces an immune response and immunizes the subject to the infectious agent, the tumor, or to the allergen.

* * * * *

UNITED STATES PATENT AND TRADEMARK OFFICE
CERTIFICATE OF CORRECTION

PATENT NO. : 9,610,333 B2  
APPLICATION NO. : 12/987280  
DATED : April 4, 2017  
INVENTOR(S) : Herrmann et al.

Page 1 of 1

It is certified that error appears in the above-identified patent and that said Letters Patent is hereby corrected as shown below:

In the Claims

Claim 19, Column 46, Line 6: delete "scrum" and insert --serum--

Claim 22, Column 46, Line 31: delete "or" and insert --of--

Signed and Sealed this
Eighth Day of August, 2017

Joseph Matal
*Performing the Functions and Duties of the*
*Under Secretary of Commerce for Intellectual Property and*
*Director of the United States Patent and Trademark Office*